(12) United States Patent
Wrigg

(10) Patent No.: US 10,918,924 B2
(45) Date of Patent: Feb. 16, 2021

(54) FRAMEWORKS, DEVICES AND METHODOLOGIES CONFIGURED TO ENABLE DELIVERY OF INTERACTIVE SKILLS TRAINING CONTENT, INCLUDING CONTENT WITH MULTIPLE SELECTABLE EXPERT KNOWLEDGE VARIATIONS

(71) Applicant: RLT IP Ltd., Gosport (GB)

(72) Inventor: Darren Wrigg, Sydney (AU)

( * ) Notice: Subject to any disclaimer, the term of this patent is extended or adjusted under 35 U.S.C. 154(b) by 326 days.

(21) Appl. No.: 15/548,089

(22) PCT Filed: Feb. 2, 2016

(86) PCT No.: PCT/AU2016/000020
§ 371 (c)(1),
(2) Date: Aug. 1, 2017

(87) PCT Pub. No.: WO2016/123648
PCT Pub. Date: Aug. 11, 2016

(65) Prior Publication Data
US 2018/0015345 A1    Jan. 18, 2018

(30) Foreign Application Priority Data

Feb. 2, 2015   (AU) ............................... 2015900313
Feb. 2, 2015   (AU) ............................... 2015900314
(Continued)

(51) Int. Cl.
G09B 5/06           (2006.01)
G09B 5/12           (2006.01)
(Continued)

(52) U.S. Cl.
CPC .............. *A63B 69/00* (2013.01); *A41D 1/005* (2013.01); *A63B 24/0006* (2013.01);
(Continued)

(58) Field of Classification Search
CPC ............... A41D 1/005; A63B 24/0006; A63B 2225/50; A63B 2225/89; A63B 2220/56;
(Continued)

(56) References Cited

U.S. PATENT DOCUMENTS 6,293,802 B1   9/2001   Ahlgren
6,389,368 B1   5/2002   Hampton
(Continued)

FOREIGN PATENT DOCUMENTS

CN   101441776 A   5/2009
CN   101652808 A   2/2010
(Continued)

OTHER PUBLICATIONS

International Search Report and Written Opinion dated Apr. 27, 2016 from International Application No. PCT/AU2016/000020 filed Feb. 2, 2016, 9 pages.
(Continued)

*Primary Examiner* — Robert J Utama

(57) ABSTRACT

The present invention relates to delivery of content that is driven by input from one or more performance sensor units, such as performance sensor units configured to monitor motion-based performances and/or audio-based performances. Embodiments of the invention include software and hardware, and associated methodologies, associated with the generation, distribution, and execution of such content. Particular attention is paid to technologies that enable the delivery of skills training content that provides for expert knowledge variations in training content for various skills.

17 Claims, 48 Drawing Sheets

(30) Foreign Application Priority Data

| | | |
|---|---|---|
| May 8, 2015 | (AU) | 2015901665 |
| May 8, 2015 | (AU) | 2015901666 |
| May 8, 2015 | (AU) | 2015901669 |
| May 8, 2015 | (AU) | 2015904670 |
| May 27, 2015 | (AU) | 2015901945 |
| May 29, 2015 | (AU) | 2015902004 |
| Jul. 30, 2015 | (AU) | 2015903037 |
| Jul. 31, 2015 | (AU) | 2015903050 |
| Dec. 10, 2015 | (AU) | 2015905108 |

(51) Int. Cl.
```
A63B 69/00      (2006.01)
A41D 1/00       (2018.01)
A63B 24/00      (2006.01)
A63B 71/06      (2006.01)
G06F 19/00      (2018.01)
G06N 5/04       (2006.01)
G06Q 30/06      (2012.01)
A63B 69/06      (2006.01)
G09B 19/00      (2006.01)
G16H 40/63      (2018.01)
G16H 20/30      (2018.01)
G09B 15/00      (2006.01)
G09B 5/04       (2006.01)
```

(52) U.S. Cl.
CPC .......... *A63B 24/0062* (2013.01); *A63B 69/06* (2013.01); *A63B 71/0622* (2013.01); *G06F 19/3481* (2013.01); *G06N 5/04* (2013.01); *G06Q 30/0601* (2013.01); *G09B 5/065* (2013.01); *G09B 5/125* (2013.01); *G09B 19/0038* (2013.01); *G16H 20/30* (2018.01); *G16H 40/63* (2018.01); *A63B 2024/0009* (2013.01); *A63B 2024/0012* (2013.01); *A63B 2071/063* (2013.01); *A63B 2071/0655* (2013.01); *A63B 2220/40* (2013.01); *A63B 2220/56* (2013.01); *A63B 2220/803* (2013.01); *A63B 2220/806* (2013.01); *A63B 2220/836* (2013.01); *A63B 2220/89* (2013.01); *A63B 2225/50* (2013.01); *G09B 5/04* (2013.01); *G09B 15/00* (2013.01)

(58) Field of Classification Search
CPC ............ A63B 69/06; A63B 2071/0655; G16H 40/63; G16H 20/30; G09B 5/125; G09B 19/0038; G06N 5/04
See application file for complete search history.

(56) References Cited

U.S. PATENT DOCUMENTS

| | | | |
|---|---|---|---|
| 7,825,815 B2 * | 11/2010 | Shears | A61B 5/1127 340/573.1 |
| 9,223,936 B2 * | 12/2015 | Aragones | G06F 19/3481 |
| 10,216,893 B2 * | 2/2019 | Hong | A61B 5/4866 |
| 2005/0196737 A1 | 9/2005 | Mann | |
| 2006/0025229 A1 | 2/2006 | Mahajan et al. | |
| 2006/0166737 A1 * | 7/2006 | Bentley | A61B 5/1122 463/30 |
| 2007/0063850 A1 | 3/2007 | DeVaul et al. | |
| 2009/0311657 A1 | 12/2009 | Dodelson et al. | |
| 2010/0053867 A1 | 3/2010 | Ellis et al. | |
| 2010/0056876 A1 | 3/2010 | Ellis et al. | |
| 2010/0121227 A1 | 5/2010 | Stirling et al. | |
| 2010/0176952 A1 | 7/2010 | Bajcsy et al. | |
| 2010/0184563 A1 | 7/2010 | Molyneux et al. | |
| 2010/0283630 A1 | 11/2010 | Alonso | |
| 2011/0153042 A1 | 6/2011 | Burton et al. | |
| 2011/0259176 A1 | 10/2011 | Pillhofer et al. | |
| 2011/0270135 A1 * | 11/2011 | Dooley | G16H 50/30 600/595 |
| 2012/0029666 A1 | 2/2012 | Crowley et al. | |
| 2012/0046901 A1 | 2/2012 | Green et al. | |
| 2012/0157263 A1 * | 6/2012 | Sivak | G06F 3/014 482/4 |
| 2012/0183940 A1 | 7/2012 | Aragones et al. | |
| 2013/0029791 A1 * | 1/2013 | Rose | G09B 19/0038 473/409 |
| 2013/0040763 A1 | 2/2013 | Davidson | |
| 2013/0203475 A1 | 8/2013 | Kil et al. | |
| 2013/0233152 A1 | 9/2013 | Pillhofer et al. | |
| 2013/0274587 A1 | 10/2013 | Coza et al. | |
| 2013/0330054 A1 | 12/2013 | Lokshin | |
| 2014/0100010 A1 | 4/2014 | Lee et al. | |
| 2014/0114453 A1 | 4/2014 | Bentley | |
| 2014/0142459 A1 * | 5/2014 | Jayalth | A61B 5/0022 600/547 |
| 2014/0161322 A1 | 6/2014 | Cheng et al. | |
| 2014/0172134 A1 | 6/2014 | Meschter | |
| 2014/0174174 A1 | 6/2014 | Uehara et al. | |
| 2014/0235230 A1 | 8/2014 | Raleigh | |
| 2014/0257743 A1 | 9/2014 | Lokshin et al. | |
| 2014/0263224 A1 | 9/2014 | Becker | |
| 2014/0272838 A1 | 9/2014 | Becker | |
| 2014/0278139 A1 | 9/2014 | Hong et al. | |
| 2014/0320481 A1 | 10/2014 | Vivi | |
| 2014/0376876 A1 | 12/2014 | Bentley et al. | |
| 2015/0019135 A1 * | 1/2015 | Kacyvenski | A61B 5/0488 702/19 |
| 2015/0072326 A1 | 3/2015 | Mauri et al. | |
| 2015/0118658 A1 * | 4/2015 | Mayou | A61B 5/14552 434/127 |
| 2015/0340066 A1 | 11/2015 | Lokshin et al. | |
| 2016/0077581 A1 * | 3/2016 | Shi | G06F 3/011 340/12.5 |
| 2016/0180248 A1 * | 6/2016 | Regan | G09B 5/00 706/12 |
| 2016/0330533 A1 | 11/2016 | Mangaud | |
| 2017/0061817 A1 | 3/2017 | May | |
| 2017/0197111 A1 * | 7/2017 | Mak | G06Q 10/06313 |
| 2018/0015345 A1 * | 1/2018 | Wrigg | G09B 19/0038 |
| 2018/0296878 A1 * | 10/2018 | Copelan | A63B 24/0006 |
| 2019/0069154 A1 * | 2/2019 | Booth | H04L 67/306 |

FOREIGN PATENT DOCUMENTS

| | | | | |
|---|---|---|---|---|
| CN | 102819863 A | 12/2012 | | |
| CN | 103135765 A | 6/2013 | | |
| CN | 103990285 B | 2/2017 | | |
| CN | 104126184 B | 1/2018 | | |
| EP | 3205379 A1 * | 8/2017 | ............ | A63B 71/06 |
| JP | 2008073285 A | 4/2008 | | |
| JP | 2008528195 A | 7/2008 | | |
| JP | 2012120579 A | 6/2012 | | |
| JP | 2013503694 A | 2/2013 | | |
| JP | 2014512205 A | 5/2014 | | |
| WO | 2011086466 A1 | 7/2011 | | |
| WO | 2012020242 A2 | 2/2012 | | |
| WO | 2014121374 A1 | 8/2014 | | |

OTHER PUBLICATIONS

Extended European Search Report dated Jun. 14, 2018 from European Application No. 167459833 filed Aug. 30, 2017, 7 pages.

Anderson et al., "YouMove: Enhancing Movement Training with an Augmented Reality Mirror", UIST '13 Proceedings of the 26th Annual ACM Symposium on User Interface Software and Technology, St. Andrews, Scotland, United Kingdom, Oct. 8-11, 2013, pp. 311-320.

International Search Report and Written Opinion dated Jun. 3, 2016 from International Application No. PCT/AU2016/050347 filed May 9, 2016, 14 pages.

CN 201680044207.6, "First Office Action," dated Apr. 15, 2019, 15 pages.

(56) References Cited

OTHER PUBLICATIONS

Communication pursuant to Article 94(3) EPC dated Oct. 14, 2019, European Patent Application No. 16871832.8, 4 pages.
EP 16745983.3, "Article 94(3) 1st OA," dated Dec. 11, 2019, 6 pages.
International Search Report and Written Opinion dated Jun. 21, 2016 from International Application No. PCT/AU2016/050348 filed May 9, 2016, 26 pages.
EP 16791825.9, "Article 94(3) 1st OA," dated Dec. 11, 2019, 6 pages.
International Search Report and Written Opinion dated Jul. 4, 2016 from International Application No. PCT/AU2016/000026 filed Feb. 2, 2016, 15 pages.
Extended European Search Report dated Mar. 29, 2019, European Patent Application No. 16871832.8, 7 pages.
Extended European Search Report dated Jan. 21, 2019 from European Application No. 16798963.1, 7 pages.
Extended European Search Report dated Jun. 14, 2018 from European Application No. 16745989.0 filed Aug. 31, 2017, 7 pages.
Extended European Search Report dated Sep. 26, 2018 from European Application No. 16791825.9, 7 pages.
Extended European Search Report dated Sep. 26, 2018 from European Application No. 16791826.7, 8 pages.
International Search Report and Written Opinion dated Jul. 11, 2016 from International Application No. PCT/AU2016/050415 filed May 27, 2016, 13 pages.
First Office Action dated Mar. 29, 2019, Chinese Patent Application No. 201680021231.8, 13 pages.
International Search Report and Written Opinion dated Feb. 20, 2017 from International Application No. PCT/AU2016/051220 filed Dec. 12, 2016, 21 pages.
First Office Action dated May 22, 2019 for Chinese Patent Application No. 201680020626.6, 10 pages.
CN 201680044207.6 Second Office Action dated Apr. 3, 2020, 9 pages.
JP 2018-509949, First Office Action, dated Apr. 21, 2020, 8 pages.
JP App No. 2017-558595, "First Office Action," dated Feb. 4, 2020, 12 pages.
JP App No. 2017-558596, "First Office Action," dated Feb. 4, 2020, 9 pages.
JP App No. 2017-561325, "First Office Action," dated May 26, 2020, 12 pages.
JP Application No. 2018-509948, "1st Office Action," dated Jun. 9, 2020, 14 pages.

* cited by examiner

| SKILL: STANDARD ROWING ACTION | | | | | | | | |
|---|---|---|---|---|---|---|---|---|
| REVIEWER A | | SUBJECT B | | ABILITY LEVEL X | | SET N | | |
| | $REP_1$ | $REP_2$ | $REP_3$ | $REP_4$ | $REP_5$ | $REP_6$ | $REP_7$ | $REP_8$ |
| $S_1$ | | X | | | | | | |
| $S_2$ | X | X | X | X | X | X | X | X |
| $S_3$ | | X | | | | | | |
| $S_4$ | | | X | | | | | |
| $S_5$ | | | | | X | X | X | X |
| $S_6$ | | | | | | | | |

FIG. 4A

| SKILL: STANDARD ROWING ACTION | | | | | | | | |
|---|---|---|---|---|---|---|---|---|
| REVIEWER A | | SUBJECT B | | ABILITY LEVEL X | | SET N | | |
| | $C_1$ | $C_2$ | $C_3$ | $C_4$ | $C_5$ | $C_6$ | $C_7$ | $C_8$ |
| $S_1$ | | | X | X | | | | |
| $S_2$ | X | | | | | | | |
| $S_3$ | | | | | | | | |
| $S_4$ | | | | | X | | | |
| $S_5$ | | | | | | | | X |
| $S_6$ | | | | | | | | |

FIG. 4B

FRAMEWORKS, DEVICES AND METHODOLOGIES CONFIGURED TO ENABLE DELIVERY OF INTERACTIVE SKILLS TRAINING CONTENT, INCLUDING CONTENT WITH MULTIPLE SELECTABLE EXPERT KNOWLEDGE VARIATIONS

FIELD OF THE INVENTION

The present invention relates to delivery of content that is driven by input from one or more performance sensor units, such as performance sensor units configured to monitor motion-based performances and/or audio-based performances. Embodiments of the invention include software and hardware, and associated methodologies, associated with the generation, distribution, and execution of such content.

BACKGROUND

Any discussion of the background art throughout the specification should in no way be considered as an admission that such art is widely known or forms part of common general knowledge in the field.

Various technologies have been developed thereby to enable integration between sensors, which monitor human activity, and training systems. For example, these have been applied in the context of sports-based training thereby to provide users with reporting based on monitored attributes such as heart rate, running pace, and distance travelled. In general, known technologies are effective in providing reporting on the outcome of human activity at a high level (for example, in the context of running, distance travelled), as opposed to enabling analysis of the manner in which the activity is performed (for example, again in the context of running, the form with which the person runs). Accordingly, whilst useful as training tools, they provide only a superficial and course tool with which to assess human performance.

SUMMARY OF THE INVENTION

It is an object of the present invention, at least in some embodiments to overcome or ameliorate at least one of the disadvantages of the prior art, or to provide a useful alternative.

The follow set of summary embodiments are provided to foreshadow potential patent claims based on a selection of technological aspects disclosed in the following Detailed Description. These are not intended to be limiting in any way on the scope of claims that might be pursued.

One embodiment provides a computer implemented method for enabling a user to configure operation of local performance monitoring hardware devices, the method including:

providing an interface configured to enable a user of a client device to select a set of downloadable content, wherein the set of downloadable content relates to one or more skills; and enabling the user to cause downloading of data representative of at least a portion of the selected set of downloadable content to local performance monitoring hardware associated with the user, wherein the downloading includes downloading of:

(i) sensor configuration data, wherein the sensor configuration data includes data that configures a set of one or more performance sensor units to operate in a defined manner thereby to provide data representative of an attempted performance of a particular skill;

(ii) state engine data, wherein the state engine data includes data that is configured to enable a processing device to identify attributes of the attempted performance of the particular skill based on the data provided by the set of one or more performance sensor units; and (iii) user interface data, wherein the user interface data includes data configured to enable operation of a user interface based on the identified attributes of the attempted performance of the particular skill;

the method further including enabling the user to select downloadable content defined by an expert knowledge variation for the selected one or more skills, wherein there are multiple expert knowledge variations available for the set of one or more skills.

One embodiment provides a computer implemented method wherein a first expert knowledge variations is associated with a first set of state engine data, and the second expert knowledge variation is associated with a second different set of state engine data, wherein the second different set of state engine data is configured to enable identification of one or more expert-specific attributes of a performance that are not identified using the first set of state engine data.

One embodiment provides a computer implemented method wherein the expert-specific attributes relate to a style of performance associated with the expert.

One embodiment provides a computer implemented method wherein the style of performance is represented by defined attributes of body motion that are observable using data derived from one or more motion sensor units.

One embodiment provides a computer implemented method wherein the expert-specific attributes relate to coaching knowledge associated with the expert.

One embodiment provides a computer implemented method wherein the one or more expert-specific attributes are defined based on a process that is configured to objectively define coaching idiosyncrasies.

One embodiment provides a computer implemented method wherein, for the selected set of one or more skills, there is a first selectable expert knowledge variation and a second selectable expert knowledge variation, wherein:

for the first selectable expert knowledge variation, the downloadable data configures the client device to identify, in data derived from the set of performance sensor units, a first set of observable data conditions associated with a given skill; and for the second selectable expert knowledge variation, the downloadable data configures the client device to identify, in data derived from the set of performance sensor units, a second different set of observable data conditions associated with the given skill.

One embodiment provides a computer implemented method wherein a difference between the first set of observable data conditions and the second set of observable data conditions accounts for style variances of human experts associated with the respective expert knowledge variations.

One embodiment provides a computer implemented method wherein a difference between the first set of observable data conditions and the second set of observable data conditions accounts for coaching advice derived from human experts associated with the respective expert knowledge variations.

One embodiment provides a computer implemented method wherein, for the selected set of one or more skills, there is a first selectable expert knowledge variation and a second selectable expert knowledge variation, wherein:

for the first selectable expert knowledge variation, the downloadable data configures the client device to provide a first set of feedback data to the user in response to observing defined observable data conditions associated with a given skill; and for the second selectable expert knowledge variation, the downloadable data configures the client device to provide a second different set of feedback data to the user in response to observing defined observable data conditions associated with a given skill.

One embodiment provides a computer implemented method wherein a difference between the first set of feedback data and the second set of feedback data accounts for coaching advice derived from human experts associated with the respective expert knowledge variations.

One embodiment provides a computer implemented method wherein a difference between the first set of feedback data and the second set of feedback includes different audio data representative of voices of human experts associated with the respective expert knowledge variations.

One embodiment provides a computer implemented method wherein the performance sensor units include a plurality of motion sensor units.

One embodiment provides a computer implemented method wherein the client device includes a POD device configured to process motion sensor data derived from the plurality of motion sensor units, wherein the wearable garment provides a plurality of sensor strands configured to facilitate delivery, to the POD device, of the motion sensor data.

One embodiment provides a computer implemented method wherein each of the plurality of sensor units include: an accelerometer, a magnetometer, and a gyroscope.

One embodiment provides a computer implemented method for generating data that is configured to enable the delivery of skills training content for a defined skill, the method including:

generating a first set of observable data conditions, wherein the first set includes observable data conditions configured to enable processing of input data derived from one or more performance sensor units, the input data being representative of a physical performance of the defined skill by a user, thereby to identify one or more attributes of the performance; and generating a second set of observable data conditions, wherein the second set includes observable data conditions configured to enable processing of input data derived from the same one or more performance sensor units, the input data being representative of a physical performance of the defined skill by a user, thereby to identify one or more attributes of the performance;

wherein the second set of observable data conditions includes one or more expert-specific observable data conditions that are absent from the first set of observable data conditions, wherein the one or more expert-specific observable data conditions are incorporated into of an expert knowledge variation of skills training content for the defined skill relative to skills training content generated using only the first set of observable data conditions.

One embodiment provides a computer implemented method wherein the expert knowledge variation of skills training content accounts for style variances associated with a particular human expert relative to a baseline skill performance style.

One embodiment provides a computer implemented method wherein the expert knowledge variation of skills training content accounts for coaching knowledge variances associated with a particular human expert relative to baseline coaching knowledge.

One embodiment provides a computer implemented method wherein the expert knowledge variation of skills training content includes: sensor configuration data, wherein the sensor configuration data includes data that configures a set of one or more performance sensor units to operate in a defined manner thereby to provide data representative of an attempted performance of a particular skill; state engine data, wherein the state engine data includes data that is configured to enable a processing device to identify attributes of the attempted performance of the particular skill based on the data provided by the set of one or more performance sensor units; and user interface data, wherein the user interface data includes data configured to enable operation of a user interface based on the identified attributes of the attempted performance of the particular skill.

One embodiment provides a computer implemented method wherein the performance sensor units include a plurality of motion sensor units.

One embodiment provides a computer implemented method wherein the expert knowledge variation of skills training content is executed, at least in part, on user hardware including a POD device configured to process motion sensor data derived from the plurality of motion sensor units, wherein the wearable garment provides a plurality of sensor strands configured to facilitate delivery, to the POD device, of the motion sensor data.

One embodiment provides a computer implemented method wherein each of the plurality of sensor units include: an accelerometer, a magnetometer, and a gyroscope.

One embodiment provides a computer implemented method wherein, for the defined skill, a cloud hosted marketplace is configured to make available for procurement by one or more users: (i) a standard version of skills training content; and (ii) the expert knowledge variation of skills training content.

One embodiment provides a computer implemented method for generating data that is configured to enable the delivery of skills training content for a defined skill, the method including:

generating a first set of skills training content, wherein the first set of skills training content is configured to enable delivery of a skills training program for the defined skill based on processing of input data derived from one or more performance sensor units, the input data being representative of a physical performance of the defined skill by a user, thereby to identify one or more attributes of the performance; and generating a second set of skills training content, wherein the second set of skills training content includes observable data conditions configured to enable processing of input data derived from the same one or more performance sensor units, the input data being representative of a physical performance of the defined skill by a user, thereby to identify one or more attributes of the performance;

wherein the second set of skills training content is configured to provide, in response to a given set of input data, a different training program effect as compared with the first set of skills training content in response to the same set of input data, such that the second set of skills training content provides an expert knowledge variation of skills training content.

One embodiment provides a computer implemented method wherein the expert knowledge variation of skills training content accounts for style variances associated with a particular human expert relative to a baseline skill performance style.

One embodiment provides a computer implemented method wherein the expert knowledge variation of skills training content accounts for coaching knowledge variances associated with a particular human expert relative to baseline coaching knowledge.

One embodiment provides a computer implemented method wherein the expert knowledge variation of skills training content includes: sensor configuration data, wherein the sensor configuration data includes data that configures a set of one or more performance sensor units to operate in a defined manner thereby to provide data representative of an attempted performance of a particular skill; state engine data, wherein the state engine data includes data that is configured to enable a processing device to identify attributes of the attempted performance of the particular skill based on the data provided by the set of one or more performance sensor units; and user interface data, wherein the user interface data includes data configured to enable operation of a user interface based on the identified attributes of the attempted performance of the particular skill.

One embodiment provides a computer implemented method wherein the performance sensor units include a plurality of motion sensor units.

One embodiment provides a computer implemented method wherein the expert knowledge variation of skills training content is executed, at least in part, on user hardware including a POD device configured to process motion sensor data derived from the plurality of motion sensor units, wherein the wearable garment provides a plurality of sensor strands configured to facilitate delivery, to the POD device, of the motion sensor data.

One embodiment provides a computer implemented method wherein each of the plurality of sensor units include: an accelerometer, a magnetometer, and a gyroscope.

One embodiment provides a computer implemented method wherein, for the defined skill, a cloud hosted marketplace is configured to make available for procurement by one or more users: (i) a standard version of skills training content; and (ii) the expert knowledge variation of skills training content.

One embodiment provides a computer implemented method wherein the first set of training content data is associated with a first set of observable data conditions, and wherein the second set of training content data is associated with a second set of observable data conditions, such that the second set of training content data is configured to identify one or more attributes of the performance that are not identified by the first set of training content data.

One embodiment provides a computer implemented method wherein the first set of training content data is associated with a first protocol for mapping symptoms to causes, and wherein the second set of training content data is associated with a second protocol for mapping symptoms to causes, such that the second set of training content data provides at least one expert-specific relationship between a symptom and a cause.

One embodiment provides a computer implemented method wherein the first set of training content data is associated with a first set media content, and wherein the second set of training content data is associated with a second set of media content, such that the second set of training content data is configured to provide media content personalised to a particular expert.

One embodiment provides a computer implemented method for enabling a user to configure local performance monitoring hardware devices to provide training data associated with a selected one of a plurality of experts, the method including:

providing an interface configured to enable a user of a client device to select a set of one or more skills to be trained;

enabling the user to select an expert knowledge variation for the selected one or more skills to be trained, wherein there are multiple expert knowledge variations available for the set of one or more skills to be trained;

following the user's selection of the set of one or more skills to be trained, and the expert knowledge variation for the selected one or more skills to be trained, enabling a download process that provides, to a client device associated with the user, downloadable data that configures the client device to:

(i) process data derived from a set of performance-monitoring sensors, thereby to analyse a physical performance of a given one of the skills by the user; and (ii) based on the analysis, via a user interface device, training data that is specific to the selected expert knowledge variation.

One embodiment provides a computer implemented method wherein, for the selected set of one or more skills, there is a first selectable expert knowledge variation and a second selectable expert knowledge variation, wherein:

for the first selectable expert knowledge variation, the downloadable data configures the client device to identify, in data derived from the set of performance analysis sensors, a first set of observable data conditions associated with a given skill; and for the second selectable expert knowledge variation, the downloadable data configures the client device to identify, in data derived from the set of performance analysis sensors, a second different set of observable data conditions associated with the given skill.

One embodiment provides a computer implemented method wherein a difference between the first set of observable data conditions and the second set of observable data conditions accounts for style variances of human experts associated with the respective expert knowledge variations.

One embodiment provides a computer implemented method wherein a difference between the first set of observable data conditions and the second set of observable data conditions accounts for coaching advice derived from human experts associated with the respective expert knowledge variations.

One embodiment provides a computer implemented method wherein, for the selected set of one or more skills, there is a first selectable expert knowledge variation and a second selectable expert knowledge variation, wherein:

for the first selectable expert knowledge variation, the downloadable data configures the client device to provide a first set of feedback data to the user in response to observing defined observable data conditions associated with a given skill; and for the second selectable expert knowledge variation, the downloadable data configures the client device to provide a second different set of feedback data to the user in response to observing defined observable data conditions associated with a given skill.

One embodiment provides a computer implemented method wherein a difference between the first set of feedback data and the second set of feedback data accounts for coaching advice derived from human experts associated with the respective expert knowledge variations.

One embodiment provides a computer implemented method wherein a difference between the first set of feedback data and the second set of feedback includes different audio data representative of voices of human experts associated with the respective expert knowledge variations.

One embodiment provides a computer implemented method wherein the performance analysis sensors include motion sensors.

One embodiment provides a computer implemented method wherein the client device includes a POD device configured to be carried by a wearable garment, wherein the wearable garment provides a plurality of sensor strands configured to enable delivery, to the POD device, of data derived from a plurality of sensor units carried by the wearable garment.

One embodiment provides a computer implemented method wherein each of the plurality of sensor units include: an accelerometer, a magnetometer, and a gyroscope.

One embodiment provides a system configured to enabling a user to configure local performance monitoring hardware devices to provide training data associated with a selected one of a plurality of experts, the system including:

a server that is configured to enable a client user interface device to interact with an interface configured to enable a user of a client device to select a set of one or more skills to be trained, wherein the interface is additionally configured to enable the user to select an expert knowledge variation for the selected one or more skills to be trained, wherein there are multiple expert knowledge variations available for the set of one or more skills to be trained;

a download manager component that is configured to, following the user's selection of the set of one or more skills to be trained, and the expert knowledge variation for the selected one or more skills to be trained, enable a download process that provides, to a client device associated with the user, downloadable data that configures the client device to:

(i) process data derived from a set of performance-monitoring sensors, thereby to analyse a physical performance of a given one of the skills by the user; and (ii) based on the analysis, via a user interface device, training data that is specific to the selected expert knowledge variation.

One embodiment provides a computer implemented method wherein, for the selected set of one or more skills, there is a first selectable expert knowledge variation and a second selectable expert knowledge variation, wherein:

for the first selectable expert knowledge variation, the downloadable data configures the client device to identify, in data derived from the set of performance analysis sensors, a first set of observable data conditions associated with a given skill; and for the second selectable expert knowledge variation, the downloadable data configures the client device to identify, in data derived from the set of performance analysis sensors, a second different set of observable data conditions associated with the given skill.

One embodiment provides a computer implemented method wherein a difference between the first set of observable data conditions and the second set of observable data conditions accounts for style variances of human experts associated with the respective expert knowledge variations.

One embodiment provides a computer implemented method wherein a difference between the first set of observable data conditions and the second set of observable data conditions accounts for coaching advice derived from human experts associated with the respective expert knowledge variations.

One embodiment provides a computer implemented method wherein, for the selected set of one or more skills, there is a first selectable expert knowledge variation and a second selectable expert knowledge variation, wherein:

for the first selectable expert knowledge variation, the downloadable data configures the client device to provide a first set of feedback data to the user in response to observing defined observable data conditions associated with a given skill; and for the second selectable expert knowledge variation, the downloadable data configures the client device to provide a second different set of feedback data to the user in response to observing defined observable data conditions associated with a given skill.

One embodiment provides a computer implemented method wherein a difference between the first set of feedback data and the second set of feedback data accounts for coaching advice derived from human experts associated with the respective expert knowledge variations.

One embodiment provides a computer implemented method wherein a difference between the first set of feedback data and the second set of feedback includes different audio data representative of voices of human experts associated with the respective expert knowledge variations.

One embodiment provides a computer implemented method wherein the performance analysis sensors include motion sensors.

One embodiment provides a computer implemented method wherein the client device includes a POD device configured to be carried by a wearable garment, wherein the wearable garment provides a plurality of sensor strands configured to enable delivery, to the POD device, of data derived from a plurality of sensor units carried by the wearable garment.

One embodiment provides a computer implemented method wherein each of the plurality of sensor units include: an accelerometer, a magnetometer, and a gyroscope.

One embodiment provides a method for enabling a user to configure local performance monitoring hardware devices to provide training data associated with a selected one of a plurality of experts, the method including:

providing an interface configured to enable a user of a client device to select a set of one or more skills to be trained;

enabling the user to select an expert knowledge variation for the selected one or more skills to be trained, wherein there are multiple expert knowledge variations available for the set of one or more skills to be trained;

following the user's selection of the set of one or more skills to be trained, and the expert knowledge variation for the selected one or more skills to be trained, enabling a download process that provides, to a client device associated with the user, downloadable data that configures the client device to:

(i) process data derived from a set of performance-monitoring sensors, thereby to analyse a physical performance of a given one of the skills by the user; and (ii) based on the analysis, via a user interface device, training data that is specific to the selected expert knowledge variation.

One embodiment provides a method wherein, for the selected set of one or more skills, there is a first selectable expert knowledge variation and a second selectable expert knowledge variation, wherein:

for the first selectable expert knowledge variation, the downloadable data configures the client device to identify, in data derived from the set of performance analysis sensors, a first set of observable data conditions associated with a given skill; and for the second selectable expert knowledge variation, the downloadable data configures the client device to identify, in data derived from the set of performance analysis sensors, a second different set of observable data conditions associated with the given skill.

One embodiment provides a method wherein a difference between the first set of observable data conditions and the second set of observable data conditions accounts for style variances of human experts associated with the respective expert knowledge variations.

One embodiment provides a method wherein a difference between the first set of observable data conditions and the second set of observable data conditions accounts for coaching advice derived from human experts associated with the respective expert knowledge variations.

One embodiment provides a method wherein, for the selected set of one or more skills, there is a first selectable expert knowledge variation and a second selectable expert knowledge variation, wherein:

for the first selectable expert knowledge variation, the downloadable data configures the client device to provide a first set of feedback data to the user in response to observing defined observable data conditions associated with a given skill; and for the second selectable expert knowledge variation, the downloadable data configures the client device to provide a second different set of feedback data to the user in response to observing defined observable data conditions associated with a given skill.

One embodiment provides a method wherein a difference between the first set of feedback data and the second set of feedback data accounts for coaching advice derived from human experts associated with the respective expert knowledge variations.

One embodiment provides a method wherein a difference between the first set of feedback data and the second set of feedback includes different audio data representative of voices of human experts associated with the respective expert knowledge variations.

One embodiment provides a method wherein the performance analysis sensors include motion sensors.

One embodiment provides a method wherein the client device includes a POD device configured to be carried by a wearable garment, wherein the wearable garment provides a plurality of sensor strands configured to enable delivery, to the POD device, of data derived from a plurality of sensor units carried by the wearable garment.

One embodiment provides a method wherein each of the plurality of sensor units include: an accelerometer, a magnetometer, and a gyroscope.

One embodiment provides a system configured to enabling a user to configure local performance monitoring hardware devices to provide training data associated with a selected one of a plurality of experts, the system including:

a server that is configured to enable a client user interface device to interact with an interface configured to enable a user of a client device to select a set of one or more skills to be trained, wherein the interface is additionally configured to enable the user to select an expert knowledge variation for the selected one or more skills to be trained, wherein there are multiple expert knowledge variations available for the set of one or more skills to be trained;

a download manager component that is configured to, following the user's selection of the set of one or more skills to be trained, and the expert knowledge variation for the selected one or more skills to be trained, enable a download process that provides, to a client device associated with the user, downloadable data that configures the client device to:

(i) process data derived from a set of performance-monitoring sensors, thereby to analyse a physical performance of a given one of the skills by the user; and (ii) based on the analysis, via a user interface device, training data that is specific to the selected expert knowledge variation.

One embodiment provides a system wherein, for the selected set of one or more skills, there is a first selectable expert knowledge variation and a second selectable expert knowledge variation, wherein:

for the first selectable expert knowledge variation, the downloadable data configures the client device to identify, in data derived from the set of performance analysis sensors, a first set of observable data conditions associated with a given skill; and for the second selectable expert knowledge variation, the downloadable data configures the client device to identify, in data derived from the set of performance analysis sensors, a second different set of observable data conditions associated with the given skill.

One embodiment provides a system wherein a difference between the first set of observable data conditions and the second set of observable data conditions accounts for style variances of human experts associated with the respective expert knowledge variations.

One embodiment provides a system wherein a difference between the first set of observable data conditions and the second set of observable data conditions accounts for coaching advice derived from human experts associated with the respective expert knowledge variations.

One embodiment provides a system wherein, for the selected set of one or more skills, there is a first selectable expert knowledge variation and a second selectable expert knowledge variation, wherein:

for the first selectable expert knowledge variation, the downloadable data configures the client device to provide a first set of feedback data to the user in response to observing defined observable data conditions associated with a given skill; and for the second selectable expert knowledge variation, the downloadable data configures the client device to provide a second different set of feedback data to the user in response to observing defined observable data conditions associated with a given skill.

One embodiment provides a system wherein a difference between the first set of feedback data and the second set of feedback data accounts for coaching advice derived from human experts associated with the respective expert knowledge variations.

One embodiment provides a system wherein a difference between the first set of feedback data and the second set of feedback includes different audio data representative of voices of human experts associated with the respective expert knowledge variations.

One embodiment provides a system wherein the performance analysis sensors include motion sensors.

One embodiment provides a system wherein the client device includes a POD device configured to be carried by a wearable garment, wherein the wearable garment provides a plurality of sensor strands configured to enable delivery, to the POD device, of data derived from a plurality of sensor units carried by the wearable garment.

One embodiment provides a system wherein each of the plurality of sensor units include: an accelerometer, a magnetometer, and a gyroscope.

One embodiment provides a wearable garment including: a plurality of sensor strands, wherein each sensor strand includes one or more sensor units, wherein each sensor unit includes: (i) a microprocessor; (ii) a memory module; and (iii) a set of one or more motion sensor components; a sensor strand connection port, wherein the sensor strand connection port is configured to couple a plurality of sensor strands to a central processing device; and a central processing device, the sensor processing unit including (i) a power supply; (ii) a microprocessor; and (iii) a memory module; wherein the memory module is configured to store software instructions executable by the microprocessor that enable the processing device to identify one or more sets of predefined observable data conditions in sensor data, including sensor data received by the central processing device from the plurality of connected sensor units.

One embodiment provides a wearable garment including: a plurality of sensor strands, wherein each sensor strand includes one or more mounting locations, each mounting location configured to enable connection and mounting of a respective sensor unit, wherein each sensor unit includes: (i) a microprocessor; (ii) a memory module; and (iii) a set of one or more motion sensor components; a sensor strand connection port, wherein the sensor strand connection port is configured to couple a plurality of sensor strands to a central processing device; and a mounting location configured to enable connection and mountain of a central processing device, the sensor processing unit including (i) a power supply; (ii) a microprocessor; and (iii) a memory module; wherein the memory module is configured to store software instructions executable by the microprocessor that enable the processing device to identify one or more sets of predefined observable data conditions in sensor data, including sensor data received by the central processing device from the plurality of sensor units.

One embodiment provides a computer program product for performing a method as described herein.

One embodiment provides a non-transitory carrier medium for carrying computer executable code that, when executed on a processor, causes the processor to perform a method as described herein.

One embodiment provides a system configured for performing a method as described herein.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the invention will now be described, by way of example only, with reference to the accompanying drawings in which:

FIG. 4A illustrates an example data collection table.

FIG. 4B illustrates an example data collection table.

DETAILED DESCRIPTION

Figure 1A:
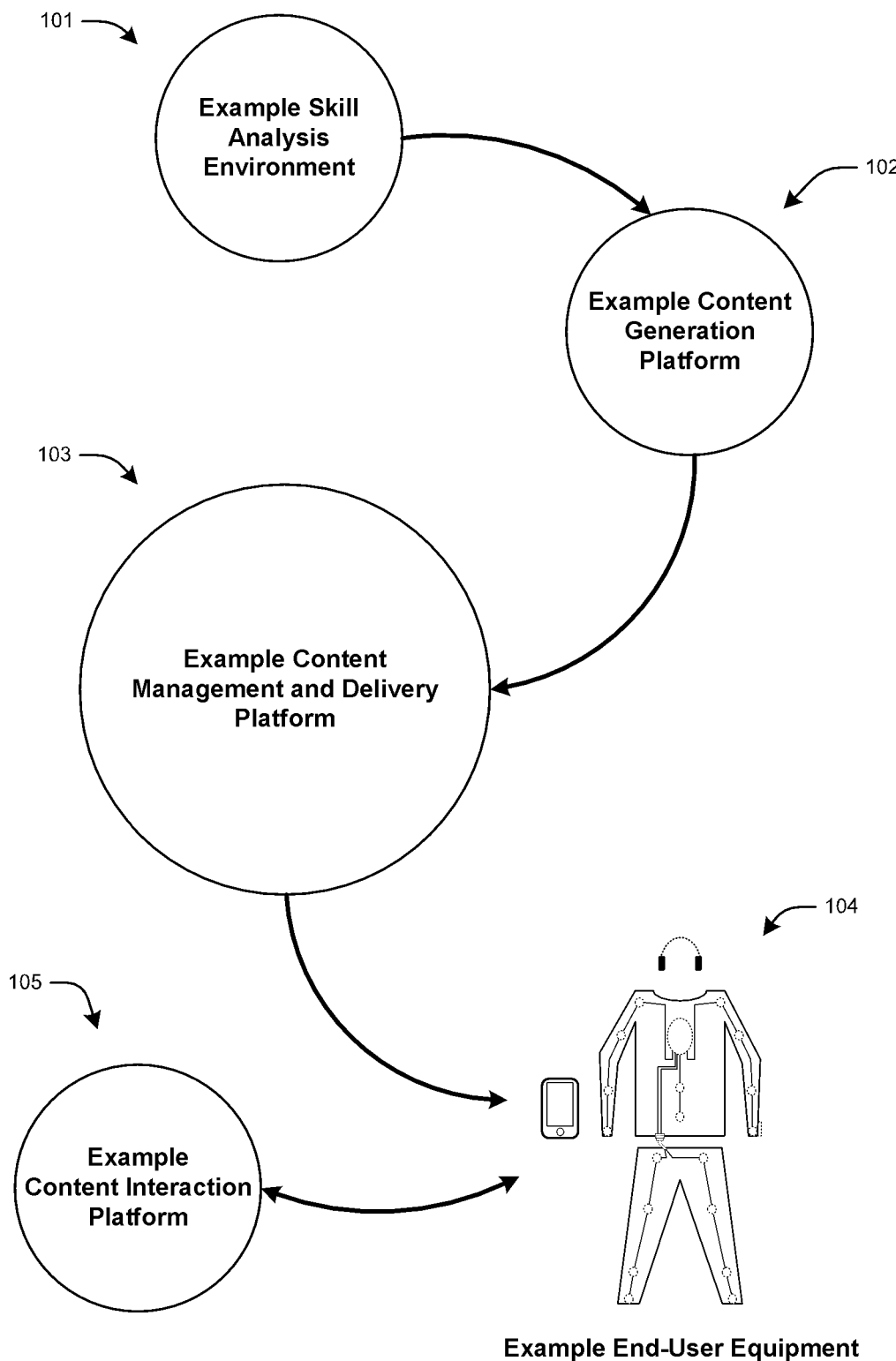
FIG. 1A schematically illustrates a framework configured to enable generation and delivery of content according to one embodiment.

Embodiments described herein relate to technological frameworks whereby user skill performances are monitored using Performance Sensor Units (PSUs), and data derived from those PSUs is processed thereby to determine attributes of the user skill performances. For example, attributes of performances are used to drive computer programs, such as computer programs configured to provide skills training. In other embodiments attributes of performances are determined for alternate purposes, such as providing multi-user competitive activities and the like.

In the context of skills training, the frameworks described herein make use of PSUs to collect data representative of performance attributes, and provide feedback and/or instruction to a user thereby to assist in that user improving his/her performance. For instance, this may include providing coaching advice, directing the user to perform particular exercises to develop particular required underlying sub-skills, and the like. By monitoring performances substantially in real-time via PSUs, a training program is able to adapt based on observation of whether a user's performance attributes improve based on feedback/instruction provided. For example, observation of changes in performance attributes between successive performance attempt iterations are indicative of whether the provided feedback/instruction has been successful or unsuccessful. This enables the generation and delivery of a wide range of automated adaptive skills training programs.

The nature of the skill performances vary between embodiments, however the following two general categories are used for the purpose of examples considered herein:

Human motion-based skill performances. These are performances where human motion attributes are representative of defining characteristics of a skill. For example, motion-based performances include substantially any physical skill which involves movement of the performer's body. A significant class of motion-based performances are performances of skills that are used in sporting activities.

Audio-based skill performances. These are performances where audibly-perceptible attributes are representative of defining characteristics of a skill. For example, audio-based performances include musical and/or linguistic performances. A significant class of audio-based performances are performances of skills associated with playing musical instruments.

Although the examples provided below focus primarily on the comparatively more technologically challenging case of motion-based skills performances, it will be appreciated that principles applied in respect of motion-based skills are readily applied in other situations. For example, the concept of using Observable Data Conditions (ODCs) in data received from PSUs is applicable equally between motion, audio, and other forms of performances.

Some embodiments relate to computer-implemented frameworks that enable the defining, distribution and implementation of content that is experienced by end-users in the context of performance monitoring. This includes content that is configured to provide interactive skills training to a user, whereby a user's skill performance is analysed by processing of Performance Sensor Data (PSD) derived from one or more PSUs that are configured to monitor a skill performance by the user.

Various embodiments are described below by reference to an overall end-to-end framework. The overall framework is described to provide context to its constituent parts, of which some are able to be applied in different contexts. Although only subset of aspects of the overall described end-to-end framework are directly claimed in the claims below, it should be appreciated that inventive subject matter resides across a wide range of the constituent components (even if not specifically identified as such). For example, inventive subject matter is embodied across aspects of the technologies and methodologies described herein, including but not limited to: (i) analysis of a skill thereby to understand its defining characteristics; (ii) defining of protocols thereby to enable automated analysis of a skill using one or more PSUs; (iii) defining and delivery of content that makes use of the automated analysis thereby to provide interactive end-use content, such as skills training; (iv) adaptive implementation of skills training programs; (v) hardware and software that facilitates the delivery of content to end users; (vi) hardware and software that facilitates the experiencing of content by end users; and (vii) technology and methodologies developed to facilitate the configuration and implementation of multiple motion sensor units for the purpose of human activity monitoring.

Terminology

For the purpose of embodiments described below, the following terms are used:

Performance Sensor Unit (PSU). A performance sensor unit is a hardware device that is configured to generate data in response to monitoring of a physical performance. Examples of sensor units configured to process motion data and audio data are primarily considered herein, although it should be appreciated that those are by no means limiting examples.

Performance Sensor Data (PSD). Data delivered by a PSU is referred to as Performance Sensor Data. This data may comprise full raw data from a PSU, or a subset of that data (for example based on compression, reduced monitoring, sampling rates, and so on).

Audio Sensor Unit (ASU). An audio sensor unit is a category of PSU, being a hardware device that is configured to generate and transmit data in response to monitoring of sound. In some embodiments an ASU is configured to monitor sound and/or vibration effects, and translate those into a digital signal (for example a MIDI signal). One example is an ASU is a pickup device including a transducer configured to capture mechanical vibrations in a stringed instrument and concert those into electrical signals.

Audio Sensor Data (ASD). This is data delivered by one or more ASUs.

Motion Sensor Unit (MSU). A motion sensor unit is a category of PSU, being a hardware device that is configured to generate and transmit data in response to motion. This data is in most cases defined relative to a local frame of reference. A given MSU may include one or more accelerometers; data derived from one or more magnetometers; and data derived from one or more gyroscopes. A preferred embodiment makes use of one or more 3-axis accelerometers, one 3-axis magnetometer, and one 3-axis gyroscope. A motion sensor unit may be "worn" or "wearable", which means that it is configured to be mounted to a human body in a fixed position (for example via a garment).

Motion Sensor Data (MSD). Data delivered by a MSU is referred to as Motion Sensor Data (MSD). This data may comprise full raw data from a MSU, or a subset of that data (for example based on compression, reduced monitoring, sampling rates, and so on).

MSU-enabled garment. A MSU enabled garment is a garment (such as a shirt or pants) that is configured to carry a plurality of MSUs. In some embodiments, the MSUs are mountable in defined mountain zones formed in the garment (preferably in a removable manner, such that individual MSUs are able to be removed and replaced), and coupled to communication lines.

POD Device. A POD device is a processing device that receives PSD (for example MSD from MSUs). In some embodiments it is carried by a MSU-enabled garment, and in other embodiments it is a separate device (for example in one embodiment the POD device is a processing device that couples to a smartphone, and in some embodiments POD device functionality is provided by a smartphone or mobile device). The MSD is received in some cases via wired connections, in some cases via wireless connections, and in some cases via a combination of wireless and wired connections. As described herein, a POD device is responsible for processing the MSD thereby to identify data conditions in the MSD (for example to enable identification of the presence of one or more symptoms). In some embodiments the role of a POD device is performed in whole or in part by a multi-purpose end-user hardware device, such as a smartphone. In some embodiments at least a portion of PSD processing is performed by a cloud-based service.

Motion Capture Data (MCD). Motion capture data (MCD) is data derived from using any available motion capture technique. In this regard, "motion capture" refers to a technique whereby capture devices are used to capture data representative of motion, for example using visual markers mounted to a subject at known locations. An example is motion capture technology provided by Vicon (although no affiliation between the inventors/applicant and Vicon is to be inferred). As discussed further below, MCD is preferably used to provide a link between visual observation and MSD observation.

Skill. In the context of a motion-based activity, a skill is an individual motion (or set of linked motions) that is to be observed (visually and/or via MSD), for example in the context of coaching. A skill may be, for example, a rowing motion, a particular category of soccer kick, a particular category of golf swing, a particular acrobatic manoeuvre, and so on. Reference is also made to "sub-skills". This is primarily to differentiate between a skill being trained, and lesser skills that form part of that skill, or are building blocks for that skill. For example, in the context of a skill in the form of juggling, a sub-skill is a skill that involves throwing a ball and catching it in the same hand.

Symptom. A symptom is an attribute of a skill that is able to be observed (for example observed visually in the context of initial skill analysis, and observed via processing of MSD in the context of an end-user environment). In practical terms, a symptom is an observable motion attribute of a skill, which is associated with a meaning. For example, identification of a symptom may trigger action in delivery of an automated coaching process. A symptom may be observable visually (relevant in the context of traditional coaching) or via PSD (relevant in the context of delivery of automated adaptive skills training as discussed herein).

Cause. Symptoms are, at least in some cases, associated with one causes (for example a given symptom may be associated with one or more causes). A cause is also in some cases able to be observed in MSD, however that is not necessarily essential. From a coaching perspective, one approach is to first identify a symptom, and then determine/predict a cause for that symptom (for example determination may be via analysis of MSD, and prediction may be by means other than analysis of MSD). Then, the determined/predicted cause may be addressed by coaching feedback, followed by subsequent performance assessment thereby to determine whether the coaching feedback was successful in addressing the symptom.

Observable Data Condition (ODC). The term Observable Data Condition is used to describe conditions that are able to be observed in PSD, such as MSD (typically based on monitoring for the presence of an ODC, or set of anticipated ODCs) thereby to trigger downstream functionalities. For example, an ODC may be defined for a given symptom (or cause); if that ODC is identified in MSD for a given performance, then a determination is made that the relevant symptom (or cause) is present in that performance. This then triggers events in a training program.

Training Program. The term "training program" is used to describe an interactive process delivered via the execution of software instructions, which provides an end user with instructions of how to perform, and feedback in relation to how to modify, improve, or otherwise adjust their performance. In at least some embodiments described below, the training program is an "adaptive training program", being a training program that executes on the basis of rules/logic that enable the ordering of processes, selection of feedback, and/or other attributes of training to adapt based on analysis of the relevant end user (for example analysis of their performance and/or analysis of personal attributes such as mental and/or physical attributes).

As described in more detail below, from an end-user product perspective some embodiments employ a technique whereby a POD device is configured to analyse a user's PSD (such as MSD) in respect of a given performance thereby to determine presence of one or more symptoms, being symptoms belonging to a set defined based on attributes of the user (for example the user's ability level, and symptoms that the user is known to display from analysis of previous iterations). Once a symptom is identified via the MSD, a process is performed thereby to determine/predict a cause. Then, feedback is selected thereby to seek to address that cause. In some embodiments complex selection processes are defined thereby to select specific feedback for the user, for example based on (i) user history, for example prioritising untried or previously successful feedback over previously unsuccessful feedback; (ii) user learning style; (iii) user attributes, for example mental and/or physical state at a given point in time, and/or (iv) a coaching style, which is in some cases based on the style of a particular real-world coach.

Example End-to-End Frameworks

FIG. 1A provides a high-level overview of an end-to-end framework which is leveraged by a range of embodiments described herein. In the context of FIG. 1A, an example skill analysis environment 101 is utilised thereby to analyse one or more skills, and provide data that enables the generation of end user content in relation to those skills. For instance, this in some embodiments includes analysing a skill thereby to determine ODCs that are able to be identified by PSUs (preferably ODCs that are associated with particular symptoms, causes, and the like). These ODCs are able to be utilised within content generation logic implemented by an example content generation platform 102 (such as a training program). In that regard, generating content preferably includes defining a protocol whereby prescribed actions are taken in response to identification of specific ODCs.

A plurality of skill analysis environments and content generation platforms are preferably utilised thereby to provide content to an example content management and delivery platform 103. This platform is in some embodiments defined by a plurality of networked server devices. In essence, the purpose of platform 103 is to make available content generated by content generation platforms to end users. In the context of FIG. 1A, that includes enabling download of content to example end-user equipment 104. The downloading in some embodiments includes an initial download of content, and subsequently further downloads of additional required content. The nature of the further downloads is in some cases affected by user interactions (for instance based on an adaptive progression between components of a skills training program and/or user selections).

Example equipment 104 is illustrated in the form of a MSU-enabled garment that carries a plurality of MSUs and a POD device, in conjunction with user interface devices (such as a smartphone, a headset, HUD eyewear, retinal projection devices, and so on).

In the example of FIG. 1A, a user downloads content from platform 103, and causes that content to be executed via equipment 104. For instance, this may include content that provides an adaptive skills training program for a particular physical activity, such as golf or tennis. In this example, equipment 104 is configured to interact with an example content interaction platform 105, being an external (e.g. web-based) platform that provides additional functionality relevant to the delivery of the downloaded content. For instance, various aspects of an adaptive training program and/or its user interface may be controlled by server-side processing. In some cases platform 105 is omitted, enabling equipment 104 to deliver previously downloaded content in an offline mode.

Figure 14:
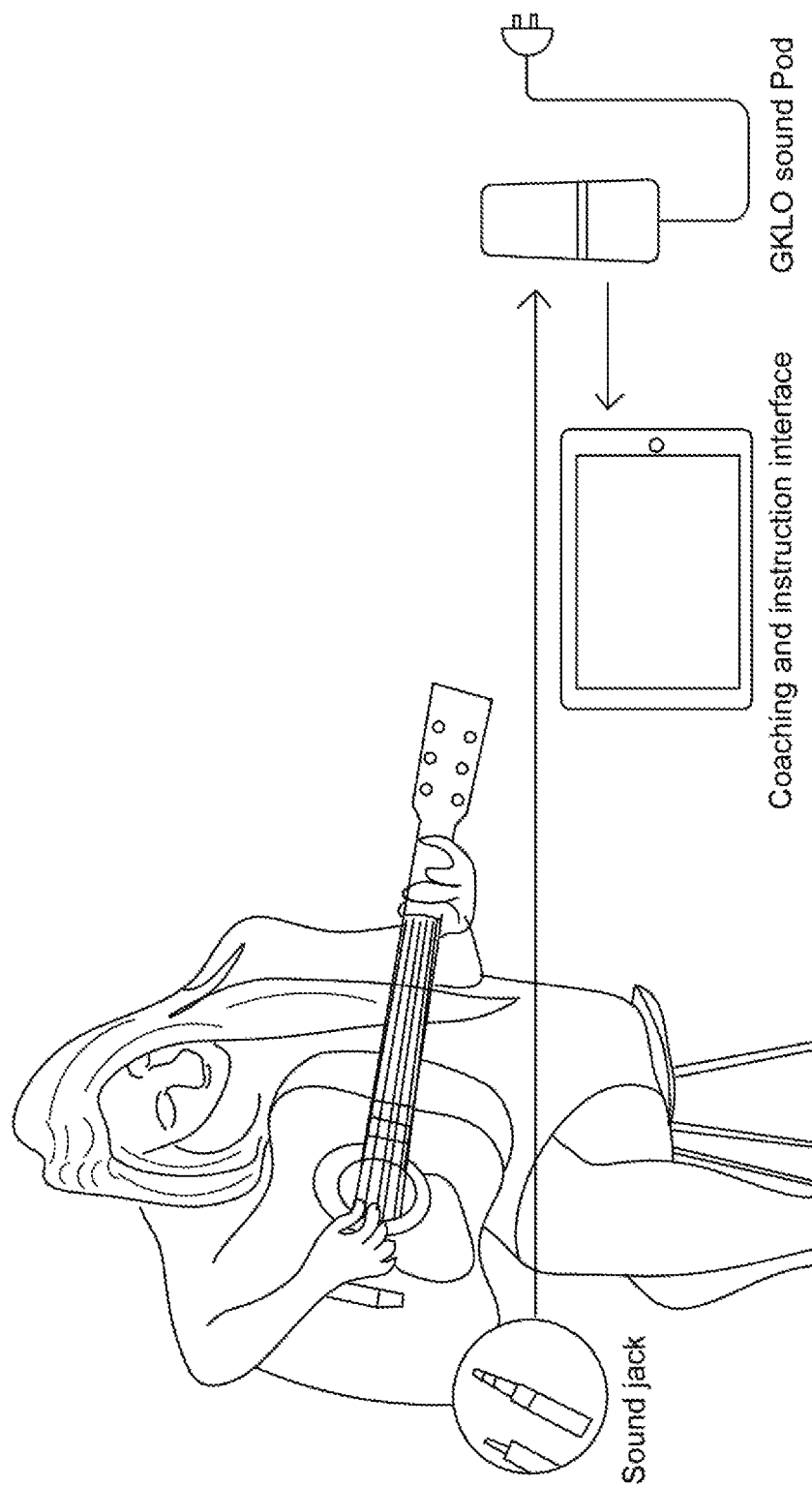
FIG. 14 illustrates a guitar tuition arrangement according to one embodiment.
Figure 15:
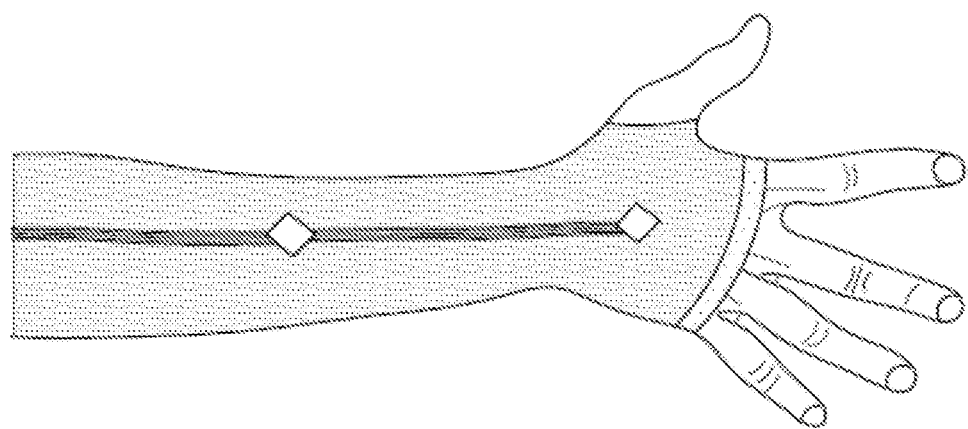
FIG. 15 illustrates a portion of an example MSU-enabled garment.

By way of general illustration, the following specific examples of content are provided:

A guitar training program. A user downloads a guitar training program that is configured to provide training in respect of a given piece of music. A PSU in the form of a pickup is used, thereby to enable analysis of PSD representative of the user's playing of a guitar. The training program is driven based on analysis of that PSD, thereby to provide the user with coaching. For example, the coaching may include tips for finger positioning, remedial exercises to practice progression between certain finger positions, and/or suggestion of other content (e.g. alternate pieces of music) that may be of interest and/or assistance to the user. An example is illustrated in FIG. 14 (showing a sound jack in lieu of a pickup, in combination with a POD device which processes audio data and a tablet device that delivers user interface data).

A golf training program. A user downloads a golf training program, which is configured to operate with a MSU-enabled garment. This includes downloading of sensor configuration data and state engine data to a POD device provided by the MSU-enabled garment. The user is instructed to perform a performance defined certain form of swing (for example with a certain intensity, club, or the like) and plurality of MSUs carried by the MSU-enabled garment provide MSD representative of the performance. The MSD is processed thereby to identify symptoms and/or causes, and training feedback is provided. This is repeated for one or more further performance iterations, based on training program logic designed to assist the user in improving his/her form. Instructions and/or feedback are provided by way of a retinal display projector which delivers user interface data directly into the user's field of vision.

It will be appreciated that these are examples only.

Figure 1B:
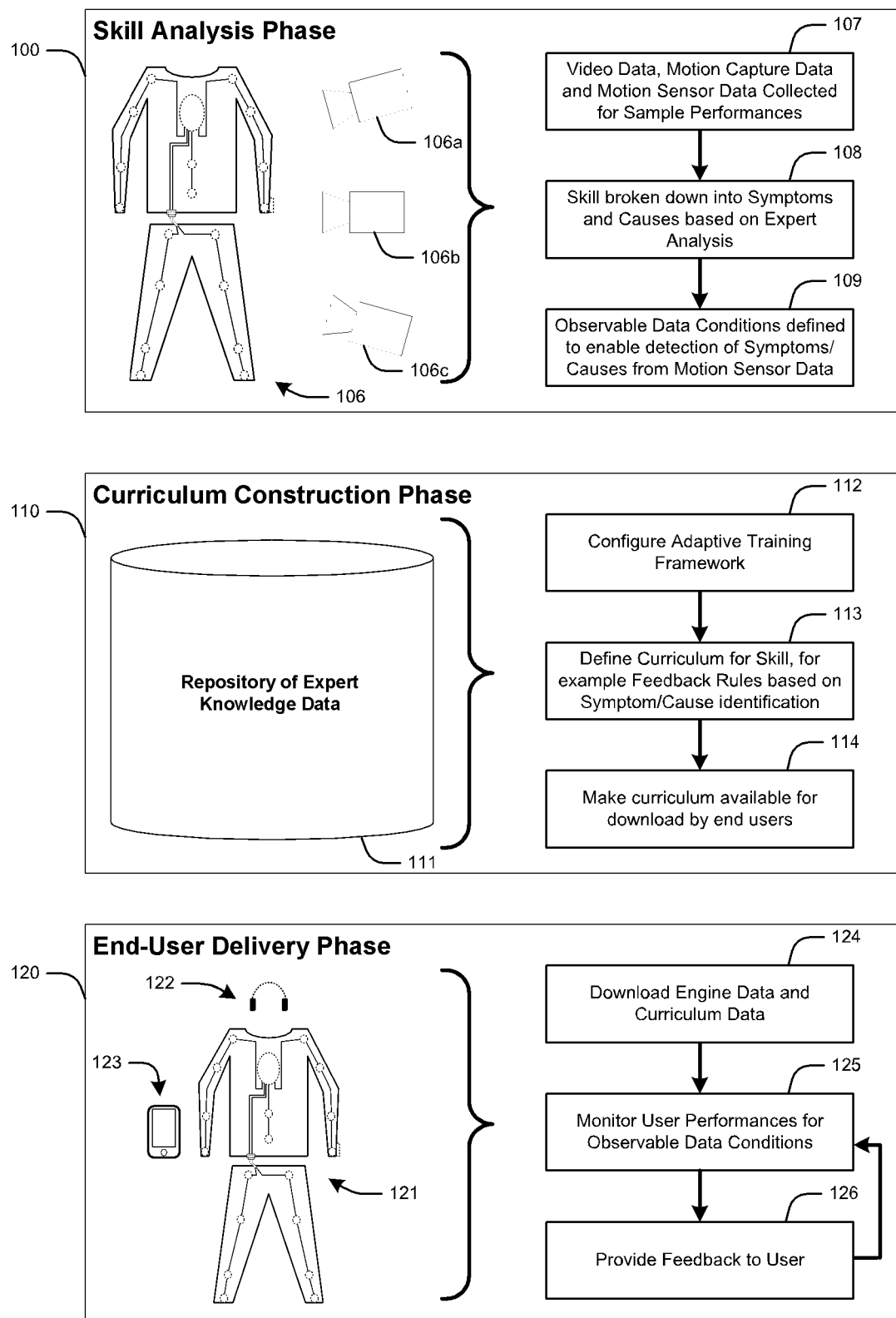
FIG. 1B schematically illustrates a framework configured to enable generation and delivery of content according to a further embodiment.

FIG. 1B provides a more detailed overview of a further example end-to-end technological framework that is present in the context of some embodiments. This example is particularly relevant to motion-based skills training, and is illustrated by reference to a skill analysis phase 100, a curriculum construction phase 110, and an end user delivery phase 120. It will be appreciated that this is not intended to be a limiting example, and is provide to demonstrate a particular end-to-end approach for defining and delivering content.

In the context of skill analysis phase 100, FIG. 1 illustrates a selection of hardware used at that stage in some embodiments, being embodiments where MCD is used to assist in analysis of skills, and subsequently to assist and/or validate determination of ODCs for MSD. The illustrated hardware is a wearable sensor garment 106 which carries a plurality of motion sensor units and a plurality of motion capture (mocap) markers (these are optionally located at similar positions on the garment), and a set of capture devices 106*a*-106*c*. There may be a lesser or greater number of capture devices, including capture devices configured for motion capture application, and/or camera devices configured for video capture application. In some embodiments a given capture device is configured for both applications. A set of example processes are also illustrated. Block 107 represents a process including capturing of video data, motion capture data (MCD), and motion sensor data (MSD) for a plurality of sample performances. This data is used by processes represented in block 108, which include breaking down a skill into symptoms and causes based on expert analysis (for example including: analysis of a given skill, thereby to determine aspects of motion that make up that skill and affect performance, preferably at multiple ability levels; and determination of symptoms and causes for a given skill, including ability level specific determination of symptoms and causes for a given skill). Block 109 represents a process including defining of ODCs to enable detection of symptoms/causes from motion sensor data. These ODCs are then available for use in subsequent phases (for example they are used in a given curriculum, applied in state engine data, and the like).

Although phase 100 is described here by reference to an approach that makes use of MCD, that is not intended to be a limiting example. Various other approaches are implemented in further embodiments, for example: approaches that make use of MSD from the outset (e.g. there is no need to make use of MCD to assist and/or validate determination of ODCs for MSD), approaches that make use of machine learning of skills, and so on.

Phase 110 is illustrated by reference to a repository of expert knowledge data 111. For example, one or more databases are maintained, these containing information defined subject to aspects of phase 101 and/or other research and analysis techniques. Examples of information include: (i) consensus data representative of symptoms/causes; (ii) expert-specific data representative of symptoms/causes; (iii) consensus data representative of feedback relating to symptoms/causes; (iv) expert-specific data representative of feedback relating to symptoms/causes; and (v) coaching style data (which may include objective coaching style data, and personalised coaching style data). This is a selection only.

In the example of FIG. 1B, the expert knowledge data is utilised in the delivery of training programs in respect of skills analysed at phase 100. Block 112 represents a process including configuring an adaptive training framework. In this regard, in the example of FIG. 1B, a plurality of skills training programs, relating to respective skills and aspects thereof, are delivered via a common adaptive training framework. This is preferably a technological framework that is configured enable the generation of skill-specific adaptive training content that leverages underlying skill-nonspecific logic. For example, such logic relates to methodologies for: predicting learning styles; tailoring content delivery based on available time; automatically generating a lesson plan based on previous interactions (including refresher teaching of previously learned skills); functionally to recommend additional content to download; and other functionalities. Block 113 represents a process including defining of a curriculum for a skill. This may include defining a framework of rules for delivering feedback in response to identification of particular symptoms/causes. The framework is preferably an adaptive framework, which provides intelligent feedback based on acquired knowledge specific to an individual user (for example knowledge of the user's learning style, knowledge of feedback that has been successful/unsuccessful in the past, and the like). Block 114 represents a process including making a curriculum available for download by end users, for example making it available via an online store. As detailed further below, a given skill may have a basic curriculum offering, and/or one or more premium curriculum offerings (preferably at different price points). By way of example, a basic offering is in some embodiments based upon consensus expert knowledge, and a premium offering based on expert-specific expert knowledge.

In the case of phase 130, example end-user equipment is illustrated. This includes a MSU-enabled garment arrangement 121, comprising a shirt and pants carrying a plurality of MSUs, with a POD device provided on the shirt. The MSUs and POD device are configured to be removable from the garments, for example to enable cleaning and the like. A headset 122 is connected by Bluetooth (or other means) to the POD device, and configured to deliver feedback and instructions audibly to the user. A handheld device 123 (such as an iOS or Android smartphone) is configured to provide further user interface content, for example instructional videos/animations and the like. Other user interface devices may be used, for example devices configured to provide augmented reality information (such as displays viewable via wearable eyewear and the like).

A user of the illustrated end-user equipment downloads content for execution (for example from platform 103), thereby to engage in training programs and/or experience other forms of content that leverage processing of MSD. For example, this may include browsing an online store or interacting with a software application thereby to identify desired content, and subsequently downloading that content. In the illustrated embodiment content is downloaded to the POD device, the content including state engine data and curriculum data. The former includes data that enables the POD device to process MSD, thereby to identify symptoms (and/or perform other forms of motion analysis). The latter includes data required to enable provision of a training program, including content that is delivered by the user interface (for example instructions, feedback, and the like) and instructions for the delivery of that content (such as rules for the delivery of an adaptive learning process). In some embodiments engine data and/or curriculum data is obtained from a remote server on an ongoing basis.

Functional block 125 represents a process whereby the POD device performs a monitoring function, whereby a user performance is monitored for ODCs as defined in state engine data. For example, a user is instructed via device 123 and/or headset 122 to "perform activity X", and the POD device then processes the MSD from the user's MSUs thereby to identify ODCs associated with activity X (for example to enable identification of symptoms an/or causes). Based on the identification of ODCs and the curriculum data (and in some cases based on additional inputs), feedback is provided to the user via device 123 and/or headset 122 (block 126). For example, whilst repeatedly performing "activity X", the user is provided audible feedback with guidance on how to modify their technique. This leads into a looped process (for example a looped process referred to herein as a "try loop"), whereby feedback is provided and the effects monitored (for example by observing a change in the ODCs derived from MSD on subsequent performance iterations). The curriculum data in some embodiments is configured to adapt the feedback and/or stages of a training program based on a combination of (i) success/failure of feedback to achieve desired results in terms of activity improvement; and (ii) attributes of the user, such as mental and/or physical performance attributes.

Skill Analysis Phase—Overview

As noted, in some embodiments a skill analysis phase is implemented thereby to analyse a skill that is to be observed in the end-user delivery phase. More specifically, the skill analysis phase preferably includes analysis to: (i) determine attributes of a skill, for example attributes that are representative of the skill being performed (which is particularly relevant where the end user functionality includes skill identification), and attributes that are representative of the manner in which a skill is performed, such as symptoms and causes (which are particularly relevant where end user functionality includes skill performance analysis, for instance in the context of delivery of skills training); and (ii) define ODCs that enable automated identification of skill attributes (such as the skill being performed, and attributes of the performance of that skill such as symptoms and/or causes) such that end user hardware (PSUs, such as MSUs) is able to be configured for automated skill performance analysis.

The nature of the skill analysis phase varies significantly depending on the nature of a given skill (for example between the categories of motion-based skills and audio-based skills). For the sake of example, exemplary embodiments are now described in relation to a skill analysis phase in the context of a motion-based skill. That is, embodiments are described by reference to analysing a physical activity, thereby to determine ODCs that are used to configure a POD device that monitors data from body-mounted MSUs. This example is selected to be representative of a skill analysis phased in a relatively challenging and complex context, where various novel and inventive technological approaches have been developed to facilitate the task of generating effective ODCs for motion-based skills. It will be appreciated that not all aspects of the methodologies described herein are present in all embodiments, or used in the context of all activities. The technology is applicable to a wide range of physical activities, with varying levels of complexity (for example in terms of performance, coaching, and monitoring). However, methodologies described herein are applicable across a wide range of activities, for example skills performed in the context of individual and team sports.

The methodologies and technology detailed below are described by reference to specific examples relating to a particular physical activity (i.e. a particular skill): rowing. Rowing has been selected as an example primarily for the purposes of convenient textual explanation, and it will readily be appreciated how techniques described by reference to that particular activity are readily applied to other activities (for example performing a particular form of kick of a soccer ball, swinging a golf club, performing an acrobatic manoeuvre on a snowboard, and so on).

In general terms, there are a wide range of approaches for determining ODCs for a given physical activity. These include, but are not limited to, the following:

Utilisation of secondary technologies, thereby to streamline understanding of MSD. For example, examples provided below discuss an approach that utilises combination of MCD and MSD. MCD is used primarily due to the established nature of motion capture technology (for example using powerful high speed cameras); motion sensor technology on the other hand is currently continually advancing in efficacy. The use of well-established MCD analysis technology assists in understanding and/or validating MSD and observations made in respect of MSD.

Direct utilisation of MSD, without MCD assistance. For instance, MSD is utilised in a similar manner to MCD, in the sense of capturing data thereby to generate three dimensional body models similar to those conventionally generated from MCD (for example based on a body avatar with skeletal joints) It will be appreciated that this assumes a threshold degree of accuracy and reliability in MCD. However, in some embodiments this is able to be achieved, hence rendering MCD assistance unnecessary.

Machine learning methods, for example where MSD and/or MCD is collected for a plurality of sample performances, along with objectively defined performance outcome data (for example, in the case or rowing: power output; and in the case of golf: ball direction and trajectory). Machine learning method are implemented thereby to enable automated defining of relationships between ODCs and effects on skill performance. Such an approach, when implemented with a sufficient sample size, enables computer identification of ODCs to drive prediction of skill performance outcome. For example, based on machine learning of golf swing motions using sample performance collection of MSD (or, in some embodiments, MCD), ODCs that affect swing performance are automatically identified using analysis of objectively defined outcomes, thereby to enable reliable automated prediction of an outcome in relation to an end-user swing using end-user hardware (for example a MSU-enabled garment).

Remote collection of analysis data from end users. For example, end user devices are equipped with a "record" function, which enables recording of MSD representative of a particular skill as respectively performed by the end users (optionally along with information regarding symptoms and the like identified by the users themselves). The recorded data is transmitted to a central processing location to compare the MSD for a given skill (or a particular skill having a particular symptom) for a plurality of users, and hence identify ODCs for the skill (and/or symptom). For example, this is achieved by identifying commonalities in the data.

Other approaches may also be used, including other approaches that make use of non-MSD data to validate and/or otherwise assist MSD data, and also including other approaches that implement different techniques for defining and analysing a sample user group.

The first example above is considered in more detail below, by reference to specific example embodiments which are directed to enabling subjective expert coaching knowledge to contribute towards the development of ODCs for symptoms and/or causes that are able to be used in the context of skills training programs.

Skill Analysis Phase—Sample Analysis Example

In some example embodiments, for each skill to be trained, there is a need to perform initial analysis of the motions involved in that skill, using one or more sample skill performers, thereby to enable determination of differences between optimal performance and sub-optimal performance (and hence enable coaching towards optimal performance). In general terms, this begins with visual analysis, which is subsequently translated (via one or more intermediary processes) into analysis of motion sensor data (referred to as monitoring for Observable Data Conditions, or ODCs).

The example techniques described herein include obtaining data representative of physical skill performances (for a given skill) by a plurality of sample subjects. For each physical skill performance, the data preferably includes:

(i) Video data, captured by one or more capture devices from one or more capture angles. For example, in the context of rowing, this may include a side capture angle and a rear capture angle.

(ii) Motion capture data (MCD), using any available motion capture technique. In this regard, "motion capture" refers to a technique whereby capture devices are used to capture data representative of motion, for example using visual markers mounted to a subject at known locations. An example is motion capture technology provided by Vicon (although no affiliation between the inventors/applicant and Vicon is to be inferred).

(iii) Motion sensor data (MSD), using one or more body-mounted motion sensors.

In each case, a preferred approach is to store both (i) raw data, and (ii) data that has been subjected to a degree of processing. This is particularly the case for motion sensor data; raw data may be re-processed over time as newer/better processing algorithms become available thereby to enhance end-user functionality.

In overview, the general concept is to use the MCD as a stepping stone between video data (which is most useful to real-world coaches) and MSD (which is required for the ultimate end-user functionality, which involves coaching via analysis of data derived from a MSU-enabled garment). MCD presents a useful stepping stone in this regard, as (i) it is a well-developed and reliable technology; and (ii) it is well-suited to monitor the precise relative motions of body parts.

Figure 2A:
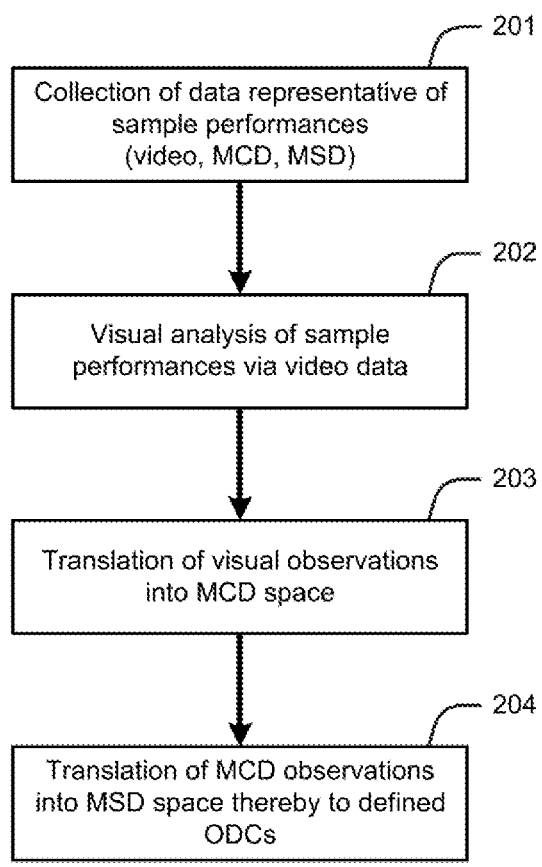
FIG. 2A illustrates a skill analysis method according to one embodiment.

The overall technique includes the following phases: (i) collection of data representative of sample performances by the selected subjects; (ii) visual analysis of sample performances by one or more coaches using video data; (iii) translation of visual observations made by the one or more coaches into the MCD space; and (iv) analysing the MSD based on the MCD observations thereby to identify ODCs in the MSD space that are, in a practical sense, representative of the one or more coaches' observations. Each of these phases is discussed in more detail below. This is illustrated in FIG. 2A via blocks 201 to 204.

Figure 2B:
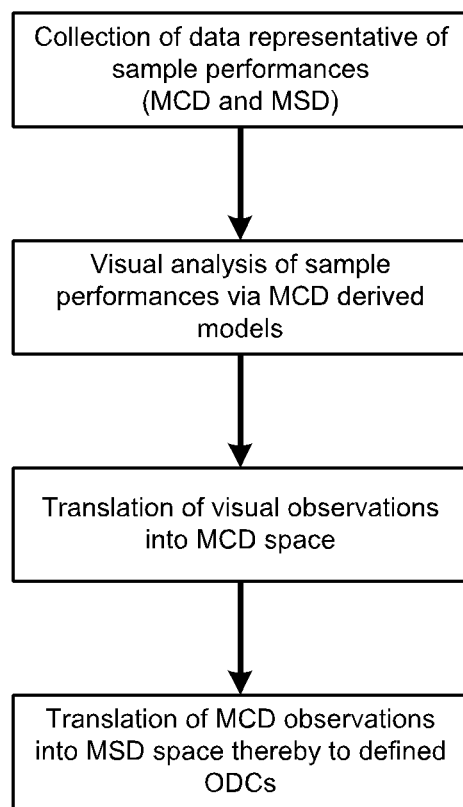
FIG. 2B illustrates a skill analysis method according to one embodiment.
Figure 2C:
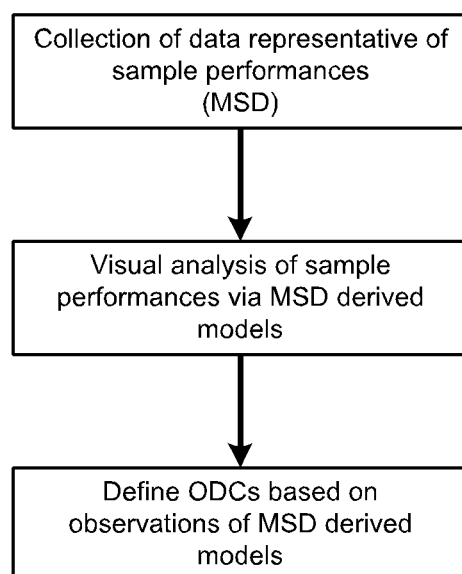
FIG. 2C illustrates a skill analysis method according to one embodiment.
Figure 2D:
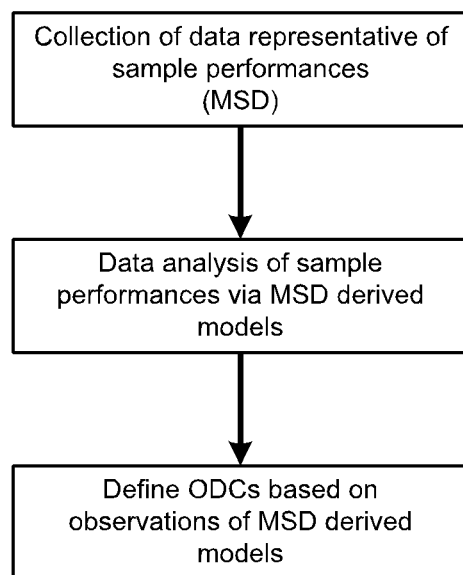
FIG. 2D illustrates a skill analysis method according to one embodiment.
Figure 2E:
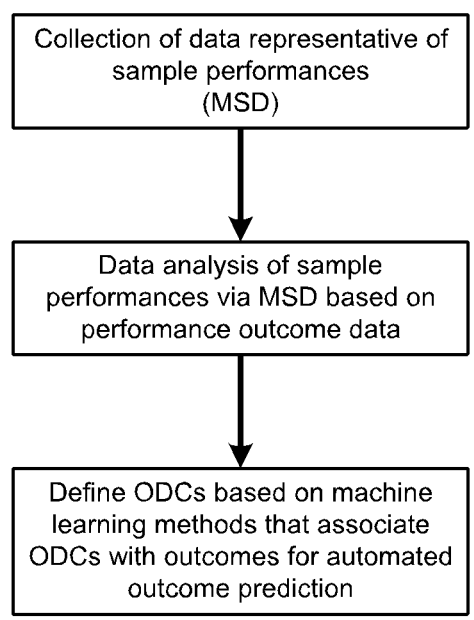
FIG. 2E illustrates a skill analysis method according to one embodiment.

Alternate methods are illustrated in FIG. 2B (which omits collection of video data, and instead visual analysis is performed via digital models generated using MCD), FIG. 2C (in which only MSD is used, and visual analysis is achieved using computer-generated models based on the MSD), FIG. 2D (in which there is no visual analysis, only data analysis of MCD to identify similarities and differences between samples) and FIG. 2E, which makes use of machine learning via MSD (MSD is collected for sample performances, data analysis is performed based on outcome data, such objectively measures one or more outcome parameters of a sample performance, and ODCs are defined based on machine learning thereby to enable prediction of outcomes based on ODCs).

In terms of using "one or more" coaches, in some cases multiple coaches are used thereby to define a consensus position with respect to analysis and coaching of a given skill, and in some cases multiple coaches are alternatively/additionally used to define coach-specific content. The latter allows an end user to select between coaching based on the broader coaching consensus, or coaching based on the particular viewpoint of a specific coach. At a practical level, in the context of a commercial implementation, the latter may be provided as basis for a premium content offering (optionally at a higher price point). The term "coach" may be used to describe a person who is qualified as a coach, or a person who operates in a coaching capacity for the present purposes (such as an athlete or other expert).

Skill Analysis Phase—Subject Selection Example

Subject selection includes selecting a group of subjects that are representative for a given skill. In some example embodiments, sample selection is performed to enable normalisation across one or more of the following parameters:

(i) Ability level. Preferably a plurality of subjects are selected such that there is adequate representation across a range of ability levels. This may include: initially determining a set of known ability levels, and ensuring adequate subject numbers for each level; analysing a first sample group, identifying ability level representation from within that group based on the analysis, and optionally expanding the sample group for under-represented ability levels, or other approaches. In embodiments described herein, user ability level is central to the automated coaching process at multiple levels. For example, as discussed further below, an initial assessment of user ability level is used to determine how a POD device is configured, for example in terms of ODCs for which it monitors. As context, mistakes made by a novice will differ from mistakes made by an expert. Moreover, it is advantageous to provide coaching directed to a user's actual ability level, for instance by first providing training thereby to achieve optimal (or near-optimal) performance at the novice level, and subsequently providing training thereby to achieve optimal (or near-optimal) performance at a more advanced level.

(ii) Body size and/or shape. In some embodiments, or for some skills, body size and/or shape may have a direct impact on motion attributes of a skill (for example by reference to observable characteristics of symptoms). An optional approach is to expand a sample such that it is representative for each of a plurality of body sizes/shapes, ideally at each ability level. As discussed further below, body size/shape normalisation is in some embodiments alternately achieved via a data-driven sample expansion method, as discussed further below. In short, this allows for a plurality of MCD/MSD data sets to be defined for each sample user performance, by applying a set of predefined transformations to the collected data thereby to transform that data across a range of different body sizes and/or shapes.

(iii) Style. Users may have unique styles, which do not materially affect performance. A sample preferably includes sufficient representation to enable normalisation across styles, such that observational characteristics of symptoms are style-independent. This enables coaching in a performance-based manner, independent of aspects of individual style. However, in some embodiments at least a selection of symptoms is defined in a style-specific manner. For example, this enables coaching to adopt a specific style (for example to enable coaching towards the style of a particular athlete).

For the sake of simplicity, the following description focuses on normalisation for multiple ability levels. In an example embodiment, there are "m" ability levels ($AL_1$ to $AL_m$), and "n" subjects ($SUB_1$ to $SUB_n$) at each ability level. That is, there are m*n subjects overall. It will be appreciated that the number of subjects at each individual ability level need not be equal (for example in some embodiments additional subjects are observed at a given ability level thereby to obtain more reliable data).

As noted, in some embodiments a sample is expanded over time, for example based on identification that additional data points are preferable.

Skill Analysis Phase—Performance Regime Definition Examples

In some example embodiments, each test subject ($SUB_1$ to $SUB_n$ at each of $AL_1$ to $AL_n$) performs a defined performance regime. In some embodiments the performance regime is constant across the plurality of ability levels; in other embodiments a specific performance regime is defined for each ability level. As context, in some cases a performance regime includes performances at varying intensity levels, and certain intensity levels may be inappropriate below a threshold ability level.

Some embodiments provide a process which includes defining an analysis performance regime for a given skill. This regime defines a plurality of physical skill performances that are to be performed by each subject for the purpose of sample data collection. Preferably, an analysis performance regime is defined by instructions to perform a defined number of sets, each set having defined set parameters. The set parameters preferably include:

(i) For each set, a number of repetitions. For example, a set may comprise n repetitions (where n≥1), in which the subject repeatedly attempts the skill with defined parameters.

(ii) Repetition instructions. For example, how much rest between repetitions.

(iii) Intensity parameters. For example, a set may be performed at constant intensity (each repetition $REP_1$ to $REP_n$ at the same intensity $I_c$), increasing intensity (performing repetition $R_1$ at intensity $I_1$, then performing $REP_2$ at intensity $I_2$, where $I_1 > I_2$, and so on), or decreasing intensity (performing repetition $REP_1$ at intensity $I_1$, then performing $R_2$ at intensity $I_2$, where $I_1 < I_2$, and so on), or more complex intensity profiles. The manner by which intensity is defined is dependent on the activity. For example, intensity parameters such as speed, power, frequency, and the like may be used. Such measures in some cases enable objective measurement and feedback. Alternately, a percentage of maximum intensity (for example "at 50% of maximum"), which is subjective but often effective.

By way of example, a given analysis performance regime for analysing a skill in the form of a rowing motion on an erg machine (a form of indoor rowing equipment) may be defined as follows:

Perform 6 sets ($SET_1$ to $SET_6$), with 5 minutes rest between sets.

For each set, perform 8 continuous repetitions ($REP_1$ to $REP_8$).

Intensity parameters are: $SET_1$ at Intensity=100 W; $SET_2$ at Intensity=250 W; $SET_3$ at Intensity=400 W; $SET_4$ at Intensity=550 W; $SET_5$ at Intensity=700 W; and $SET_6$ at Intensity=850 W.

Reference to the example of rowing is continued further below. However, it should be appreciated that this is a representative skill only provided for the sake of illustration, and that the underlying principles are applicable to a wide range of skills.

Skill Analysis—Phase Example Data Collection Protocol

Data is collected and stored in respect of each user's completion of the performance regime. As noted, for the present example. In the primary example considered herein, the data includes:

(i) Video data, captured by one or more capture devices from one or more capture angles. For example, one or more of a front, rear, side, opposite side, top, and other camera angles may be used.

(ii) Motion capture data (MCD), using any available motion capture technique.

(iii) Motion sensor data (MSD), using one or more body-mounted motion sensors.

It is preferable to control conditions under which data collection is performed, thereby to achieve a high degree of consistency and comparability between samples. For example, this may include techniques such as ensuring consistent camera placement, using markers and the like to assist in subject positioning, accurate positioning of MSUs on the subject, and so on.

Collected data is organised and stored in one or more databases. Metadata is also preferably collected and stored, thereby to provide additional context. Furthermore, the data is in some cases processed thereby to identify key events. In particular, events may be automatically and/or manually tagged in data for motion-based events. For example, a repetition of a given skill may include a plurality of motion events, such as a start, a finish, and one or more intermediate events. Events may include the likes of steps, the moment a ball is contacted, a key point in a rowing motion, and so on. These events may be defined in each data set, or on a timeline that is able to be synchronised across the video data, MCD and MSD.

Skill Analysis Phase—Example Data Synchronisation

Each form of data is preferably configured to be synchronised. For example:

Video data and MCD is preferably configured to be synchronised thereby to enable comparative review. This may include side-by-side video review (particularly useful for comparative analysis of video/MCD captured from different viewing angles) and overlaid review, for example using partial transparency (particularly useful for video/MCD captured for a common angle).

MSD is preferably configured to be synchronised such that data from multiple MSUs is transformed/stored relative to a common time reference. This in some embodiments is achieved by each MSU providing to the POD device data representative of time references relative to its own local clock and/or time references relative to an observable global time clock. Various useful synchronisation techniques for time synchronisation of data supplied by distributed nodes are known from other information technology environments, including for example media data synchronisation.

The synchronisation preferably includes time-based synchronisation (whereby data is configured to be normalised to a common time reference), but is not limited to time-based synchronisation. In some embodiments event-based synchronisation is used in addition to or as an alternative to time-based synchronisation (or as a means to assist time-based synchronisation).

Event-based synchronisation refers to a process whereby data, such as MCD or MSD, includes data representative of events. The events are typically defined relative to a local timeline for the data. For example, MCD may include a video file having a start point at 0:00:00, and events are defined at times relative to that start point. Events may be automatically defined (for example by reference to an event that is able to be identified by a software process, such as a predefined observable signal) and/or manually defined (for example marking video data during manual visual review of that data to identify times at which specific events occurred).

In the context of MCD, data is preferably marked to enable synchronisation based on one or more performance events. For example, in the context of rowing, various identifiable motion points in a rowing motion are marked, thereby to enable synchronisation of video data based on commonality of motion points. This is particularly useful when comparing video data from different sample users: it assists in identifying different rates of movement between such users. In some cases motion point based synchronisation is based on multiple points, with a video rate being adjusted (e.g. increased in speed or decreased in speed) such that two common motion points in video data for two different samples (e.g. different users, different repetitions, different sets, etc) are able to be viewed side-by-side (or overlaid) to show the same rate of progression between these motion points. For example, if one rower has a stroke time of 1 second, and another has a stroke time of 1.2 seconds, motion point based synchronisation is applied such that latter is contracted to one second thereby to enable a more direct comparison between the motion of the two rowers.

Skill Analysis Phase—Example Data Expansion Methodology

In some embodiments, MSD and/or MCD is transformed for each subject via a data expansion process thereby to define a plurality of further "virtual subjects" having different body attributes. For example, transformations are defined thereby to enable each MCD and/or MSD data point to be transformed based on a plurality of different body sizes. This enables capture of a performance from a subject having a specific body size to be expanded into a plurality of sample performances reflective of different body sizes. The term "body sizes" refers to attributes such as height, torso length, upper leg length, lower leg length, hip width, shoulder width, and so on. It will be appreciated that these attributes would in practice alter the movement paths and relative positions of markers and MSUs used for MCD and MSD data collection respectively.

Data expansion is also useful in the context of body size normalisation, in that data collected from all sample performers is able to be expended into a set of virtual performances that include one or more virtual performances by virtual performers having "standard" body sizes. In some embodiments a single "standard" body size is defined. The use of a standard body size, and transformation of MSD and MCD from sample performances to that standard body size, allows for direct comparison of MCD and MSD in spite of body size differences of multiple sample performers.

Skill Analysis Phase—Example Visual Analysis Methodology

As noted above, and shown in block 202 of FIG. 2A, an aspect of an example skill analysis methodology includes visual analysis of sample performances via video data. In other embodiments the video analysis is performed using computer-generated models derived from MCD and/or MSD as an alternative to video data, or in addition to video data. Accordingly, although examples below focus on review based on video data, it should be appreciated that such examples are non-limiting, and the video data is in other examples substituted for models generated based on MCD and/or MSD.

Visual analysis is performed for a variety of purposes, including: preliminary understanding of a skill and components of that skill; initial identification of symptoms; and analysis of individual sample performances based on a defined analysis schema.

Figure 3:
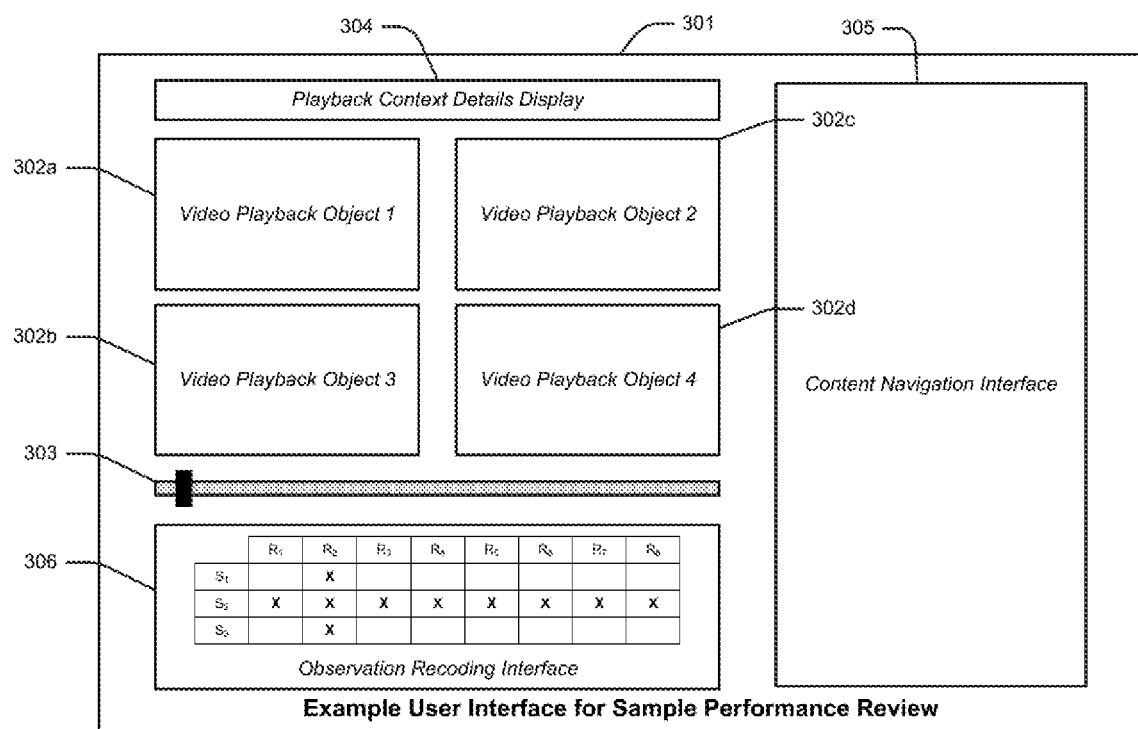
FIG. 3 illustrates a user interface display view for a user interface according to one embodiment.

FIG. 3 illustrates an example user interface 301 according to one embodiment. It will be appreciated that specially adapted software is not used in all embodiments; the example of FIG. 3 is provided primarily to illustrate key functionalities that are of particular use in the visual analysis process.

User interface 301 includes a plurality of video display objects 302a-302d, which are each configured to playback stored video data. In some embodiments the number of video display objects is variable, for example based on (i) a number of video capture camera angles for a given sample performance, with a video display object provided for each angle; and (ii) user control. In terms of user control, a user is enabled to select video data to be displayed, either at the performance level (in which case multiple video display objects are collectively configured for the multiple video angles associated with that performance) or on an individual video basis (for example selecting a particular angle from one or more sample performances). Each video display object is configured to display either a single video, or simultaneously display multiple videos (for example two videos overlaid on one another with a degree of transparency thereby to enable visual observation of overlap and differences). A playback context display 304 provides details of what is being shown in the video display objects.

Video data displayed in objects 302a to 302d is synchronised, for example time-synchronised. A common scroll bar 303 is provide to enable synchronous navigation through the multiple synchronised videos (which, as noted, may include multiple overlaid video objects in each video display object). In some embodiments a toggle is provided to move between time synchronisation and motion event based synchronisation.

A navigation interface 305 enables a user to navigate available video data. This data is preferably configured to be sorted by reference to a plurality of attributes, thereby to enable identification of desired performances and/or videos. For example, one approach is to sort firstly by skill, then by ability level, and then by user. In a preferred embodiment a user is enabled to drag and drop performance video data sets and/or individual videos into video display objects.

FIG. 3 additionally illustrates an observation recording interface 306. This is used to enable a user to record observations (for example complete checklists, make notes and the like), which are able to be associated with a performance data set that is viewed. Where multiple performance data sets are viewed, there is preferably a master set, and one or more overlaid comparison sets, and observations are associated with the master set.

Skill Analysis Phase—Example Symptom Identification via Visual Analysis

In an example embodiment, multiple experts (for example coaches) are engaged to review sample performances thereby to identify symptoms. In some cases this is facilitated by an interface such as user interface 301, which provides an observation recording interface 306.

In overview, each expert reviews each sample performance (via review of video data, or via review of models constructed from MCD and/or MSD) based on a predefined review process. For example, the review process may be predefined to require a certain number of viewings under certain conditions (for example regular speed, slow motion, and/or with an overlaid "correct form" example). The expert makes observations with respect to identified symptoms.

FIG. 4A illustrates an example checklist used in one embodiment. Such a checklist may be completed in hard copy form, or via a computer interface (such as interface 306 of FIG. 3). The checklist identifies data attributes including: a skill being analysed (in this example being "standard rowing action) a reviewer (i.e. the expert/coach performing the review), a subject (being the person shown in the sample performance, identified by a name or an ID), the ability level of the subject, and a set that is being reviewed. Additional details for any of these data attributes may also be displayed, along with other aspects of data.

The checklist then includes a header column identifying symptoms for which the expert is instructed to observe. In FIG. 4A these are shown as $S_1$ to $S_6$, however in practice it is preferable to record the symptoms by reference to a descriptive name/term (such as "snatched arms" or "rushing slide" in the context of the present rowing example). A header row denotes individual repetitions $REP_1$ to $REP_8$. The reviewer notes the presence of each symptom in respect of each repetition. The set of symptoms may vary depending on ability level.

Data derived from checklists (and other collection means) such as that shown in FIG. 4A is collected, and processed thereby to determine presence of symptoms in each repetition of each set for the sample performances. This may include determining a consensus view for each repetition, for example requiring that a threshold number of experts identify a symptom in a given repetition. In some cases consensus view data is stored in combination with individual-expert observation data.

Video data, MSD, and MCD is then associated with data representative of symptom presence. For example, an individual data set defining MSD for a given repetition of a given set of a given sample performance is associated with one or more identified symptoms.

In some embodiments, a checklist such as that of FIG. 4A is pre-populated with predicted symptoms based on analysis of MSD based on a set of predefined ODCs. A reviewer is then able to validate the accuracy of automated predictions based on MSD by confirming/rejecting those predictions based on visual analysis. In some embodiments such validation is performed as a background operation without pre-populating of checklists.

Skill Analysis—Phase Example Symptom to Cause Mapping

In some embodiments, analysis is performed thereby to enable mapping of symptoms to causes based on visual analysis. As context, a given symptom may result from any one or more of a plurality of underlying causes. In some instances a first symptom is a cause for a second symptom. From a training perspective, it is useful to determine, for a given symptom, the root underlying cause. Then, training can be provided to address that cause, and hence assist in rectifying the symptom (in embodiments where "symptoms" are indicative of incorrect form).

By way of example, referring again to a standard rowing motion, the following symptoms may be defined:

Minimal rock over.
Bum shove.
Snatched arms.
Rushing recovery slide.
Over the mountain.
Knees bending before hands past knees.
Recovery too short.
C-shaped back.

Then, for each symptom, a plurality of possible causes is defined. For example, in the context of "snatched arms", causes may be defined as:

Loading arms early.
Loading back early.
Rushing recovery slide.

Analysis of symptom-cause correlations assists in predicting/determining which of the plurality of causes is responsible for an identified symptom. In the case that a cause is also a symptom (such as "rushing recovery slide" above, then a cause for that symptom is identified (and so on via a potentially iterative process) until a predicted root cause is identified. That root cause can then be addressed.

In some embodiments, experts perform additional visual analysis thereby to associate symptoms with causes. This may be performed at any one or more of a plurality of levels. For example:

Association of symptoms with underlying causes at a general skill-based level.

Association of symptoms with underlying causes generally for each ability level.

Association of symptoms with underlying causes for each individual athlete.

Association of symptoms with underlying causes for each set performed by each individual athlete (which provides, for example, guidance as to a relationship between ability, intensity, and symptom/cause relationships).

Association of symptoms with underlying causes for each repetition of each set performed by each individual athlete. This, whilst more resource intensive, enables analysis of MSD for particular causes on a detailed basis.

As with symptom identification, checklists are used in some embodiments. An example checklist is provided in FIG. 4B. In this checklist, a reviewer notes correlation between identified symptoms (being $S_1$, $S_2$, $S_4$ and $S_5$ in this example) and causes for a given set. In the case of a computer-implemented checklist, the header column may be filtered to reveal only symptoms identified as being present in that set. In some embodiments an expert is enabled to add additional cause columns to checklists.

Data representative of symptom-cause correlation is aggregated across the multiple reviewers thereby to define an overlap matrix, which identifies a consensus view of the relationship between symptoms and causes as identified by the multiple experts. This may be on an ability level basis, athlete basis, set basis, or repetition basis. In any case, the aggregation enables determination of data that allows for prediction of a cause or possible causes in the event that a symptom is identified for an athlete of a given ability level. Where ODCs are defined for individual causes, it allows for processing of MSD thereby to identify presence of any of the one or more identified possible causes.

In some embodiments, symptom-cause correlations which are not sufficiently consistent between experts to become part of the consensus view are stored for the purpose of premium content generation. For example, in the contest of a training program, there may be multiple levels of premium content:

A base level, which uses the consensus view for symptom-cause correlation;

A higher level, which additionally uses a further group of symptom-cause correlations that are associated with a particular expert (based on observation that they are consistently identified by that expert, but not reflected in the consensus view).

The overlap matrix may also be used to define relative probabilities of particular causes being responsible for particular symptoms based on context (such as ability level). For example, at a first ability level it may be 90% likely that Symptom A is a result of Cause B, but at a second ability level Cause B may be only a 10% likelihood for that symptom, with Cause C being 70% likely.

In some embodiments, analysis is performed thereby to associate each repetition with causes (in a similar manner to symptoms above), thereby to assist in the identification of ODCs for causes in MSD. However, in other embodiments causes are identified on a probabilistic predictive basis without a need for analysis of MSD.

Skill Analysis Phase: Example Identification of Ability Level Symptoms

In some embodiments, an important category of symptoms are symptoms that enable categorisation of subjects into defined ability levels. Categorisation into a given ability level may be based upon observation of a particular symptom, or observation of one or more of a collection of symptoms.

As described further below, some embodiments make use of training program logic that first makes a determination as to ability level, for example based on observation ability level representative symptoms, and then performs downstream actions based on that determination. For example, monitoring for ODCs is in some cases ability level dependent. For example ODCs for a given symptom are defined differently at a first ability level as compared with a second ability level. In practice, this may be a result of a novice making course errors to display the symptom, but an expert displaying the symptom via much finer movement variations.

Skill Analysis Phase—Example Determining of ODCs (e.g. for State Engine Data)

Following visual analysis by experts/coaches, the skill analysis phase moves into a data analysis sub-phase, whereby the expert knowledge obtained from visual analysis of sample performances is analysed thereby to define ODCs that enable automated detection of symptoms based on MSD. For example, such ODCs are used in state engine data which is later downloaded to end user hardware (for example POD devices), such that a training program is able to operate based on input representing detection of particular symptoms in the end user's physical performance.

It will be appreciated that a range of different methodologies are used in various embodiments to define ODCs for a given symptom. In some embodiments, a general methodology includes:

(i) Performing analysis of MSD thereby to identify a combination of data attributes (for example based on MSD including acceleration rates and directions), which based on the outcomes of visual analysis are predicted to be indicative of the presence of a symptom;

(ii) Testing those data attributes against data representative of the sample performances (for example using the actual recorded MSD) to verify that those data attributed are present in all sample performances displaying the relevant symptom (optionally at an ability-level specific basis); and (iii) Testing those data attributes against data representative of the sample performances (for example using the actual recorded MSD) to verify that those data attributed are not present sample performances that do not display the relevant symptom (again, optionally at an ability-level specific basis).

Examples include, but are not limited to the following:

Approaches that use MCD as a stepping stone between visual analysis and MSD;

Approaches that move directly from visual analysis to analysis of MSD;

Approaches that define ODCs based on data obtained from individual sensors; and

Approaches that define ODCs based on overall body movement using a virtual body model constructed from MSD.

A selection of examples are described in detail below.

ODCs are also in some embodiments tuned thereby to make efficient use of end-user hardware, for example by defining ODCs that are less processor/power intensive on MSUs and/or a POD device. For example, this may be relevant in terms of sampling rates, data resolution, and the like.

Skill Analysis Phase—Example Translation of Visual Observations into MCD Space

As noted above, in some embodiments the MCD space is used as a stepping stone between visual observations and MSD data analysis. This is useful in avoiding challenges associated with accurately defining a virtual body model based on MSD (for example noting challenges associated with transforming MSD into a common geometric frame of reference).

In overview, the process includes, for a given symptom, analysing MCD associated with performances that have been marked as displaying that symptom. This analysis is in some embodiments performed at an ability level specific basis (noting that the extent to which a symptom is observable from motion may vary between ability levels). For example, the analysis includes comparing MCD (such as a computer generated model derived from MCD) for samples displaying the relevant symptom with MDC for samples which do not display the symptom.

Figure 5:
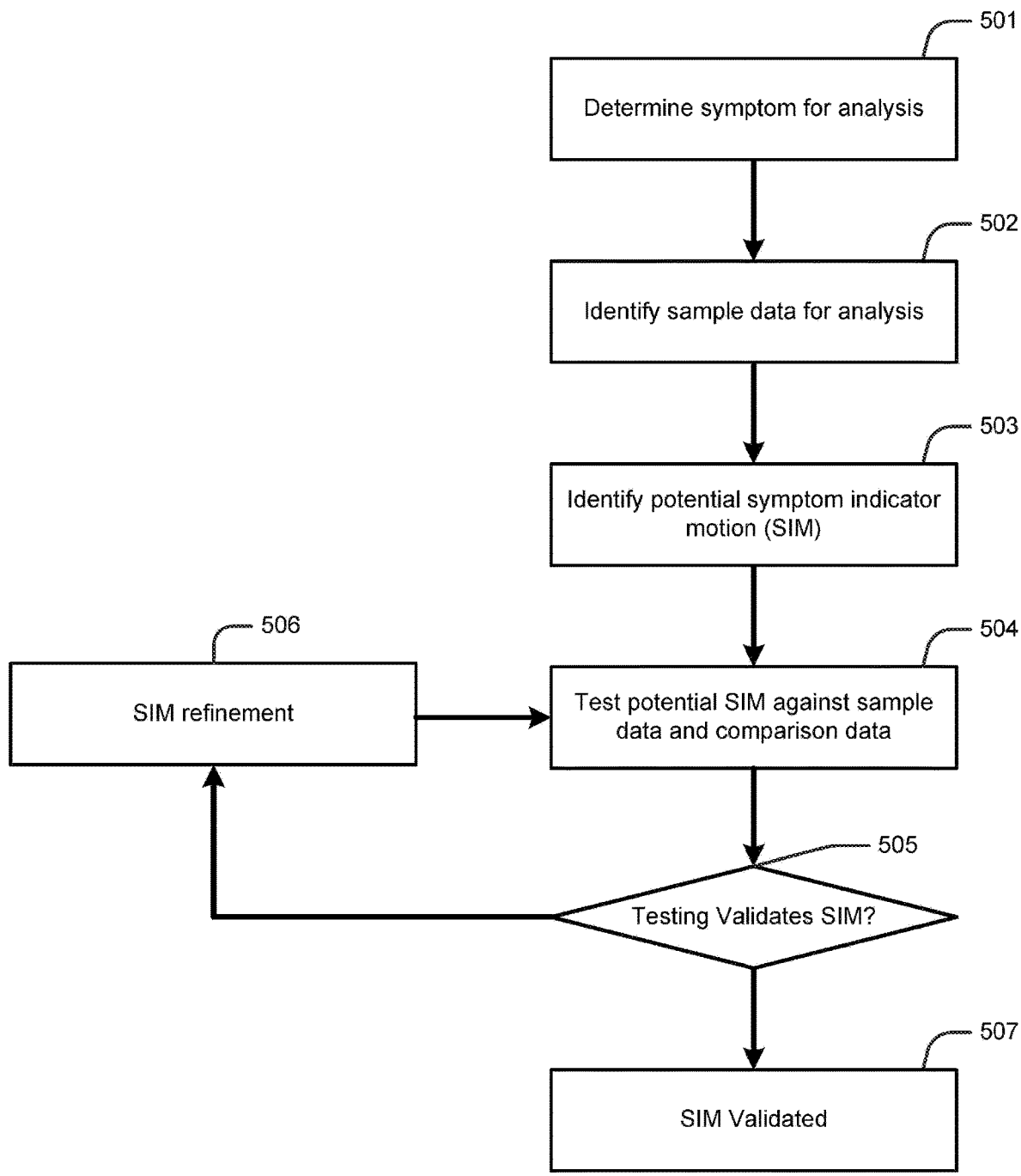
FIG. 5 illustrates a SIM analysis method according to one embodiment.

FIG. 5 illustrates a method according to one embodiment. It will be appreciated that this is an example only, and various other methods are optionally used to achieve a similar purpose. Block 501 represents a process including determining a symptom for analysis. For example, in the context of rowing, the symptom may be "snatched arms". Block 502 represents a process including identifying sample data for analysis. For example, the sample data may include:

MCD for all repetitions associated with the symptom.

MCD for all repetitions associated with the symptom at specific intensity parameters. That is, the analysis considers how a symptom presents at specific intensity parameters (as opposed to other intensity parameters).

MCD for all repetitions associated with the symptom at a specific ability level. That is, the analysis considers how a symptom presents at a specific ability level (as opposed to other ability levels).

MCD for all repetitions associated with the symptom at specific intensity parameters and a specific ability level (i.e. combining the two previous approaches).

Other approaches may also be used. In some cases multiple of the above approaches are used in combination to better understand the effect of factors such as intensity and ability (which may turn out to be relevant or irrelevant to a given symptom).

The MCD used here is preferably MCD normalised to a standard body size, for example based on sample expansion techniques discussed above. Likewise, ODCs derived from such processes are able to be de-normalised using transformation principles of sample expansion thereby to be applicable to a variable (and potentially infinitely variable) range of body sizes.

Functional block 503 represents a process including identifying a potential symptom indicator motion (SIM). For example, this includes identifying an attribute of motion observable in the MCD for each of the sample repetitions which is predicted to be representative of the relevant symptom. An indicator motion is in some embodiments defined by attributes of a motion path of a body part at which a MSU is mounted. The attributes of a motion path may include the likes of angle, change in angle, acceleration/deceleration, change in acceleration/deceleration, and the like. This is referred to herein as "point path data", being data representative of motion attributes of a point defined on a body. In this regard, a potential SIM is defined by one or more sets of "point path data" (that is, in some cases there is one set of point path data, where the SIM is based on motion of only one body part, and in some cases there are multiple sets of point path data, where the SIM is based on motion of multiple body parts such as a forearm and upper arm).

As context, a set of point path data may be defined to include the following data for a given point:

X-axis acceleration: Min: A, Max B.
Y-axis acceleration: Min: C, Max D.
Z-axis acceleration: Min: E, Max F.

Data other than acceleration may also be used. Furthermore, there may be multiple acceleration measurements, and these may be time referenced to other events and/or measurements. For example, one set of point path data may be constrained by reference to a defined time period following observation of another set of point path data. As context this could be used to define SIM that considers relative movement of a point on the upper leg with a point on the forearm.

Functional block 504 represents a testing process, whereby the potential SIM is tested against comparison data. In some embodiments the testing validates that:

(i) The one or more sets of point path data are observed in the MCD for each of the repetitions in the sample data. This validates that the potential SIM is effective in terms of identifying the presence of the symptom in the sample for which it is designed to operate.

(ii) The one or more sets of point path data are not observed in the MCD for repetitions that are not associated with the relevant symptom. This validates that the potential SIM will not be triggered where the symptom is not present.

Decision 505 represents determination of whether the potential SIM is validated based on testing at 505.

Where a potential SIM is not able to be successfully validated, it is refined (see block 506) and re-tested. In some embodiments refinement and re-testing is automated via an interactive algorithm. For example, this operates to narrow down point path data definitions underlying a previously defined potential SIM to a point where it is able to be validated as unique by reference to MCD for performance repetitions for which the relevant symptom is not present. In some cases a given SIM is not able to be validated following a threshold number of iterations, and a new staring point potential SIM is required.

Block 507 represents validation of a SIM following successful testing.

In some embodiments, where the sample data is a subset of the total MCD data for all repetitions associated with the relevant symptom, data is generated to indicate whether the SIM is validated also for any other subsets of that total MCD data (for example the SIM is derived based on analysis at a first ability level, but also valid at a second ability level).

It should be appreciated that the process of determining potential SIMs may be a predominately manual process (for example based on visual analysis of video and/or MCD derived model data). However, in some embodiments the process is assisted by various levels of automation. For example, in some embodiments an algorithm is configured to identify potential SIMs based on commonality of MCD in symptom-displaying MCD as compared with MCD in symptom-absent MCD. Such an algorithm is in some embodiments configured to define a collection of potential SIMs (each defined by a respective one or more sets of point path data, in the MCD space or the MSD space) which comprehensively define uniqueness of sample set of symptom-displaying sample performances relative to all other sample performances (with the sample performances being normalised for body size). In one embodiment, an algorithm is configured to output data representative of a data set containing all MCD common to a selected symptom or collection of symptoms, and enable filtering of that data set (for example based on particular sensors, particular time windows within a motion, data resolution constraints, and so on) thereby to enable user-guided narrowing of the data set to a potential SIM that has characteristics that enable practical application in the context of end-user hardware (for example based on MCDs of MSU-enabled garments provided to end users).

In some embodiments the testing process is additionally used to enable identification of symptoms in repetitions where visual analysis was unsuccessful. For example, where the number of testing failures is small, those are subjected to visual analysis to confirm whether the symptom is indeed absent, or subtly present.

Skill Analysis Phase—Example Translation from MCD Space into MSD Space (ODCs)

SIMs validated via a method such as that of FIG. 5 are then translated into the MSD space. As noted, each SIM includes data representative of one or more sets of point path data, with each set of point path data defining motion attributes for a defined point on a human body.

The points on the human body for which point path data is defined preferably correspond to points at which MSUs are mounted in the context of (i) a MSU arrangement worn by subjects during the sample performances; and (ii) a MSU-enabled garment that is utilised by end users. In some embodiments the end user MSU-enabled garment (or a variation thereof) is used for the purposes of sample performances.

In the case that point path data is defined for a point other than that where a MSU is mounted, a data transformation is preferably performed thereby to adjust the point path data to such a point. Alternately, such a transformation may be integrated into a subsequent stage.

In overview, MSD for one or more of the sample performance repetitions in sample data (the sample data of block 502 of FIG. 5) is analysed thereby to identify data attributes corresponding to the point path data. For example, the point path data may be indicative of one or more defined ranges of motion and/or acceleration directions relative to a frame of reference (preferably a gravitational frame of reference).

In some embodiments, the translation from (a) a SIM derived in the MCD space into (b) data defined the MSD space includes:
  (i) For each set of point path data, identifying MSD attributes, present in each of the sample performances to which the SIM relates, that are representative of the point path data. In some cases, the relationship between point path data and attributes of MSD is imperfect, for example due to the nature of the MSD. In such cases, the identified MSD attributes may be broader than the motions defined by the point path data.
  (ii) Validating the identified MSD data attributes by a process similar to the iterative testing of blocks 504-506 of FIG. 5, thereby to validate that the identified MSD attributes are consistently found in the MSD for symptom-displaying sample performances, and absent in all symptom-absent sample performances.

This process of translation into the MSD space results in data conditions which, when observed in data derived from one or more MSUs used during the collection phase (e.g. block 201 of FIG. 2A), indicates the presence of a symptom. That is, the translation process results in ODCs for the symptom.

ODCs defined in this manner are defined by individual sensor data conditions for one or more sensors. For example, ODCs are observed based upon velocity and/or acceleration measurements at each sensor, in combination with rules (for example timing rules: sensor X observes A, and within a defined time proximity sensor X observes B).

The ODCs are then able to be integrated into state engine data, which is configured to be made available for downloading to an end user device, thereby to enable configuration of that end user device to monitor for the relevant symptoms.

It will be appreciated that the ODCs defined by the translation process above are unique to the MSUs used in the data collection phase. For this reason, it is convenient to use the same MSUs and MSU positioning (for example via the same MSU-enabled garment) during the collection phase as will be used by end users. However, in some embodiments there are multiple versions of end-user MSU-enabled garments, for example with different MSUs and/or different MSU positioning. In such cases, the translation into the MSD space is optionally performed separately for each garment version. This may be achieved by applying known data transformations and/or modelling of the collected test data via virtual application of virtual MSU configurations (corresponding to particular end-user equipment). For example, in relation to the latter, a virtual model derived from MCD is optionally used as a framework to support one or more virtual MSUs, and determine computer-predicted MSU readings corresponding to SIM data. It will be appreciated that this provides an ability to re-defined ODCs over time based on hardware advances, given that data collected via the analysis phase is able to be re-used over time in such situations.

Figure 6:
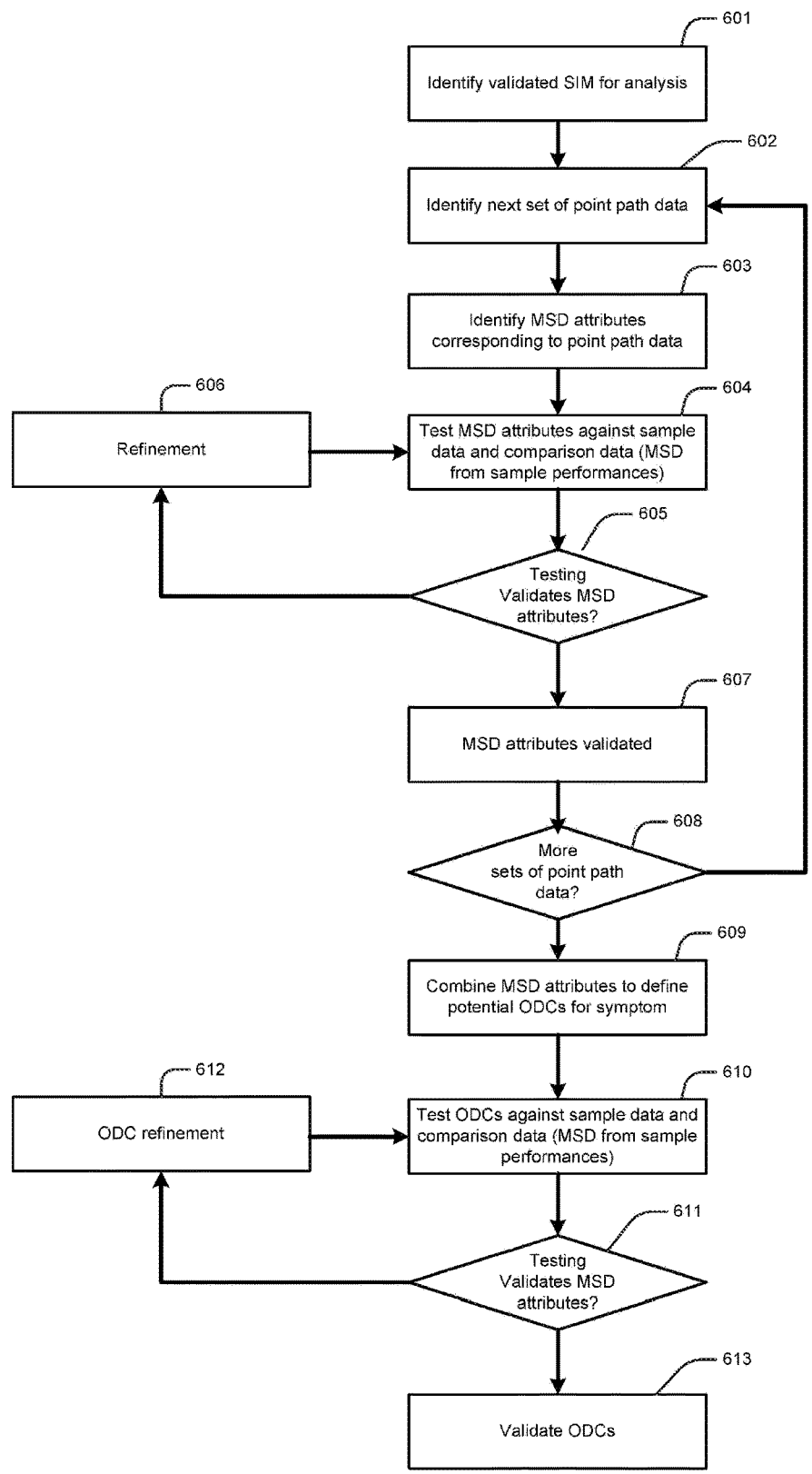
FIG. 6 illustrates a SIM analysis method according to one embodiment.

An example process is illustrated in FIG. 6, being a process for defining ODCs or a SIM generated based on MSC analysis. A validated SIM is identified at 601. A first one of the sets of point path data is identified at 602, and this is analysed via a process represented by blocks 603 to 608, which loops for each set of point path data. This looped process includes identifying potential MSD attributes corresponding to the point path data. For example, in some embodiments this includes processing collected MSD for the same point in time as the point path data for all or a subset of the relevant collected MSD (noting that MCD and MSD is stored in a manner configured for time synchronisation). Testing is then performed at 604, to determine at 605 whether the identified MSD attributes are present in all relevant symptom-present MSD collected from sample performances (and, in some embodiments to ensure it is absent in symptom-absent MSD). Where necessary, refinement is performed at 606, otherwise the MSD attributes are validated to 607.

Once the looped process of blocks 603 to 608 is completed for all sets of point path data in the SIM, the validated MSD attributes are combined at 609, thereby to define potential ODCs for the symptom. These are then also tested, refined and validated via the processes of blocks 610 to 613, thereby to ensure that the potential ODC is: (i) identified in all relevant sample performance MSD for which the relevant symptom is indeed present, and (ii) not identified in all relevant sample performance MSD for which the relevant symptom is absent (the term "relevant" indicating that in some cases analysis is limited by ability level or the like)

It will be appreciated that various alternate methodologies are used in further embodiments thereby to define ODCs for a given symptom. However, in substantially all cases method includes performing analysis thereby to define observable data conditions that are able to be identified in MSD (collected or virtually defined) for sample performances where the symptom is present, but not able to be identified in sample performances where the symptom is absent.

Skill Analysis Phase—Alternate Translation of Visual Observations into MCD Space Via MCD Space In a further embodiment, MCD is used to generate a virtual body model, and that model is associated with time-synchronised MSD. In that manner, analysis is able to be performed using MSD for a selected one or more MSUs at a particular point in a skill performance motion.

The MSD used at this stage may be either MSD for a particular performance, or MSD aggregated across a subset of like performances (for example performances by a standardized body size at a defined ability level). The aggregation may include either or both of: (i) utilising only MSD that is similar/identical in all of the subset of performances; and (ii) defining data value ranges such that the aggregated MSD includes all (or a statistically relevant proportion) of MSD for the subset of performances. For example, in relation to the latter, MSD for a first performance might have: a value of A for x-axis acceleration of a particular sensor at a particular point in time, and MSD for a second performance might have: a value of B for x-axis acceleration of that particular sensor at that particular point in time. These are able to be aggregated into aggregated MSD where the value for x-axis acceleration of that particular sensor at that particular point in time is defined as being between A and B.

Hence, analysis is able to be performed to determine the likes of:
  (i) Values for one or more aspects of MSD (e.g. accelerometer values) for a particular sensor, at a particular point in a movement, for a specific performance.

(ii) Comparison data comparing the values at (i) with other performances at the same point in the movement (for example other performances displaying the same symptom at the same ability level).
(iii) Value ranges for one or more aspects of MSD (e.g. accelerometer values) for a particular sensor, at a particular point in a movement, for set of performances (for example other performances displaying the same symptom at the same ability level).
(iv) Comparison data for one or more aspects of MSD (e.g. accelerometer values) for a particular sensor, at a particular point in a movement, for a specific performance having a specific symptom, as compared with corresponding MSD for one or more further performances that do not display that specific symptom.

Such analysis is used to determine predicted ODCs for a given symptom.

Figure 7:
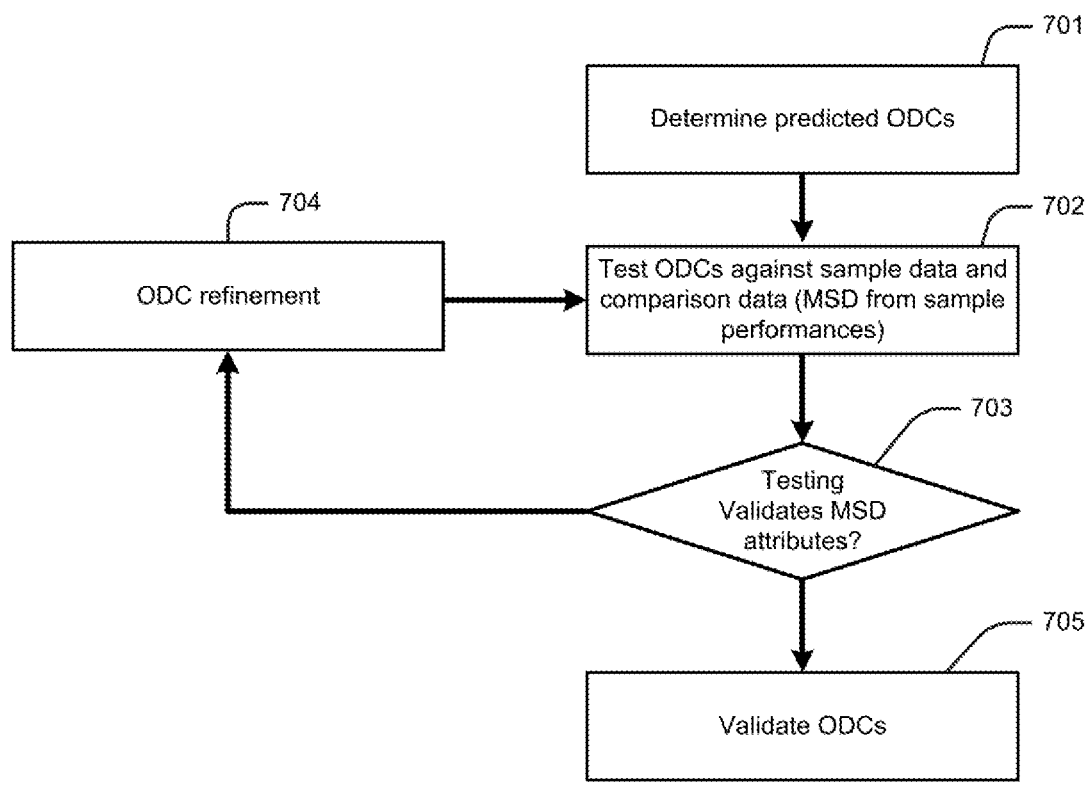
FIG. 7 illustrates an ODC validation method according to one embodiment.

Once predicted ODCs are defined, these are able to be tested using a method such as that shown in FIG. 7. Predicted ODCs for a particular symptom are determined at 701, and these are then tested against MSD for sample performances at 702. As with previous example, this is used to verify that the predicted ODCs are present in MSD for relevant performances displaying that symptom, and that the ODCs are not present in MSD for relevant performances that do not display the symptom. For example, the "relevant" performances are sample performances at a common ability level and in some embodiments normalised to a standard body size. Based on the testing the ODCs are refined at 704, or validated at 705.

Analysis Phase: Alternate Approach for Defining ODCs Via Body Modelling

Approaches described above are based around ODCs that look for particular data attributes in one or more of the individual sensors. An alternate approach is to define ODCs based around motion of a body, and define a virtual body model based on MSD collected from MSUs. For example, MSD is collected and processed thereby to transform the data into a common frame of reference, such that a 3 dimensional body model (or partial body model) is able to be defined and maintained based on movement data derived from MSUs. Exemplary techniques for deriving a partial and/or whole body model from MSD include transforming MSD from two or more MSUs into a common frame of reference. Such a transformation is optionally achieved by any one or more of the following techniques:

Precise positioning and/or measurement of MSU locations, and identification of known body positions at predefined points on a timeline (for example start poses).

Utilisation of known positional relationships between motion capture points (for example mocap markers) and MSUs.

Using known body constraints, such as joint types, to relate MSD from a first sensor on one side of a joint to MSD at another side of a joint.

Using referential data that is common to multiple MSU to enable overall data transformation to a common frame of reference, for example using a direction of gravitational acceleration and a direction for magnetic north.

Of these, the first two are often advantageous in a manner the context of skill analysis, where MSUs are able to be installed in a controlled environment, and secondary data such as MCD is available to assist in MSD interpretation. The latter two are of greater relevance in situations where there is less control, for example where MSD is collected from a wearer of an end-user type MSU-enabled garment, potentially in an uncontrolled (or comparatively less controlled) environment. Additional information regarding such approaches is provided further below.

Alternate Example Methodologies for Objectively Defining Physical Skills

A further group of alternate methodologies for objectively defining physical skills is described below by reference to FIG. 8A to FIG. 8I. Aspects of these methodologies are in some embodiments combined with those described further above.

These methodologies, in a general sense, include three phases (which are not always clearly separable or followed via a strict linear progression. The first is a sample analysis phase 801, at which a given skill is analysed thereby to understand movement/position attributes that relate to optimal and sub-optimal performance. Then, a data analysis phase 802 includes applying the understanding gained at phase 801 to observable sensor data; this phase includes determining how a set of end-user sensors for a given end-user implementation are able to be used to identify, via sensor data, particular motion/position attributes from phase 801. This allows the understanding gained at phase 801 to be applied to end-users, for example in the context of training. That occurs at phase 803; a content author defines rules and the like for software that monitors an end-user's performance via sensor data. For example, a rule may define feedback that is provided to a user, based on knowledge from phase 801, when particular sensor data from phase 802 is observed.

As noted, these three phases are not in all cases clearly distinguished; there is some cases blending and/or overlap. Furthermore, they need not be performed as a plain linear process; in some cases there is cycling between phases.

The following examples are described by reference to performances analysed by reference to motion attributes. For example, motion data is derived from a plurality of sensors that are mounted to a human user (for example being provided on garments), and in some cases additionally one or more sensors mounted to equipment utilised by the human user (for example a skateboard, a tennis racket, and so on). The sensors may take various forms. An example considered herein, which should not be regarded as necessarily limiting, is to use a plurality of sensor units, with each sensor unit including: (i) a gyroscope; (ii) an accelerometer; and (iii) a magnetometer. These are each preferably three axis sensors. Such an arrangement allows collection of data (for example via a POD device as disclosed herein) which provides accurate data representative of human movements, for example based upon relative movement of the sensors. Examples of wearable garment technology are provided elsewhere in this specification.

In the various figures, similar processes are designated by like-numbered functional blocks.

Figure 8A:
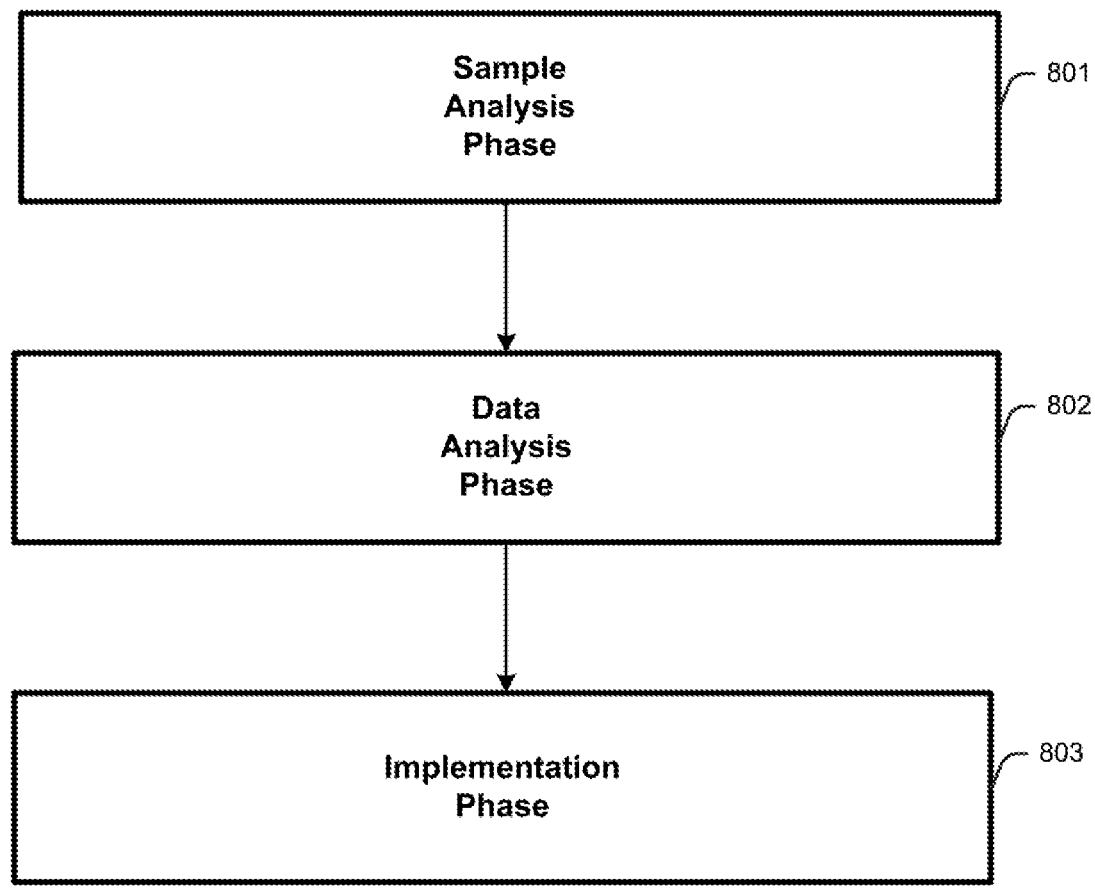
FIG. 8A illustrates a process flow according to one embodiment.
Figure 8B:
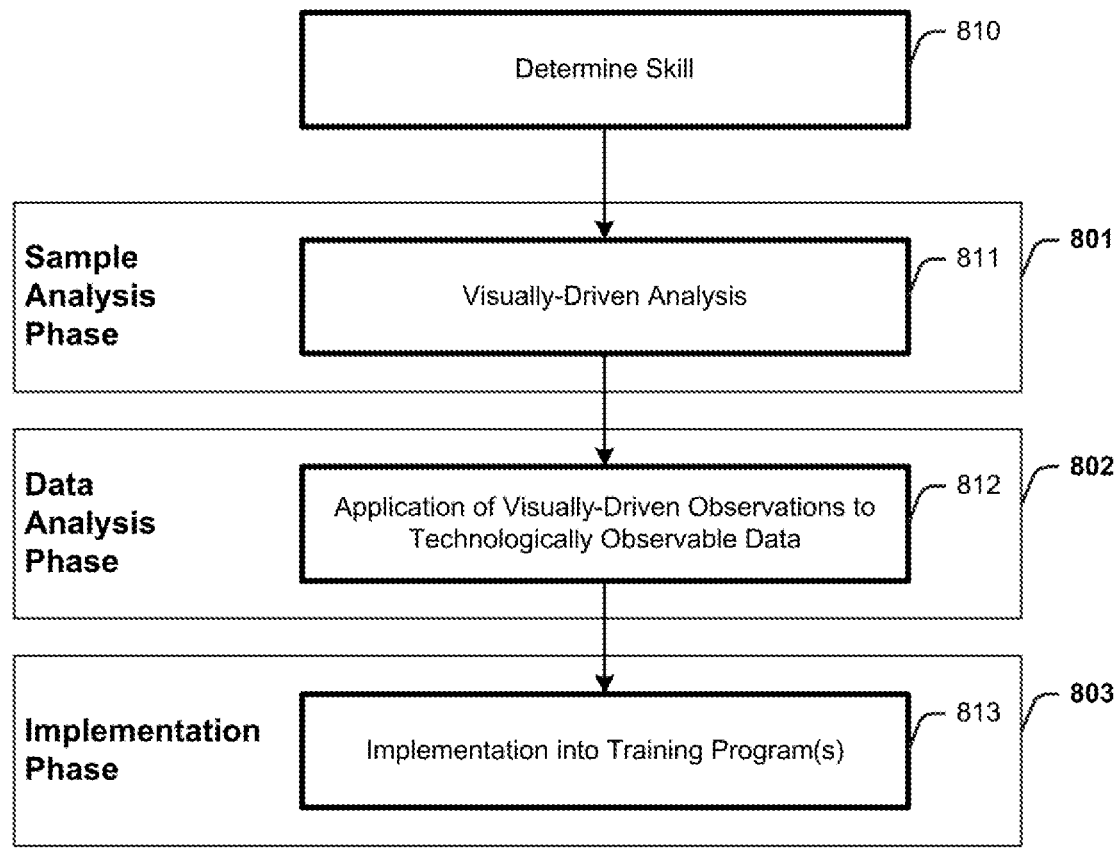
FIG. 8B illustrates a process flow according to one embodiment.

FIG. 8B illustrates a method according to one embodiment, which includes the three phases of FIG. 8A. The method commences with a preliminary step 810 which includes determining a skill that is to be the subject of analysis. For example, the skill may be a particular form of kick in football, a particular tennis swing, a skateboarding manoeuvre, a long jump approach, and so on. It will be appreciated that there is a substantially unlimited number of skills present in sporting, recreational, and other activities which could be identified and analysed by methods considered herein.

Sample analysis phase 801 includes analysis of multiple performances of a given skill, thereby to develop an understanding of aspects of motion that affect the performance of that skill, in this case via visually-driven analysis at 811. The visually-driven analysis includes visually comparing the multiple performances, thereby to develop knowledge of how an optimal performance differs from a sub-optimal performance. Example forms of visually-driven analysis include:

A first example of step 811 includes visually-driven analysis without technological assistance. An observer (or set of observers) watch as a skill is performed multiple times, and make determinations based on their visual observations.

A second example of step 811 includes visually-driven analysis utilising video. Video data is captured of the multiple performances, thereby to enable subsequent repeatable visual comparison of performances. A preferred approach is to capture performances from one or more defined positions, and utilise digital video manipulation techniques to overlay two or more performance videos from the same angle. For example, a skill in the form of a specific soccer kick may be filmed from a defined rear angle position (behind an athlete), with the ball being positioned in a defined location for each performance, and a defined target. Captured video from two or more performances are overlaid with transparency, based on a defined common origin video frame (selected based on a point in time in the movement that is to be temporally aligned in the comparative video). Assuming this is filmed in a controlled environment, only the player and the ball should differ in position between two video captures (and slight errors in camera position can be accounted for using background alignment). This allows an observer to more identify similarities and differences between performances based on variances in the overlaid performance movements. Multiple angles are preferably used (for example a side view and a top view).

A third example of step 811 includes visually-driven analysis utilising motion capture data. Motion capture data is collected for the multiple performances, for example using conventional motion capture techniques, mounted sensors, depth-sensitive video equipment (for example depth sensor cameras such as those used by Microsoft Kinect) and/or other techniques. This allows a performance to be reconstructed in a computer system based on the motion capture. The subsequent visual analysis may be similar to that utilised in the previous video example, however the motion capture approaches may allow for more precise observations, and additional control over viewpoints. For example three-dimensional models constructed via motion capture technology may allow free-viewpoint control, such that multiple overlaid performances are able to be compared from numerous angles thereby to identify differences in movement and/or position.

Other approaches for visually-driven analysis at phase 811 may also be used.

Observations arising from visually-driven analysis are in some embodiments descriptive. For example, observations may be defined in descriptive forms such as "inward tilt of hip during first second of approach", "bending of elbow before foot contact with ground", "left shoulder dropped during initial stance", and so on). The descriptive forms may include (or be associated) with information regarding an outcome of the described artefact, for example "inward tilt of hip during first second of approach causes ball to swing left of target".

For the purpose of this specification, the output of phase 801 (and step 811) is referred to as "performance affecting factors".

In FIG. 8B, phase 802 includes a functional block 812 which represents a process including application of visually-driven observations to technologically observable data. This may again use comparative analysis, but in this case based on digitized information, for example information collected using motion capture or sensors (which may be the same or similar sensors as worn by end-users). Functional block 812 includes, for a given performance affecting factor $PAF_n$, identifying in data derived from one or more performances which is attributable to $PAF_n$. This may include comparative analysis of data for one or more performances that do not exhibit $PAF_n$ with data for one or more performances that do exhibit $PAF_n$. By way of example, captured data demonstrating "inward tilt of hip during first second of approach" is analysed to identify aspects of the data which are attributable to the "inward tilt of hip during first second of approach". This may be identified by way of comparison with data for a sample which does not demonstrate "inward tilt of hip during first second of approach".

As described herein, the data analysis results in determination of observable data conditions for each performance affecting factor. That is, $PAF_n$, is associated with $ODC_n$. Accordingly, when sensor data for a given performance is processed, a software application is able to autonomously determine whether $ODC_n$ is present, and hence provide output indicative of identification of $PAF_n$. That is, the software is configured to autonomously determine whether there is, for example, "inward tilt of hip during first second of approach" based on processing of data derived from sensors.

In some embodiments a given PAF is associated with multiple ODCs. This may include: ODCs associated with particular sensor technologies/arrangements (for example where some end users wear a 16 sensor suit, and others wear a 24 sensor suit); ODCs associated with different user body attributes (for example where a different ODC is required for a long-limbed user as opposed to a short-limbed user), and so on. In some embodiments, on the other hand, ODCs are normalised for body attributes as discussed further below.

In FIG. 8B, implementation phase 803 includes a functional block 813 representing implementation into training program(s). This includes defining end user device software functionalities which are triggered based on observable data conditions. That is, each set of observable data conditions is configured to be implemented via a software application that processes data derived from the end user's set of motion sensors, thereby to enable monitoring for presence of the associated set of performance affecting factors in the end-user's physical performance of the skill. In some embodiments a rules-based approach is used, for example "IF ODC, observed, THEN perform action X". It will be appreciated that rules of varying degrees of complexity are able to be defined (for example using other operators such as OR, AND, ELSE, and the like, or by utilisation of more powerful rule construction techniques). The precise nature of rules is left at the discretion of a content author. As a general principle, in some embodiments an objective is to define an action that is intended to encourage an end-user to modify their behaviour in a subsequent performance thereby to potentially move closer to optimal performance.

Continuing with the example above, one set of observable data conditions indicates that a user has exhibited "inward tilt of hip during first second of approach" in an observed performance. Accordingly, during phase 803 such observable data conditions are optionally associated with a feedback instruction (or multiple potential feedback instructions) defined to assist a user in replacing that "inward tilt of hip during first second of approach" with other movement attributes (for instance, optimal performance may require "level hips during first second of movement, upward tilt of hips after left foot contacts ground"). The feedback need not be at all related to hip tilt; coaching knowledge may reveal that, for example, adjusting a hand position or starting stance can be effective in rectifying incorrect hip position (in which case observable data conditions may also be defined for those performance affecting factors thereby to enable secondary analysis relevant to hip position).

Figure 8C:
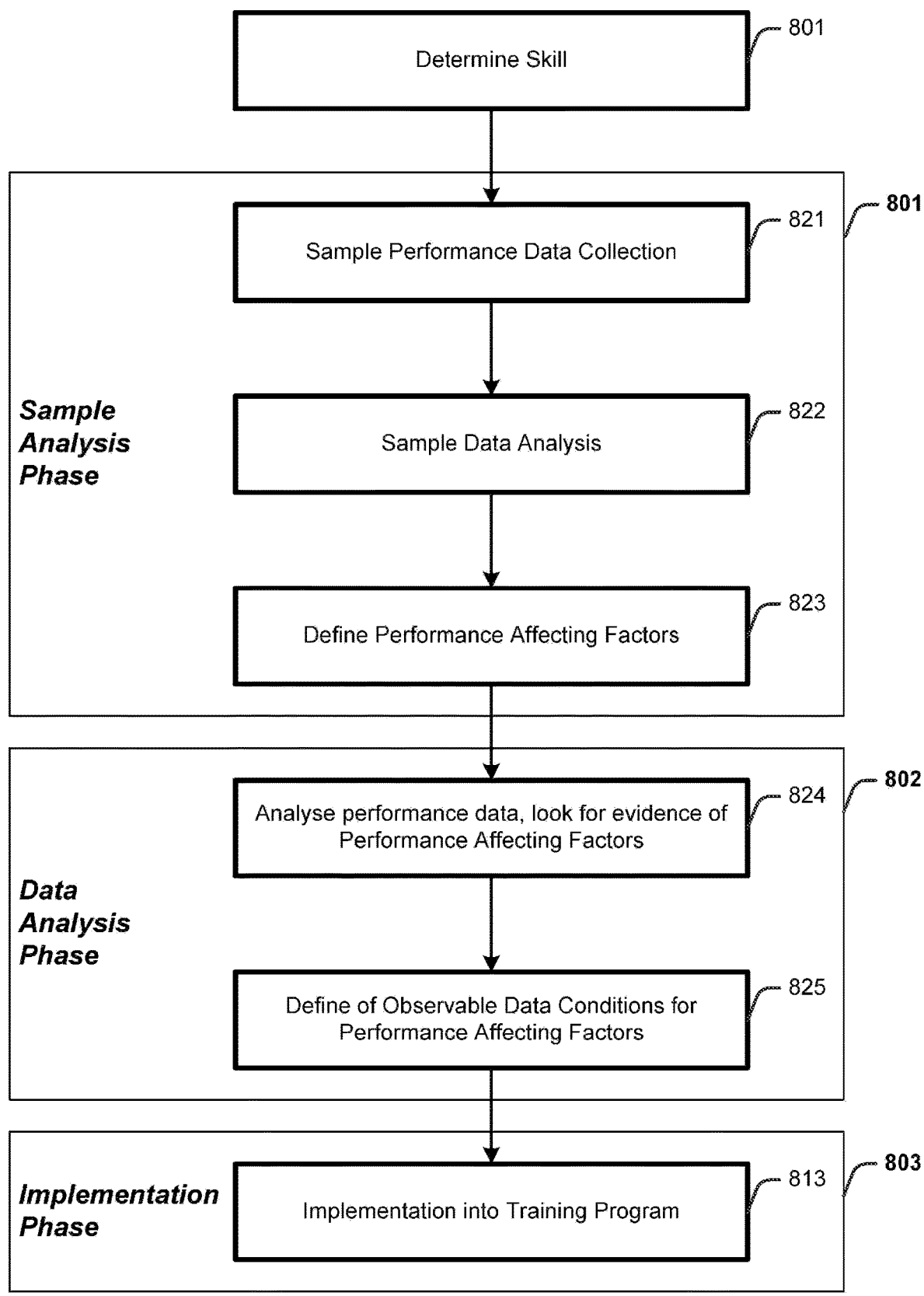
FIG. 8C illustrates a process flow according to one embodiment.

FIG. 8C illustrates a method according to one embodiment, showing an alternate set of functional blocks within phases 801 to 803, some of which having been described by reference to FIG. 8B.

Functional block 821 represents a sample performance collection phase, whereby a plurality of samples of performances are collected for a given skill. Functional block 822 represents sample data analysis, for example via visually-driven techniques as described above, or by other techniques. This leads to the defining of performance affecting factors for the skill (see functional block 823), which may be represented, for a skill $S_i$ as $S_iPAF_1$ to $S_iPAF_n$.

Functional block 824 represents a process including analysing performance data (for example data derived from one or more of motion capture, worn sensors, depth cameras, and other technologies) thereby to identify data characteristics that are evidence of performance affecting factors. For example, one or more performance-derived data sets known to exhibit the performance affecting factor are compared with one or more performance-derived data sets known to exhibit the performance affecting factor known not to exhibit the performance affecting factor. In some embodiments which use multiple worn sensors, key data attributed include: (i) relative angular displacement of sensors; (ii) rate of change of relative angular displacement of sensors; and (iii) timing of relative angular displacement of sensors and timing of and rate of change of relative angular displacement of sensors.

Functional block 825 represents a process including, based on the analysis at 824, defining observable data conditions for each performance affecting factor. The observable data conditions are defined in a manner that allows for them to be autonomously identified (for example as trap states) in sensor data derived from an end-user's performance. They may be represented, for a skill $S_i$ as $S_iODC_1$ to $S_iODC_n$. $S_iPAF_1$ to $S_iPAF_n$. As noted above, in some embodiments a given PAF is associated with multiple ODCs. This may include: ODCs associated with particular sensor technologies/arrangements (for example where some end users wear a 16 sensor suit, and others wear a 24 sensor suit); ODCs associated with different user body attributes (for example where a different ODC is required for a long-limbed user as opposed to a short-limbed user), and so on. In some embodiments, on the other hand, ODCs are normalised for body attributes as discussed further below.

Alternate Example: Sample Analysis Methodology

Figure 8D:
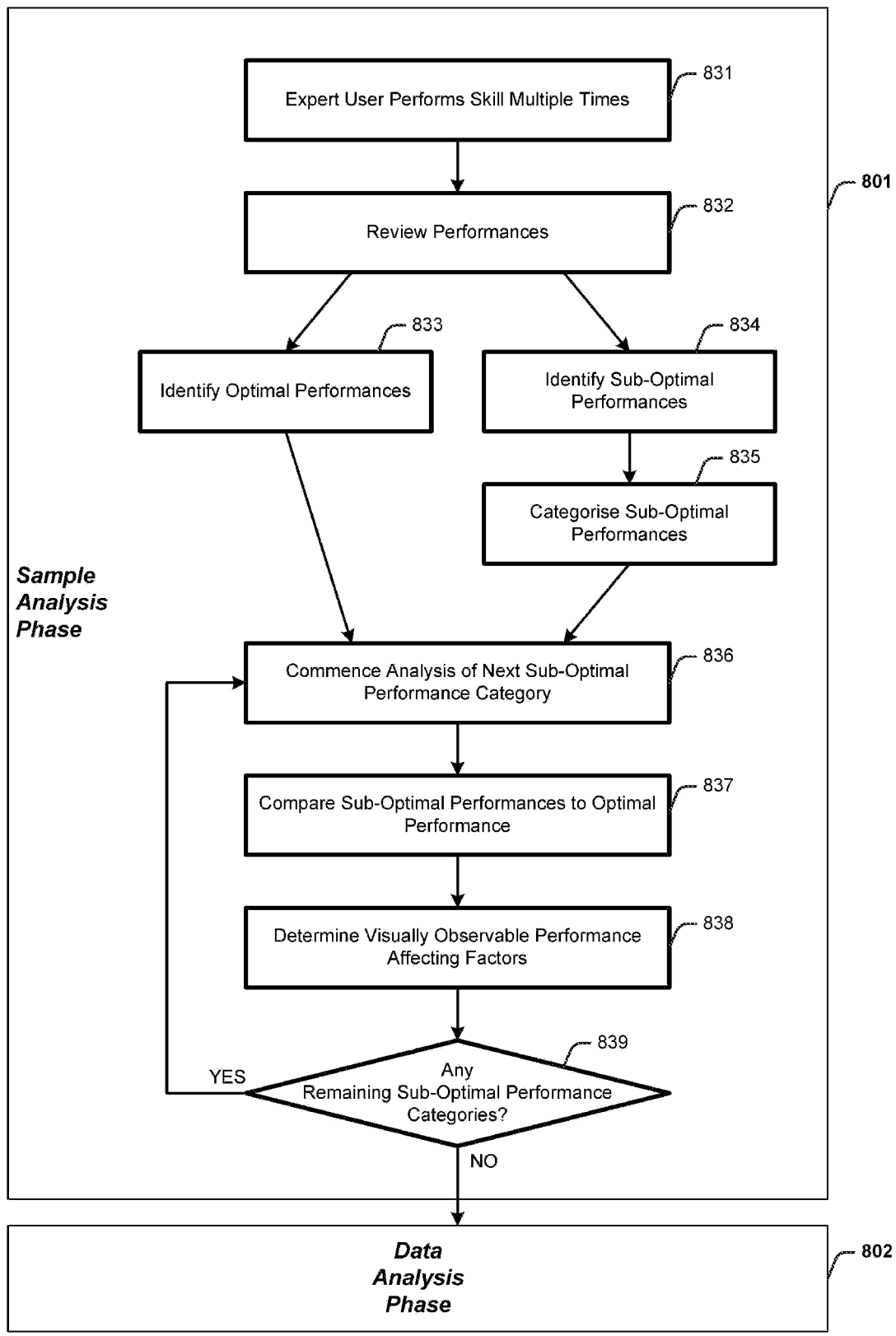
FIG. 8D illustrates a sample analysis phase according to one embodiment.

FIG. 8D illustrates an exemplary method for sample analysis at phase 801, according to one embodiment.

Functional block 831 represents a process including having a subject, in this example being an expert user, perform a given skill multiple times. For example, a sample size of around 100 performances is preferred in some embodiments. However, a range of sample sizes are used among embodiments, and the nature of the skill in some cases influences a required sample size.

Functional block 832 represents a process including review of the multiple performances. This, in the described embodiment, makes use of visually-driven analysis, for example either by way of video review (for example using overlaid video data as described above) or motion capture review (e.g. virtual three dimensional body constructs derived from motion capture techniques, which in some cases include the use of motion sensors).

Based on the review at 832, performances are categorised. This includes identifying optimal performances (block 833), and identifying sub-optimal performances (block 834). The categorisation is preferably based on objective factors. For example, some skills have a one or more quantifiable objectives, such as power, speed, accuracy, and the like. Objective criteria may be defined for any one or more of these. By way of example, accuracy may be quantified by way of a target; if the target is hit, then a performance is "optimal"; if the target is missed, then a performance is "sub-optimal". As another example, a pressure-sensor may determine whether an impact resulting from the performance is of sufficient magnitude as to be "optimal".

Functional block 835 represents a process including categorisation of sub-optimal performances. For example, objective criteria are defined thereby to associate each sub-optimal performance with a category. In one embodiment, where the (or one) objective of a skill is accuracy, multiple "miss zones" are defined. For instance, there is a central target zone, and four "miss" quadrants (upper left, upper right, lower left, lower right). Sub optimal performances are then categorised based on the "miss" quadrant that is hit. Additional criteria may be defined for additional granularity, for example relating to extent of miss, and so on.

Samples from each category of sub-optimal performance are then compared to optimal performance, thereby to identify commonalities in performance error and the like. This is achieved, in the illustrated embodiment via a looped process: a next category is selected at 836, the sub optimal performances of that category are compared to optimal performance at 837, and performance affecting factors are determined at 838. The method then loops based on decision 839, in the case that there are remaining categories of sub-optimal performance to be assessed.

The performance affecting factors determined at 838 are visually identified performance affecting factors which are observed to lead to a sub-optimal performance in the current category. In essence, these allow prediction of an outcome of a given performance based on observance of motion, as opposed to observance of the result. For example, a "miss—lower left quadrant" category might result in a performance affecting factor of "inward tilt of hip during first second of approach". This performance affecting factor is uniquely associated with that category of sub-optimal performance (i.e. consistently observed in samples), and not observed in optimal performances or other categories of sub-optimal performance. Accordingly, the knowledge gained is that where "inward tilt of hip during first second of approach" is observed, it is expected that there will be a miss to the lower left of target.

It will be appreciated that, following phases 802 and 803, this leads to a situation where a software application is able to automatically predict, based purely on worn sensor data, that a given performance is likely to have resulted in a miss to the lower left of target (i.e. based on identifying in sensor data having observable data conditions associated with "inward tilt of hip during first second of approach"). At a practical level, the end-user might be provided with audio feedback from a virtual coach such as "that one missed down and to the left, didn't it? How about you try focussing on XXX next time around". This is a significant result; it enables objective factors that are traditionally observed by visual coaching to be translated into an automated sensor-driven environment.

In some embodiments sample analysis is enhanced by involvement in the visual analysis process by the person providing the sample performances. For example, this may be a well-known star athlete. The athlete may provide his/her own insights as to important performance affecting factors, which ultimately leads to "expert knowledge", which allows a user to engage in training to learn a particular skill based on a specific expert's interpretation of that skill. In this regard, an individual skill may have multiple different expert knowledge variations. As a specific example, a soccer chip kick might have a first expert knowledge variation based on Player X's interpretation of an optimal form of chip kick, and a second expert knowledge variation based on Player Y's interpretation of an optimal form of chip kick. This allows a user to receive not only training in respect of a desired skill, but training based on knowledge of a selected expert in respect of that desired skill (which may in some embodiments provide a user experience similar to being trained by that selected expert).

As context, in relation to expert knowledge, data downloaded to a POD device is selected by a user based on selection of a desired expert knowledge variation. That is, for a selected set of one or more skills, there is a first selectable expert knowledge variation and a second selectable expert knowledge variation.

In some embodiments, for the first selectable expert knowledge variation, the downloadable data configures the client device to identify, in data derived from the set of performance analysis sensors, a first set of observable data conditions associated with a given skill; and for the second selectable expert knowledge variation, the downloadable data configures the client device to identify, in data derived from the set of performance analysis sensors, a second different set of observable data conditions associated with the given skill. For example a difference between the first set of observable data conditions and the second set of observable data conditions accounts for style variances of human experts associated with the respective expert knowledge variations. In other cases a difference between the first set of observable data conditions and the second set of observable data conditions accounts for coaching advice derived from human experts associated with the respective expert knowledge variations.

In some embodiments, for the first selectable expert knowledge variation, the downloadable data configures the client device to provide a first set of feedback data to the user in response to observing defined observable data conditions associated with a given skill; and for the second selectable expert knowledge variation, the downloadable data configures the client device to provide a second different set of feedback data to the user in response to observing defined observable data conditions associated with a given skill. For example, a difference between the first set of feedback data and the second set of feedback data accounts for coaching advice derived from human experts associated with the respective expert knowledge variations. Alternately (or additionally), a difference between the first set of feedback data and the second set of feedback includes different audio data representative of voices of human experts associated with the respective expert knowledge variations.

Alternate Example: Data Analysis Methodology

Figure 8E:
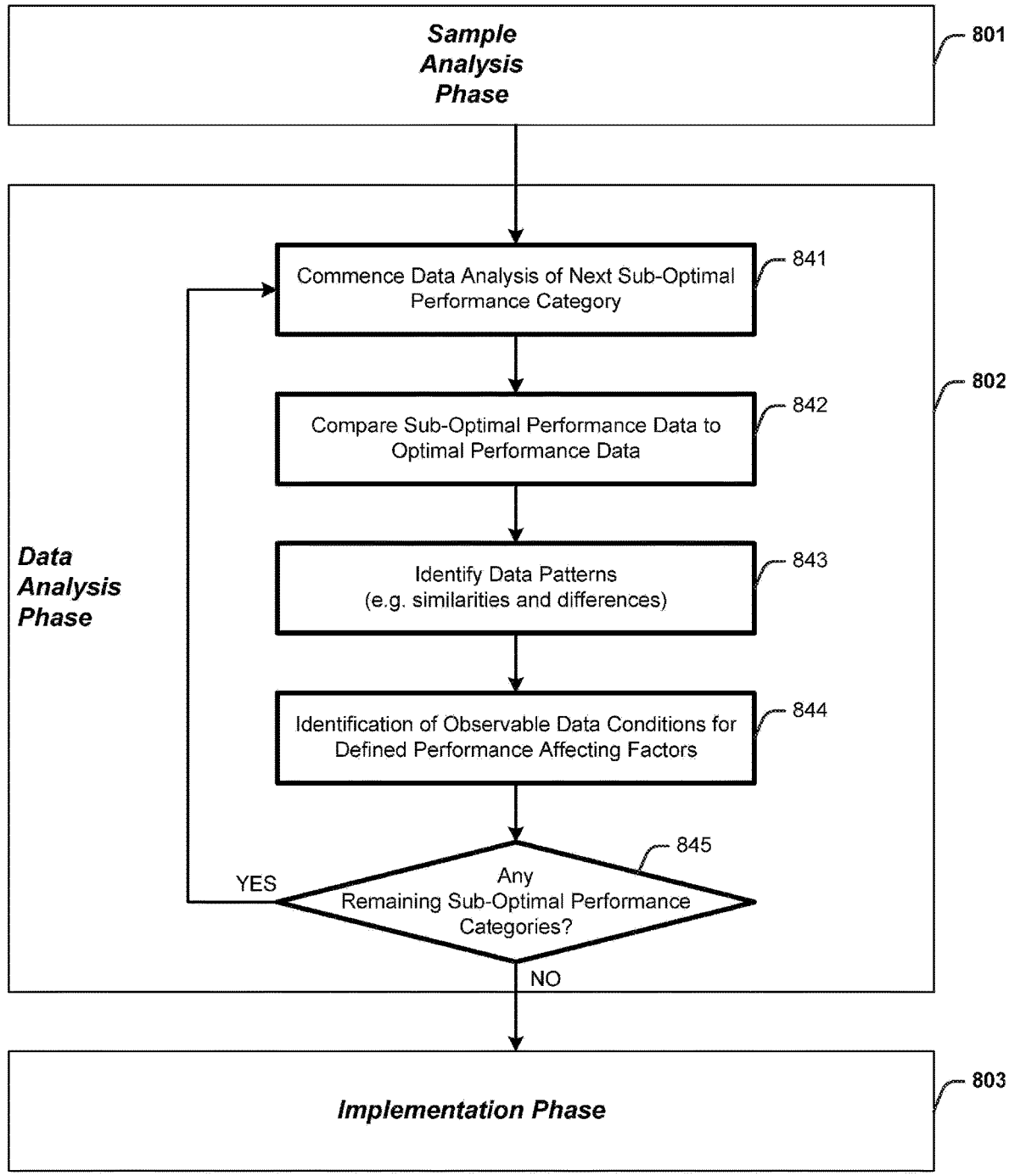
FIG. 8E illustrates a data analysis phase according to one embodiment.

FIG. 8E illustrates an exemplary method for data analysis at phase 802, according to one embodiment. This method is described by reference to analysis of sub-optimal performance categories, for example as defined via the method of FIG. 8D. However, it should be appreciated that a corresponding method may also be performed in respect of an optimal performance (thereby to define observable data conditions associated with optimal performance).

Functional block 841 represents a process including commencing data analysis for a next sub-optimal performance category. Using a performance affecting factor as a guide, comparisons are made at 842 between sub-optimal performance data, for a plurality of sub-optimal performances, to optimal performance data. Data patterns (such as similarities and differences) are identified at 843. In some embodiments, an objective is to identify data characteristics which are common to all of the sub-optimal performances (but not observed in optimal performances in any other sub-optimal categories), and determine how those data characteristics may be relatable to a performance affecting factor. Functional block 844 represents a process including defining, for each performance affecting factor, one or more sets of observable data conditions. The process loops for additional sub-optimal performance categories based on decision 845.

Alternate Example: Implementation Methodology

Figure 8F:
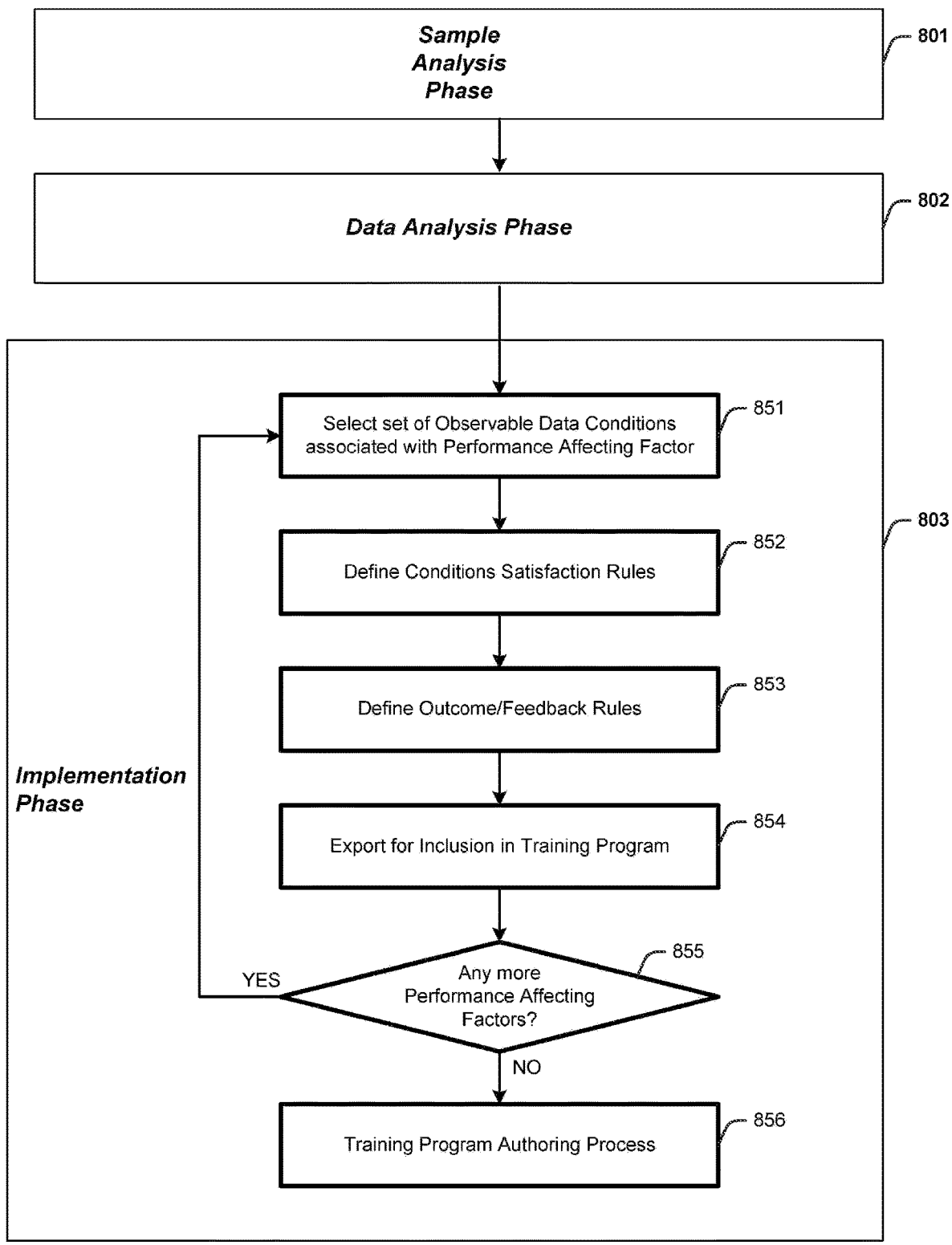
FIG. 8F illustrates an implementation phase according to one embodiment.

FIG. 8F illustrates an exemplary method for implementation at phase 803, according to one embodiment.

Functional block 851 represents a process including selecting a set of observable data conditions, which are associated with a performance affecting factor via phase 801 and 802. Conditions satisfaction rules are set at 851, these defining when, based on inputted sensor data, the selected set of observable data conditions are taken to be satisfied. For example, this may include setting thresholds and the like. Then, functional block 853 includes defining one or more functionalities intended for association with the observable data conditions (such as feedback, direction to alternate activities, and so on). The rule, and associated functionalities are then exported at 854 for utilisation in a training program authoring process at 856. The method loops at decision 855 if more observable data conditions are to be utilised.

A given feedback instruction is preferably defined via consultation with coaches and/or other specialists. It will be appreciated that the feedback instruction need not refer directly to the relevant performance affecting factor. For instance, in the continuing example the feedback instruction may direct a user to focus on a particular task which may indirectly rectify the inward hip tilt (for example via hand positioning, eye positioning, starting stance and so on). In some cases multiple feedback instructions may be associated with a given set of observable data conditions, noting that particular feedback instructions may resonate with certain users, but not others.

Alternate Example: Style and Body Attribute Normalisation

In some embodiments, performances multiple sample users are observed at phase 801 and 802 thereby to assist in identifying (and in some cases normalising for) effects of style and body attribute.

As context, different users will inherently perform a given skill slightly differently. In some cases the difference are a result of personal style. However, in spite of elements attributable to style, there is typically a significant overlap in similarities. Some embodiments compare the performances of multiple subjects, at a visual and/or data level, thereby to normalise for style by defining observable data conditions that are common to performance subject in spite of different styles. This leads to style neutrality. Some embodiments alternately or additionally, include comparing the performances of multiple subjects, at a visual and/or data level, thereby to identify observable data conditions specifically attributable to a given subject's style, thereby to enable training programs that are tailored to train a user to follow that particular style (for example, an individual skill may have multiple different expert knowledge variations, which are able to be purchased separately by an end-user).

Body attributes, such as height, limb length, and the like will also in some cases have an impact on observable data conditions. Some embodiments implement an approach whereby a particular end user's body dimensions are determined based on sensor data, and the observable data conditions tailored accordingly (for example by scaling and/or selecting size or size range specific data conditions). Other embodiments implement an approach whereby the observable data conditions are normalised for size, thereby to negate end user body attribute effects.

In some embodiments, the methodology is enhanced to compare the performances of multiple subjects, at a visual and/or data level, thereby to normalise for body attributes by either or both of: (i) defining observable data conditions that are common to performance subject in spite of body attributes; and/or (ii) defining rules to scale one or more attributes of observable data conditions based on known end-user attributes; and/or (iii) defining multiple sets of observable data conditions that are respectively tailored to end-users having particular known body attributes.

Figure 8G:
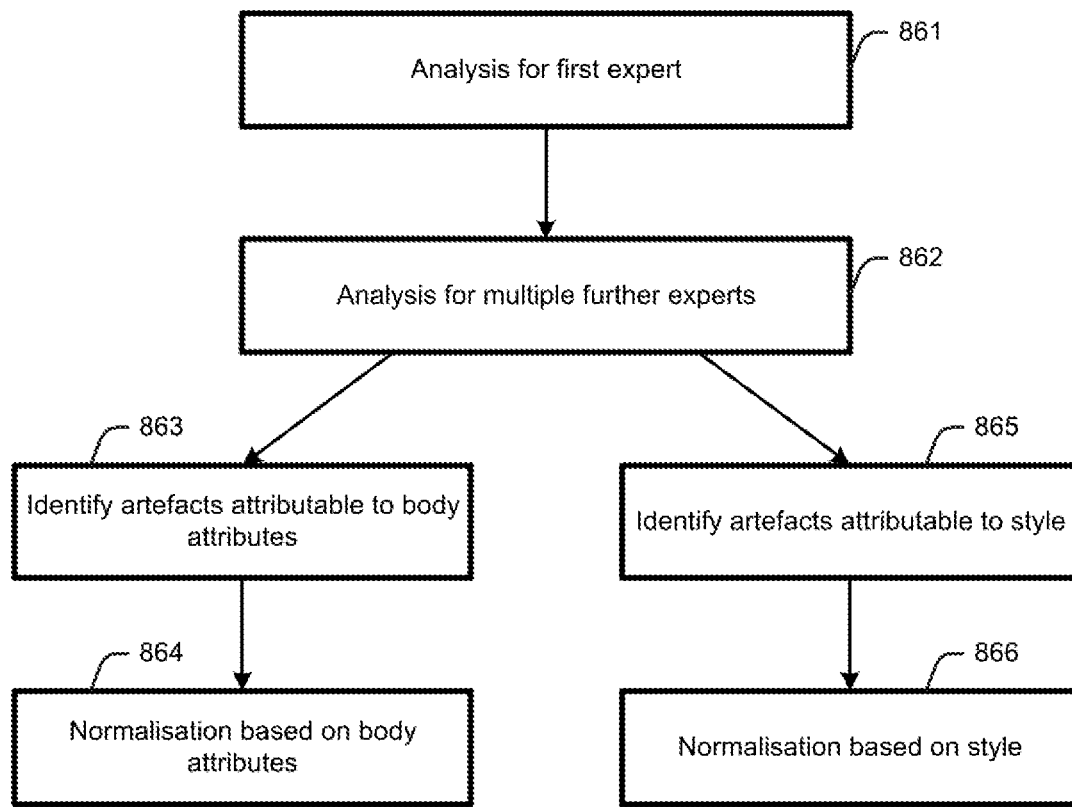
FIG. 8G illustrates a normalisation method according to one embodiment.

FIG. 8G illustrates an exemplary method for body attribute and style normalisation. Elements of this method are performed in respect of either phase 801 and phase 802. Functional block 861 represents performing analysis for a first expert, thereby to provide a comparison point. Then, as represented by block 862, analysis is also performed for multiple further experts of a similar skill level. Functional block 863 represents a processing including identifying artefacts attributable to body attributers, and block 864 represents normalisation based on body attributes. Functional block 865 represents a processing including identifying artefacts attributable to style, and block 864 represents normalisation based on style. In some embodiments either or both forms of normalisation are performed without the initial step of identifying attributable artefacts.

Alternate Example: Application to Multiple Ability Levels

In some embodiments, phases 801 and 802 (and optionally 803) are performed for uses of varying ability levels. The rationale is that an expert is likely to make different mistakes to an amateur or beginner. For example, experts are likely to consistently achieve very close to optimal performance on most occasions, and the training/feedback sought is quite refined in terms of precise movements. On the other hand, a beginner user is likely to make much coarser mistakes, and require feedback in respect of those before refined observations and feedback relevant to an expert would be of much assistance or relevance at all.

Figure 8H:
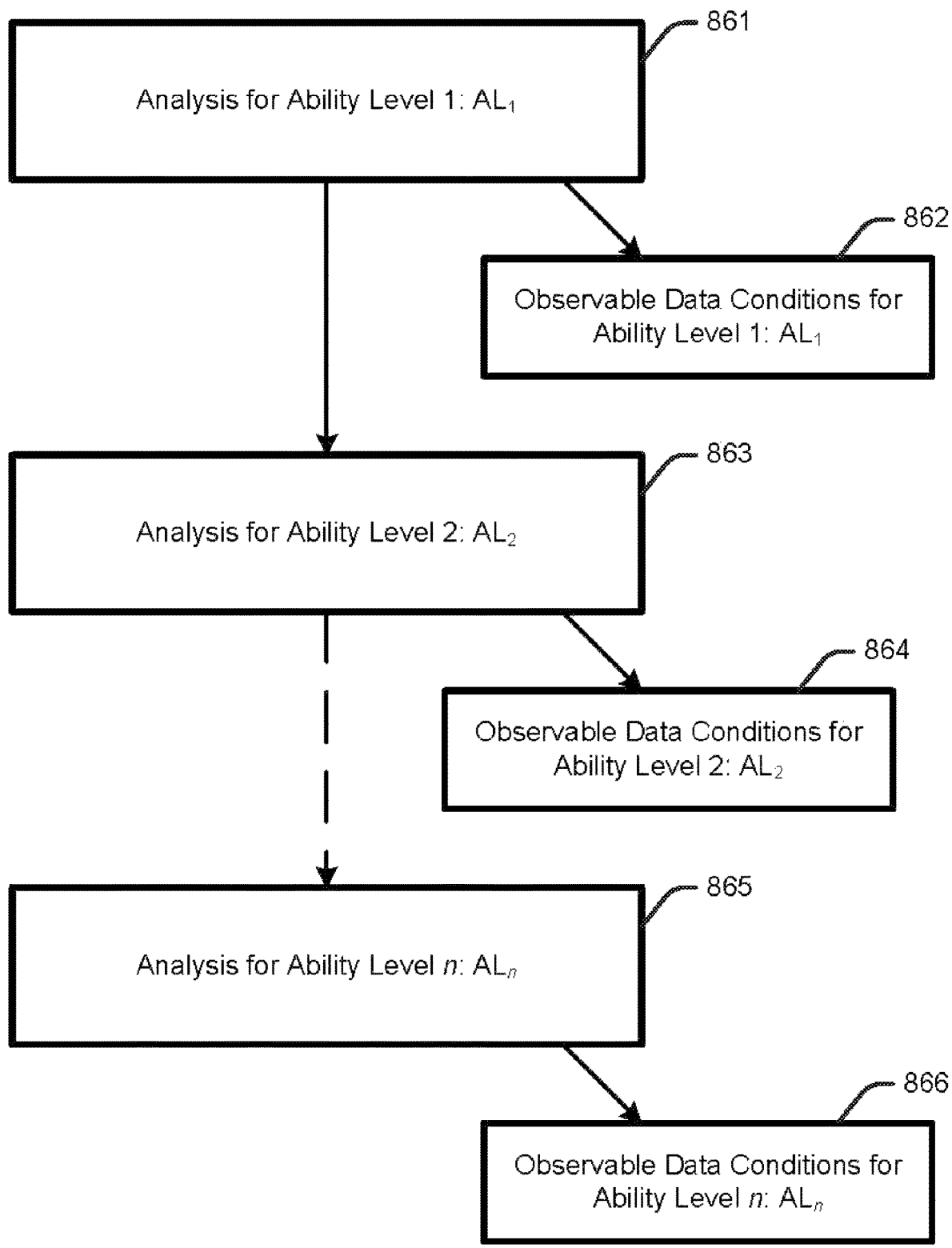
FIG. 8H illustrates an analysis method according to one embodiment.

FIG. 8H illustrates a method according to one embodiment. Functional block 861 represents analysis for an ability level $AL_1$. This in some embodiments includes analysis of multiple samples from multiple subjects, thereby to enable body and/or style normalisation. Observable data conditions for ability level $AL_1$ are outputted at 862. These are repeated, as represented by blocks 863 and 864, for an ability level $AL_2$. The processes are then repeated for any number of ability levels (depending on a level of ability-related granularity desired) up to an ability level $AL_n$ (see blocks 865 and 866).

Figure 8I:
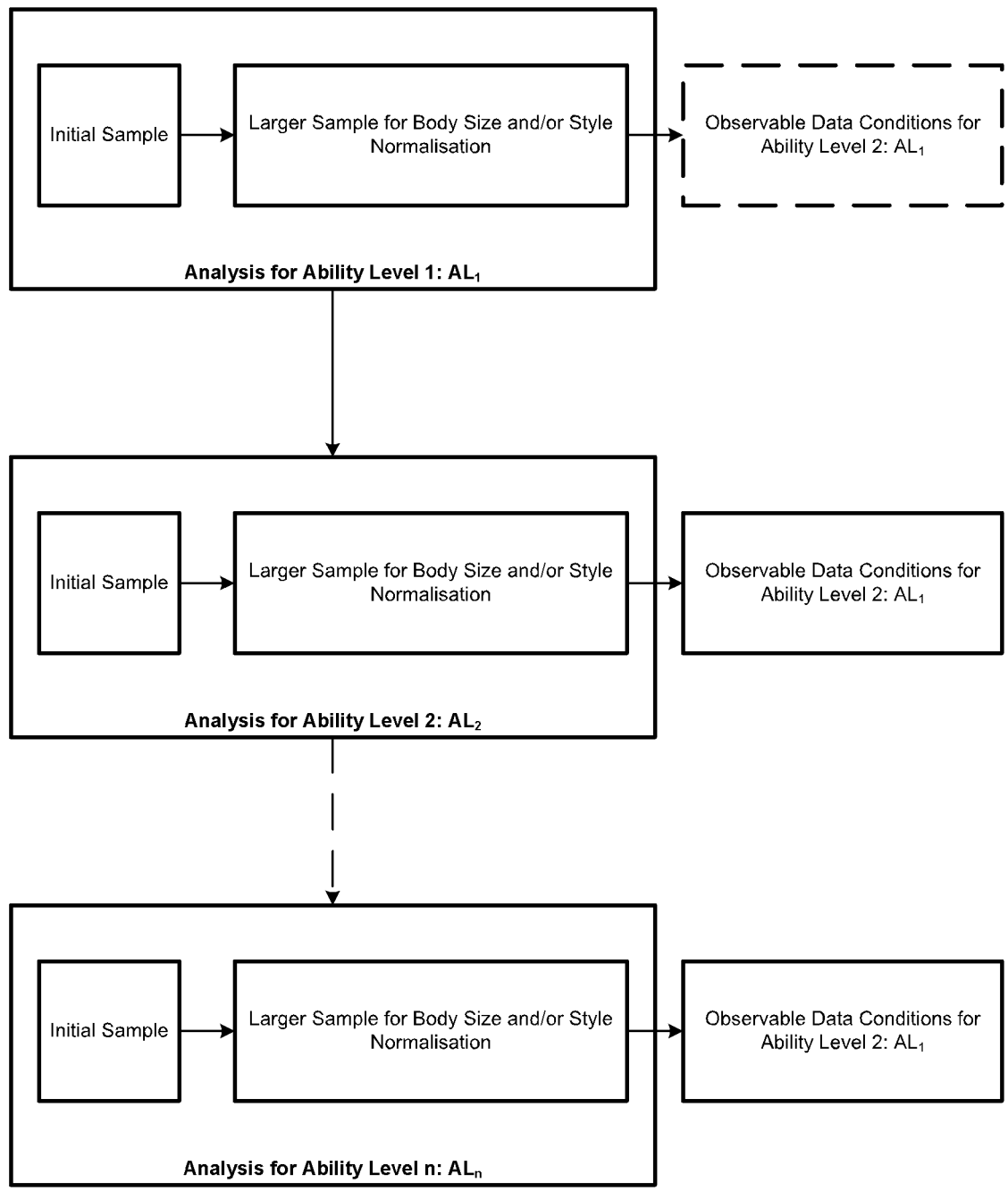
FIG. 8I illustrates an analysis method according to one embodiment.

FIG. 8I illustrates a combination between aspects shown in FIG. 8G and FIG. 8H, such that, for each ability level, an initial sample is taken, and then expanded for body size and/or style normalisation, thereby to provide observable data conditions for each ability level.

Curriculum Construction Phase: Overview

As noted above, following skill analysis phase 100, the example end-to-end framework of FIG. 1B progresses to a curriculum construction phase 110. Detailed aspects of curriculum construction fall outside the scope of the present disclosure; a high-level understanding of approaches for curriculum construction are sufficient for a skilled addressee to understand how this phase plays a role in the overall end-to-end framework.

In general terms, where the end-user functionalities relate to skills training, curriculum construction includes defining logical processes whereby ODCs are used as input to influence the delivery of training content. For example, training program logic is configured to perform functions including but not limited to:

Based on identification of one or more defined ODCs, making a predictive determination in relation to user ability level.

Based on identification of one or more defined ODCs, providing feedback to a user. For example, this may include coaching feedback relevant to a symptom and/or cause of which the ODCs are representative.

Based on identification of one or more defined ODCs, moving to a different portion/phase of a training program. For example, this may include: (i) determining that a given skill (or sub-skill) has been sufficiently mastered, and progressing to a new skill (or sub-skill); or (ii) determining that a user has a particular difficulty, and providing the user with training in respect of a different skill (or sub-skill) that is intended to provide remedial training to address the particular difficulty.

These are an indicative selection only. In essence, the underlying concept is to use ODCs (i.e. data attributes that are able to be identified in MSD, or PSD more generally) thereby to drive functionality in a training program. At a practical level, this enables a wide range of training to be provided, ranging from the likes of assisting a user to improve a gold swing motion, to the likes of assisting a user in mastering a progression of notes when playing a piece of music on a guitar.

It should be appreciated that further embodiments are applicable in context other than skills training, for example in the context of activities (such as competitive activities) that rely upon identification that particular skills have been performed, and attributes of those skills (for example that a particular snowboarding trick has been performed, and an airtime measurement associated with that trick). In such embodiments, ODCs are used for purposes including skill identification and skill attribute measurement.

In some embodiment, feedback provided by the user interface in preferred embodiments includes suggestions on how to modify movement so as to improve performance, or more particularly (in the context of motion sensors) suggestions to more closely so as to replicate motion attributes that are predefined as representing optimal performance. In this regard, a user downloads a training package to learn a particular skill, such as a sporting skill (in some embodiments a training package includes content for a plurality of skills). For example, training packages may relate a wide range of skills, including the likes of soccer (e.g. specific styles of kick), cricket (e.g. specific bowling techniques), skiing/snowboarding (e.g. specific aerial manoeuvres), and so on.

Figure 11A:
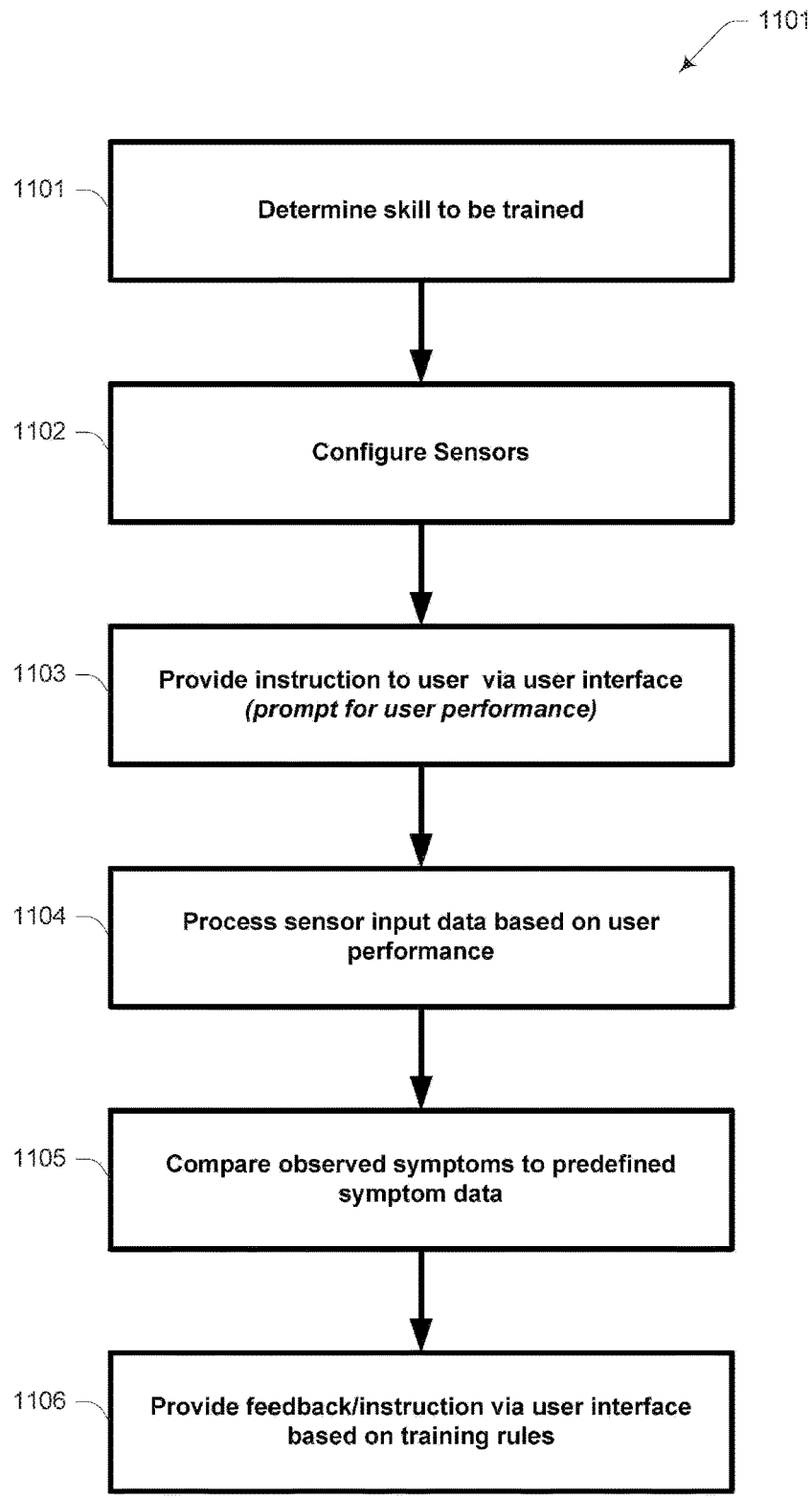
FIG. 11A illustrates a method for operating user equipment according to one embodiment.

In general terms, a common operational process performed by embodiments of the technology disclosed herein is (i) the user interface provides an instruction to perform an action defining or associated with a skill being trained; (ii) the POD device monitor input data from sensors determine symptom model values associated with the user's performance of the action; (iii) the user's performance is analysed; and (iv) a user interface action is performed (for example providing feedback and/or an instruction to try again concentrating on particular aspects of motion). An example is shown in blocks 1103 to 1106 of method 1100 in FIG. 11A.

Performance-based feedback rules are subjectively predefined to configure skills training content to function in an appropriate manner responsive to observed user performance. These rules are defined based on symptoms, and preferably based on deviations between observed symptom model data values and predefined baseline symptom model data values (for example values for optimal performance and/or anticipated incorrect performance. Rules are in some embodiments defined based on deviation in a specified range (or ranges), for a particular symptom (or symptoms), between a specified baseline symptom model data values (or values) and observed values.

In some cases, sets of rules are defined by a content author (or tailored/weighted) specifically for individual experts. That is, expert knowledge is implemented via defined rules.

Figure 11B:
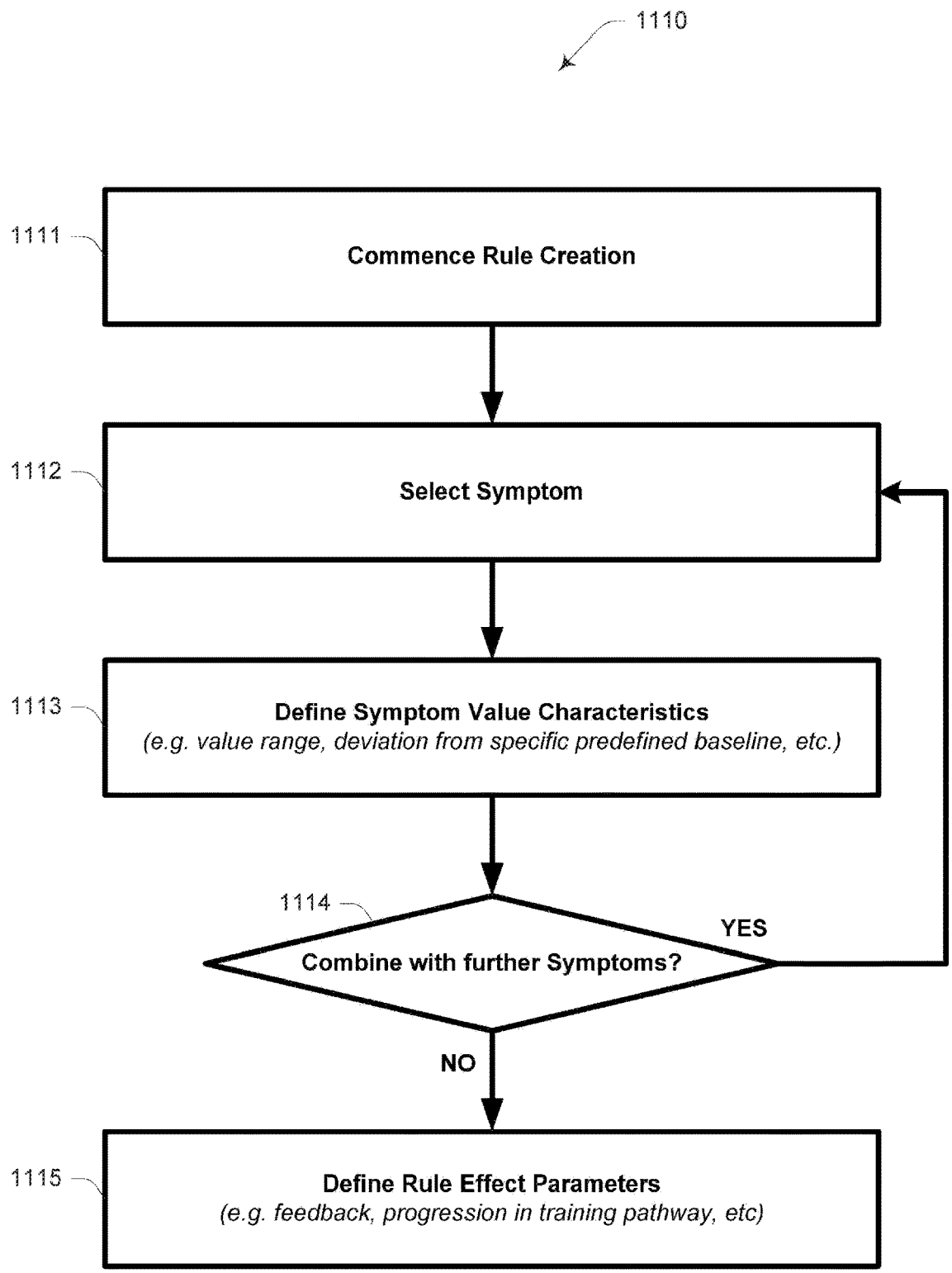
FIG. 11B illustrates a content generation method according to one embodiment.

FIG. 11B illustrates an exemplary method 1110 for defining a performance-based feedback rule. Rule creation is commenced at 1111. Functional block 1112 represents a process including selecting a symptom. For example, this is selected from a set of symptoms that are defined for a skill to which the rule relates. Functional block 1113 represents a process including defining symptom model value characteristics. For example, this includes defining a value range, or a deviation range from a predefined value (for example deviation from a baseline value for optimal or incorrect performance). Decision 1114 represents an ability to combine further symptoms in a single rule (in which case the method loops to 1112). For example, symptoms are able to be combined using "AND", "OR" and other such logical operators.

Functional block 1115 represents a process defining rule effect parameters. That is, blocks 1111-1114 relate to an "IF" component of the rule, and block 1115 to a "THEN" component of the rule. A range of "THEN" component types are available, including one or more of the following:

A rule to provide specific feedback message via the user interface.

A rule to provide one of a selection of specific feedback messages via the user interface (with a secondary determination of which one optionally being based on other factors, for example user historical data).

A rule to provide a specific instruction via the user interface.

A rule to provide one of a selection of specific instructions via the user interface (with a secondary determination of which one optionally being based on other factors, for example user historical data).

A rule to progress to a different stage in a defined progression pathway for a skill or activity.

A rule to progress to one of a selection of different stages in a defined progression pathway (with a secondary determination of which one optionally being based on other factors, for example user historical data).

A rule to suggest downloading of specific content to the POD device (for example content for training in respect of a different skill or activity).

It will be appreciated that these are examples only, and embodiments optionally implement complex arrangements allowing flexible and potentially complex rule defining capabilities.

In some embodiments, rules are integrated into a dynamic progression pathway, which adapts based on attributes of a user. Some examples are discussed further below. As context, observations and feedback are not linked by one-to-one relationships; a given performance observation (i.e. set of observed symptom model values) may be associated with multiple possible effects depending on user attributes. An important example is "frustration mitigation", which prevents a user from being stuck in a loop of repeating a mistake and receiving the same feedback. Instead, after a threshold number of failed attempts to perform in an instructed manner, an alternate approach is implemented (for example different feedback, commencing a different task at which the user is more likely to succeed, and so on).

The feedback provided by the user interface is in some embodiments configured to adapt based on either or both of the following user attributes: These user attributes in some cases include one or more of the following:

Previous user performance. If a user has unsuccessfully attempted a skill multiple times, then the user interface adapts by providing the user with different feedback, a different skill (or sub-skill) to attempt, or the like. This is preferably structured to reduce user frustration, by preventing situations where a user repeatedly fails at achieving a specific outcome.

User learning style. For example, different feedback/instruction styles are in some cases provided to users based on the users' identified preferred learning styles. The preferred learning style is in some cases algorithmically determined, and in some cases set by the user via a preference selection interface.

User ability level. In some embodiments feedback pathways account for a user's ability level (which in this context is a user-set preference). In this manner, feedback provided to a user of a first ability level may differ to feedback provided to a user in respect of another ability level. This is used to, by way of example, allow different levels of refinement in training to be provided to amateur athletes as compared to elite level athletes.

Some embodiments provide technological frameworks for enabling content generation making use of such adaptive feedback principles.

Figure 16:
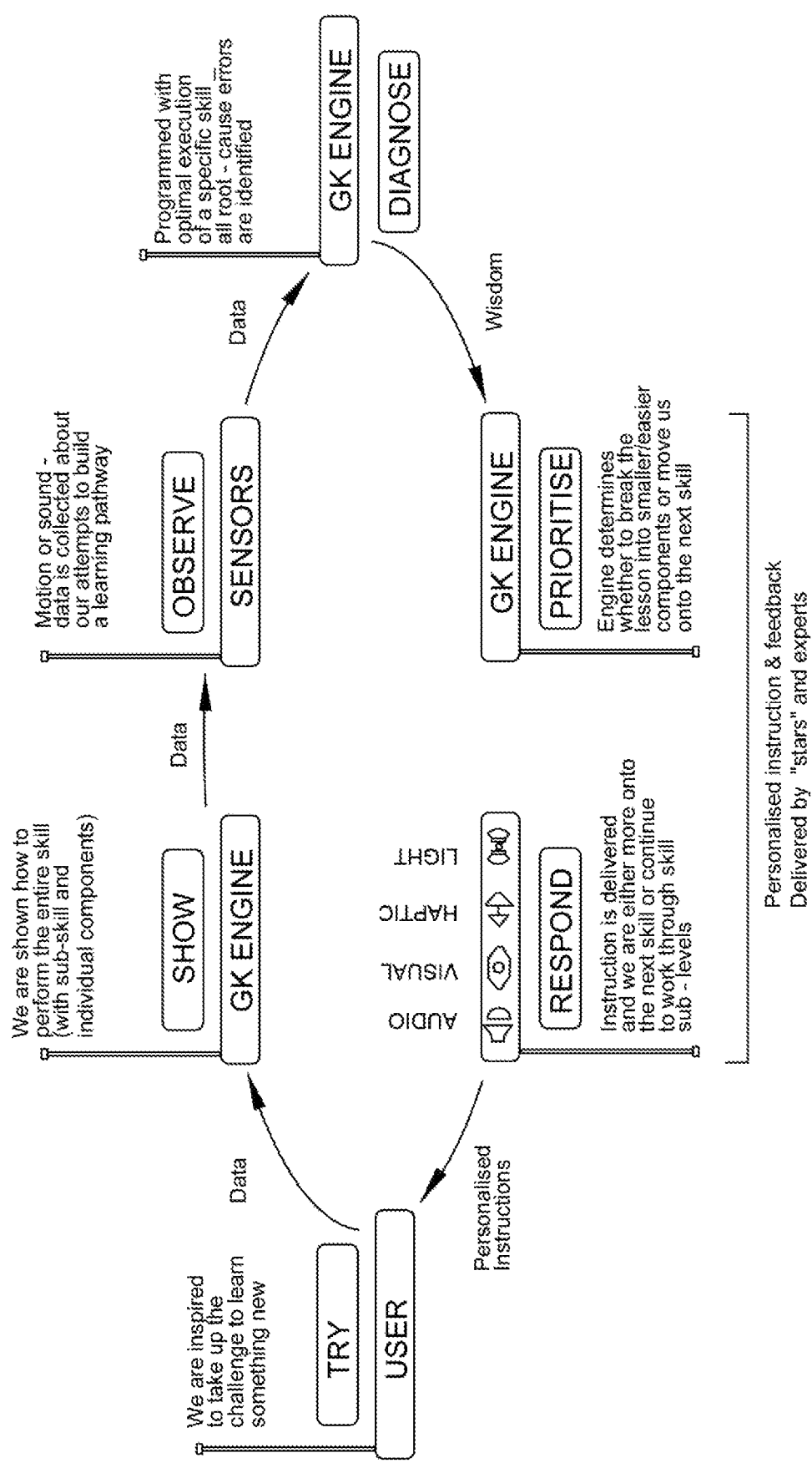
FIG. 16 illustrates an example instructional loop according to one embodiment.

FIG. 16 provides an example of curriculum operation/implementation according to one embodiment. A user is instructed to try a skill, and shown how it is to be performed. The user's attempted performance is captured by PSUs, and diagnosed using ODCs. An engine is then configured to make feedback determinations, which may include identifying sub-skills that can be taught to make the main skill easier to learn. Feedback is then delivered, and the process loops. Such a "try", "show", "observe", "diagnose", "prioritise" and "respond" loops is used in curricula according to various embodiments.

Example Downloadable Content Data Structures

Following skills analysis and curriculum construction, content is made available for download to end user devices. This is preferably made available via one or more online content marketplaces, which enable users of web-enabled devices to browse available content, and cause downloading of content to their respective devices.

In preferred embodiments, downloadable content includes the following three data types:

(i) Data representative of sensor configuration instructions, also referred to as "sensor configuration data". This is data configured to cause configuration of a set of one or more PSUs to provide sensor data having specified attributes. For example, sensor configuration data includes instruction that cause a given PSU to: adopt an active/inactive state (and/or progress between those states in response to defined prompts); deliver sensor data from one or more of its constituent sensor components based on a defined protocol (for example a sampling rate and/or resolution). A given training program may include multiple sets of sensor configuration data, which are applied for respective exercises (or in response to in-program events which prompt particular forms of ODC monitoring). In some embodiments, multiple sets of sensor configuration data are defined to be respectively optimised for identifying particular ODCs in different arrangements of end-user hardware. For example, some arrangements of end user hardware may have additional PSUs, and/or more advanced PSUs. In preferred embodiments, sensor configuration data is defined thereby to optimise the data delivered by PSUs to increase efficiency in data processing when monitoring for ODCs. That is, where a particular element of content monitors for n particular ODCs, the sensor configuration data is defined to remove aspects of sensor data that is superfluous to identification of those ODCs.

(ii) State engine data, which configures a performance analysis device for example a POD device) to process input data received from one or more of the set of connected sensors thereby to analyse a physical performance that is sensed by the one or more of the set of connected sensors. Importantly, this includes monitoring for a set of one or more ODCs that are relevant to the content being delivered. For example, content is driven by logic that is based upon observation of particular ODCs in data delivered by PSUs.

(iii) User interface data, which configures the performance analysis device to provide feedback and instructions to a user in response to the analysis of the physical performance (for example delivering of a curriculum including training program data). In some embodiments the user interface data is at least in part downloaded periodically from a web server.

The manner in which downloadable content is delivered to end user devices varies between embodiments, for instance based upon the nature of end user hardware devices, cloud-based data organisational frameworks, and so on. Various examples are described below.

In relation to sensor configuration data, the content data includes computer readable code that enables the POD device (or another device) to configure a set of PSUs to provide data in a defined manner which is optimised for that specific skill (or set of skills). This is relevant in the context of reducing the amount of processing that is performed at the POD device; the amount of data provided by sensors is reduced based on what is actually required to identify symptoms of a specific skill or skills that are being trained. For example, this may include:

Selectively (and in some cases dynamically) activating/deactivating one or more of the sensors.
Setting sampling rates for individual sensors.
Setting data transmission rates and/or data batching sequences for individual sensors.
Configuring a sensor to provide only a subset of data it collects.

The POD device provides configuration instructions to the sensors based on a skill that is to be trained, and subsequently receives data from the sensor or sensors based on the applied configurations (see, by way of example, functional blocks 1101 and 1102 in FIG. 11A) so as to allow delivery of a PSU-driven training program.

The sensor configuration data in some cases includes various portions that loaded onto the POD device at different times. For example, the POD device may include a first set of such code (for example in its firmware) which is generic across all sensor configurations, which is supplemented by one or more additional sets of code (which may be downloaded concurrently or at different times) which in a graduated manner increase the specificity by which sensor configuration is implemented. For example, one approach is to have base-level instructions, instructions specific to a particular set of MSUs, and instructions specific to configuration of those MSUs for a specific skill that is being trained.

Sensors are preferably configured based on specific monitoring requirements for a skill in respect of which training content is delivered. This is in some cases specific to a specific motion-based skill that is being trained, or even to a specific attribute of a motion-based skill that is being trained.

In some embodiments, state engine data configures the POD device in respect of how to process data obtained from connected sensors (i.e. PSD) based on a given skill that is being trained. In some embodiments, each skill is associated with a set of ODCs (which are optionally each representative of symptoms), and the state engine data configures the POD device to process sensor data thereby to make objective determinations of a user's performance based on observation of particular ODCs. In some embodiments this includes identifying the presence of a particular ODC, and then determining that an associated symptom is present. In some cases this subsequently triggers secondary analysis to identify an ODC that is representative of one of a set of causes associated with that symptom. In other embodiments, the analysis includes determinations based on variations between (i) symptom model data determined from sensor data based on the user's performance; and (ii) predefined baseline symptom model data values. This is used, for example, to enable comparison of the user's performance in respect of each symptom with predefined characteristics.

User interface data in some embodiments includes data that is rendered thereby to provide graphical content that is rendered via a user interface. In some embodiments such data is maintained on the POD device (for example video data is streamed from the POD device to a user interface device, such as a smartphone or other display). In other embodiments data defining graphical content for rendering via the user interface is stored elsewhere, including (i) on a smartphone; or (ii) at a cloud-hosted location.

User interface data additionally includes data configured to cause execution of an adaptive training program. This includes logic/rules that are responsive to input including PSD (for example ODCs derived from MSD) and other factors (for example user attributes such as ability levels, learning style, and mental/physical state). In some embodiments, the download of such data enables operation in an offline mode, whereby no active Internet connection is required in order for a user to participate in a training program.

Delivery of Expert Knowledge Variations

In some embodiments, skills training content is structured (at least in respect of some skills) to enable user selection of both (i) a desired skill; and (ii) a desired set of "expert knowledge" in relation to that skill.

At a high level, "expert knowledge" allows a user to engage in training to learn a particular skill based on a specific expert's interpretation of that skill. In this regard, an individual skill may have multiple different expert knowledge variations. As a specific example, a soccer chip kick might have a first expert knowledge variation based on Player X's interpretation of an optimal form of chip kick, and a second expert knowledge variation based on Player Y's interpretation of an optimal form of chip kick. This allows a user to receive not only training in respect of a desired skill, but training based on knowledge of a selected expert in respect of that desired skill (which may in some embodiments provide a user experience similar to being trained by that selected expert).

From a technological perspective, expert knowledge is delivered by way of any one or more of the following:

(i) Defining expert specific ODCs. That is, the way in which particular trigger data (such as symptoms and/or causes) is identified are specific to a given expert. For instance, a given expert may have a view that differs from a consensus view as to how a particular symptom is to be observed and/or defined. Additionally, symptoms and/or causes may be defined on an expert-specific basis (i.e. a particular expert identifies a symptom that is not part of the ordinary consensus).

(ii) Defining expert-specific mapping of symptoms to causes. For example, there may be a consensus view of a set of causes that may be responsible for a given observed symptom, and one or more additional expert-specific causes. This allows expert knowledge to be implemented, for example, where a particular expert looks for something outside of consensus wisdom that can be the root cause of a symptom.

(iii) Defining expert-specific training data, such as feedback and training program logic. For example, the advice given by a particular expert to address a particular symptom/cause may be specific to the expert, and/or expert-specific remedial training exercises may be defined.

In this manner, expert knowledge is able to be implemented via technology thereby to deliver expert-specific adaptive training programs.

Expert knowledge may be implemented, by way of example, to enable expert-specific tailoring based on any one or more of the following:

Expert style. For example, ODCs, mapping and/or feedback is defined to assist a user in learning to perform an activity in a style associated with a given expert. This is relevant, for instance, in the context of action sports where a particular manoeuvre is performed with very different visual styles by different athletes, and one particular style is viewed by a user as being preferable.

Expert coaching knowledge. For example, ODCs, mapping and/or feedback is defined thereby to provide a user with access to coaching knowledge specific to an expert. For example, it is based upon what the particular expert views as being significant and/or important.

Expert coaching style. For example, ODCs, mapping and/or feedback is defined to provide a training program that replicates a coaching style specific to the particular expert.

Sets of training data that include data that is specific to a given expert (for example ODCs, mapping and/or feedback data) are referred to as "expert knowledge variations". A particular skill in some cases has multiple sets of expert knowledge variations available for download.

In further embodiments, expert knowledge is implemented via expert-specific baseline symptom model data values for optimal performance (and optionally also via baseline symptom model data values also include values for anticipated incorrect performance). This enables comparison between measured symptoms with expert-specific baseline symptom model values, thereby to objectively assess a deviation between how a user has actually performed with, for example, what the particular expert regards as being optimal performance. As a specific example, a soccer chip kick might have a first expert knowledge variation based on Player X's interpretation of an optimal form of chip kick, and a second expert knowledge variation based on Player Y's interpretation of an optimal form of chip kick. This allows a user to receive not only training in respect of a desired skill, but training from a selected expert in respect of that desired skill.

One category embodiment provides a computer implemented method for enabling a user to configure operation of local performance monitoring hardware devices. The method includes: (i) providing an interface configured to enable a user of a client device to select a set of downloadable content, wherein the set of downloadable content relates to one or more skills; and (ii) enabling the user to cause downloading of data representative of at least a portion of the selected set of downloadable content to local performance monitoring hardware associated with the user. For example, a server device provides an interface (such as an interface accessed by a client terminal via a web browser application or proprietary software), and a user of a client terminal accesses that interface. In some cases this is an interface that allows the browsing of available content, and/or access to content description pages that are made available via hyperlinks (including hyperlinks on third party web pages). In this regard, in some cases the interface is an interface that provides client access to a content marketplace.

The downloading in some cases occurs based on a user instruction. For example, a user in some cases performs an initial process by which content is selected (and purchased/procured), and a subsequent process whereby the content (or part thereof) is actually downloaded to user hardware. For instance, in some cases a user has a library of purchased content which is maintained in a cloud-hosted arrangement, and selects particular content to be downloaded to local storage on an as-required basis. As practical context, a user may have purchased training programs for both soccer and golf, and on a given day wish to make use of the golf content exclusively (and hence download the relevant portions of code necessary for execution of the golf content).

The downloading includes downloading of: (i) sensor configuration data, wherein the sensor configuration data includes data that configures a set of one or more performance sensor units to operate in a defined manner thereby to provide data representative of an attempted performance of a particular skill; (ii) state engine data, wherein the state engine data includes data that is configured to enable a processing device to identify attributes of the attempted performance of the particular skill based on the data provided by the set of one or more performance sensor units; and (iii) user interface data, wherein the user interface data includes data configured to enable operation of a user interface based on the identified attributes of the attempted performance of the particular skill.

It will be appreciated that not all data defining a particular training program need be downloaded at any one time. For example, where user hardware is configured to maintain Internet connectivity, additional portions of content may be downloaded on an as-required basis. However, in some cases user hardware is configured to operate in an offline mode, and as such all data required to enable execution of content is downloaded to local hardware. This is particularly relevant in the context of user interface data in the form of instructional videos. In some cases the downloaded user interface data is representative of web locations from which instruction videos are accessed on an as-required basis (for example via streaming), whereas in other cases downloaded user interface data includes the video data. In some embodiments, richer content (for example streaming videos) are available only for online usage; where a user operates local hardware in an offline mode certain rich media aspects of content are not made available for viewing.

The method further includes enabling the user to select downloadable content defined by an expert knowledge variation for the selected one or more skills, wherein there are multiple expert knowledge variations available for the set of one or more skills. For example, at a practical level, an online marketplace may offer a "standard" level of content, which is not associated with any particular expert, and one or more "premium" levels of content, which are associated with particular experts (for instance as branded content).

Each expert knowledge variation is functionally different from other content offerings for the same skill; for instance the way in which a given attempted performance is analysed varies based on idiosyncrasies of expert knowledge.

In some cases a first expert knowledge variations is associated with a first set of state engine data, and the second expert knowledge variation is associated with a second different set of state engine data. The second different set of state engine data is configured to enable identification of one or more expert-specific attributes of a performance that are not identified using the first set of state engine data. The expert-specific attributes may relate to either or both of:

- A style of performance associated with the expert. For instance, the style of performance is represented by defined attributes of body motion that are observable using data derived from one or more motion sensor units. This enables, by way a practical example in the area of skateboarding, content to offer "learn how to perform a McTwist", "learn how to perform a McTwist in the style of Pro Skater A" and "learn how to perform a McTwist in the style of Pro Skater B".
- Coaching knowledge associated with the expert. For example, the expert-specific attributes are defined based on a process that is configured to objectively define coaching idiosyncrasies (for example as described in examples further above, where expert knowledge is separated from consensus views). This enables, by way a practical example in the area of skateboarding, content to offer "learn how to perform a McTwist", "learn how to perform a McTwist from Pro Skater A" and "learn how to perform a McTwist from Pro Skater B".

There are also cases where expert knowledge variations take into account coaching style, for example where the same advice is given for the same symptoms, but the advice is delivered in a different manner.

In some cases, there is a first selectable expert knowledge variation and a second selectable expert knowledge variation, wherein: (i) for the first selectable expert knowledge variation, the downloadable data configures the client device to identify, in data derived from the set of performance sensor units, a first set of observable data conditions associated with a given skill; and (ii) for the second selectable expert knowledge variation, the downloadable data configures the client device to identify, in data derived from the set of performance sensor units, a second different set of observable data conditions associated with the given skill. Again, this is optionally used to enable implementation of any one or more of style variations, coaching knowledge variations, and/or coaching style variations.

In some cases, there is a first selectable expert knowledge variation and a second selectable expert knowledge variation, wherein: (i) for the first selectable expert knowledge variation, the downloadable data configures the client device to provide a first set of feedback data to the user in response to observing defined observable data conditions associated with a given skill; and (ii) for the second selectable expert knowledge variation, the downloadable data configures the client device to provide a second different set of feedback data to the user in response to observing defined observable data conditions associated with a given skill. Again, this is optionally used to enable implementation of any one or more of style variations, coaching knowledge variations, and/or coaching style variations. In some examples a difference between the first set of feedback data and the second set of feedback includes different audio data representative of voices of human experts associated with the respective expert knowledge variations.

A further embodiment provides a computer implemented method for generating data that is configured to enable the delivery of skills training content for a defined skill, the method including: (i) generating a first set of observable data conditions, wherein the first set includes observable data conditions configured to enable processing of input data derived from one or more performance sensor units, the input data being representative of a physical performance of the defined skill by a user, thereby to identify one or more attributes of the performance; and (ii) generating a second set of observable data conditions, wherein the second set includes observable data conditions configured to enable processing of input data derived from the same one or more performance sensor units, the input data being representative of a physical performance of the defined skill by a user, thereby to identify one or more attributes of the performance. In this embodiment, the second set of observable data conditions includes one or more expert-specific observable data conditions that are absent from the first set of observable data conditions; the one or more expert-specific observable data conditions are incorporated into of an expert knowledge variation of skills training content for the defined skill relative to skills training content generated using only the first set of observable data conditions. The expert knowledge variation of skills training content accounts any one or more of (i) for style variances associated with a particular human expert relative to a baseline skill performance style; (ii) coaching knowledge variances associated with a particular human expert relative to baseline coaching knowledge and (iii) coaching style variances associated with a particular human expert relative to baseline coaching style.

One embodiment provides a computer implemented method for generating data that is configured to enable the delivery of skills training content for a defined skill, the method including: (i) generating a first set of skills training content, wherein the first set of skills training content is configured to enable delivery of a skills training program for the defined skill based on processing of input data derived from one or more performance sensor units, the input data being representative of a physical performance of the defined skill by a user, thereby to identify one or more attributes of the performance; and (ii) generating a second set of skills training content, wherein the second set of skills training content includes observable data conditions configured to enable processing of input data derived from the same one or more performance sensor units, the input data being representative of a physical performance of the defined skill by a user, thereby to identify one or more attributes of the performance. In this embodiment the second set of skills training content is configured to provide, in response to a given set of input data, a different training program effect as compared with the first set of skills training content in response to the same set of input data, such that the second set of skills training content provides an expert knowledge variation of skills training content. Again, the expert knowledge variation of skills training content accounts any one or more of (i) for style variances associated with a particular human expert relative to a baseline skill performance style; (ii) coaching knowledge variances associated with a particular human expert relative to baseline coaching knowledge and (iii) coaching style variances associated with a particular human expert relative to baseline coaching style.

Example Training Process Flow

FIG. 16 illustrates how, in an exemplary embodiment, technology disclosed herein replicates and scales one-on-one expert coaching.

The right teacher can make an incredible difference by guiding and accelerating the learning process. However, successful teaching requires direct two way communication and teachers and coaches are time constrained as to how many students they can meaningfully teach their skills. As a result, often the best coaches work only with professionals, not the general public.

By harnessing the knowledge and experience of expert coaches and teachers, the technology replicates the ability of great coaches to:

Observe and analyse. Data is captured by motion or sound sensors as the user attempts the skill or activity. The POD device identifies the student's ability level to place them in the right level of the curriculum and provide the appropriate analysis.

Diagnose and prioritise. Each set of engine data executed by a POD device is programmed with the knowledge of experts for the optimal execution of a specific skill or activity. The engine compares the user's technique within a skill to the optimal technique for that skill (with a high degree of accuracy) and determines and analyses the variance using error detection algorithms. Engines also preferably differentiate between call root-cause mistakes and different types of top-layer, "shallow" mistakes. This allows the engine to analyse the data captured, compare it to the optimal technique and determine the root-cause of the error.

Respond. The technology then provides real-time personalised instruction and the remedy for the root-cause of the mistake, to move the user forward, as would a real teacher or coach with his or her student. Instruction includes real-time audio and visual instruction where appropriate. Additional instruction interfaces including haptic (vibration) and light (illuminated nodes for garments) are currently being developed.

Show. Instruction is also delivered by gamification and video tutorials and drills that break the skill down into its component parts and focus on the key areas that are holding the user back from progressing to the next level of mastering the skill. Tutorials can be displayed on any WiFi or Bluetooth enabled screen, tablet or smartphone.

Unlike traditional coaching, the technology disclosed herein provides a system that is available anytime the student is ready to learn and represents efficient, affordable and effective access to expert personalised coaching.

Assisted Content Selection

In some embodiments the technology provides a personal curriculum for the user. Users are enabled to build an individually tailored, interactive "playlist" of skills, activities, training tools and associated content.

As the system gathers user data, automated suggestion are made in respect of skills, activities and challenges, based on the user's preferences and ability. This allows assisted construction of curriculums to assist users to achieve desired outcomes.

In some embodiments assisted content selection extends to advertising of third party products/services, for example suggestions of equipment, pro tournaments, accommodation at tournaments as well as other complementary activities such as training schedules and golf films. In this manner, the technology provides a range of revenue opportunities from targeted third party advertising and placement.

Example Content Delivery Methodologies

As noted, in some embodiments, content is made available to users via an online marketplace (for example an online marketplace delivered by a cloud hosted platform. A user accesses that marketplace (for example via a web browser application executing on a personal computer or mobile device), and obtains desired training content. Based on obtained content, the user configures a POD device to perform functionalities including functionalities relating to provision of training in respect of a desired activity and/or skill (for example by causing a server to download code directly to the POD device via the POD device's Internet connection, which may be to a local WiFi network). Based on this configuration, a set of training program rules are able to be executed on the POD device (or in further embodiments a secondary device coupled to the POD device) to provide an interactive training process. The interactive training process provides, to a user, feedback/instructions responsive to input representative of user performance. This input is derived from the PSUs, and processed by the POD device. The interactive training process is in some embodiments operated based on a set of complex rules, which take into consideration: (i) observed user performance attributes relative to predefined performance attributes; (ii) user attribute data, including historical performance data; (iii) a skill training progression pathway (which may be dynamic variable); and (iv) other factors.

The present disclosure focuses primarily on the example of a POD device that receives user performance data derived from a set of motion sensors (for example including wearable motion sensors coupled to garments; the motion sensors being configured to enable analysis of user body position variations in three dimensions). For example, this is particularly applicable to training in respect of physical activities, such as sports and other activities involving human movements. However, the technology is equally applicable in respect of data derived from other forms of sensor. Examples include sensors that monitor audio, video, position, humidity, temperature, pressure, and others. It will be appreciated that data from such sensors may be useful for skills training across a wide range of activity types. For example, audio sensors are particularly useful for training activities such as language skills, singing, and the playing of musical instruments.

At a general level, technology disclosed herein is in some embodiments configured to enable capture of wisdom of experts, and from this replicating the one-on-one conversation between coach and student. In this regard, features in some cases include:

- Two way exchange. The digital technology is versatile and highly scalable and can be applied to virtually any skill or activity. Using sensors and associated technology, there is an ability to teach better with each interaction, adapting to individual users' style and physiology in a real-time coaching experience.
- Real-time instruction. Sensors diagnose mistakes in movement and technique, and enable automated (and substantially instantaneous) delivery of personalised, tactile and/or audiovisual feedback and/or instructions.
- Advanced performance. More than just tracking, users are constantly coached. A resulting measurable lift in performance helps a user hit milestones and reach your goals sooner with greater certainty.

How these features are achieved by various embodiments will be appreciated based on the description herein.

Skills training content is rendered via a user interface (for example in a graphical and/or audible form). As noted above, there are various technical arrangements by which this is achieved. A preferred approach is for training content to be downloaded directly to POD device 150, and rendered via a separate device that includes video and/or audio outputs which allow a user to experience rendered content. The separate device may include one or more of a mobile device such as a smartphone (which in some embodiments executes an application configured to render content provided by POD device 150), a headset, a set of glasses having an integrated display, a retinal display device, and other such user interface devices.

In some embodiments where a mobile device (such as a smartphone) is used, the POD device provides a local web server configured to deliver content to the mobile device. The mobile device executes a web browser application (or in some cases a proprietary app), which navigates to a web address in respect of which code is obtained from the POD device as a local web server.

Skills training content is in preferred embodiments obtained from an online marketplace. This marketplace preferably enables a user to select and procure various different skills training packages, and manage the downloading of those to the user's POD device (or POD devices). The term "skills training package" describes an obtainable set of skills training content. This may relate to a single skill, a variety of skills relating to a common activity, or various other arrangements. The present disclosure should not be limited by reference to any specific implementation option for structuring how skills training data is organised, made available for procurement, monetised, or the like.

Example Content Delivery Frameworks

The following section describes various exemplary technological frameworks for the delivery of content, such as adaptive skills training content which is driven by processing of PSD (such as MSD), to end user devices.

In overview, any one or more of the following approaches, or combinations thereof, may be used:

- Browsing and selection of downloadable content via a first web-enabled device, with content download subsequently being effected to a second web-enabled device. For example, content is browsed via a smartphone, and then caused to be downloaded directly from a web source to a POD device.
- Browsing and selection of downloadable content via a first web-enabled device, with content download subsequently being effected to that first web-enabled device. There may then be a secondary downloading of some or all of the content from the first web-enabled device to a second device, such as a POD device (for instance sensor configuration data and state engine data is first downloaded to a mobile device, and then delivered to a POD device).
- Utilisation of a POD device that is separate from a user interface device. For example, a mobile device is used to provide a user interface, and a POD device is a processing unit mounted in a MSU-enabled garment.
- Utilisation of a POD device that is integrated with a user interface device. For example, in some embodiments a smartphone takes the role of a POD device.
- Utilisation of a POD device that is physically coupled to an existing end-user mobile device. For example, a POD device is defined as a processing unit which couples to a smartphone, for example via a cradle type mount.

Figure 9A:
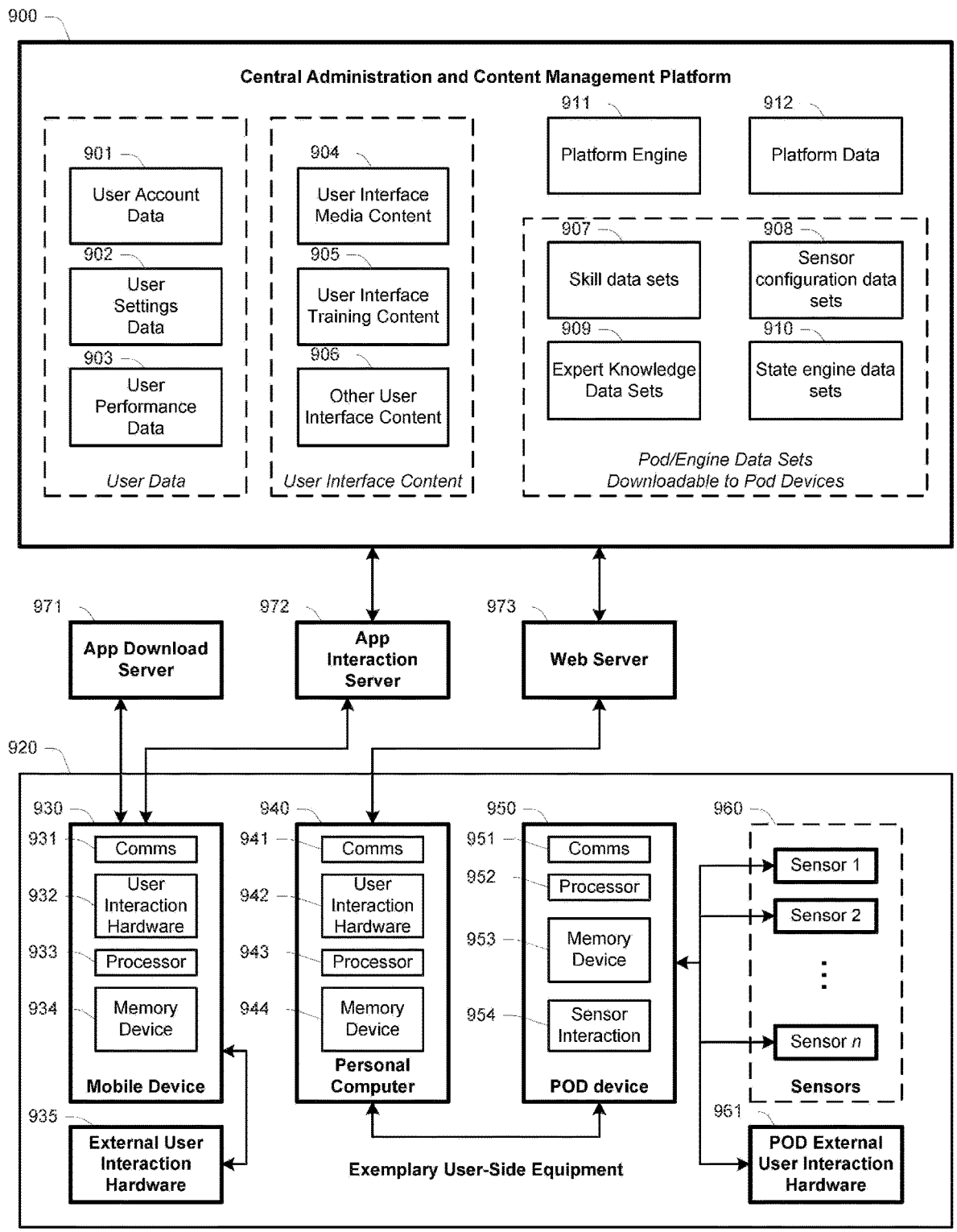
FIG. 9A illustrates an example framework including server-side and client-side components.
Figure 9B:
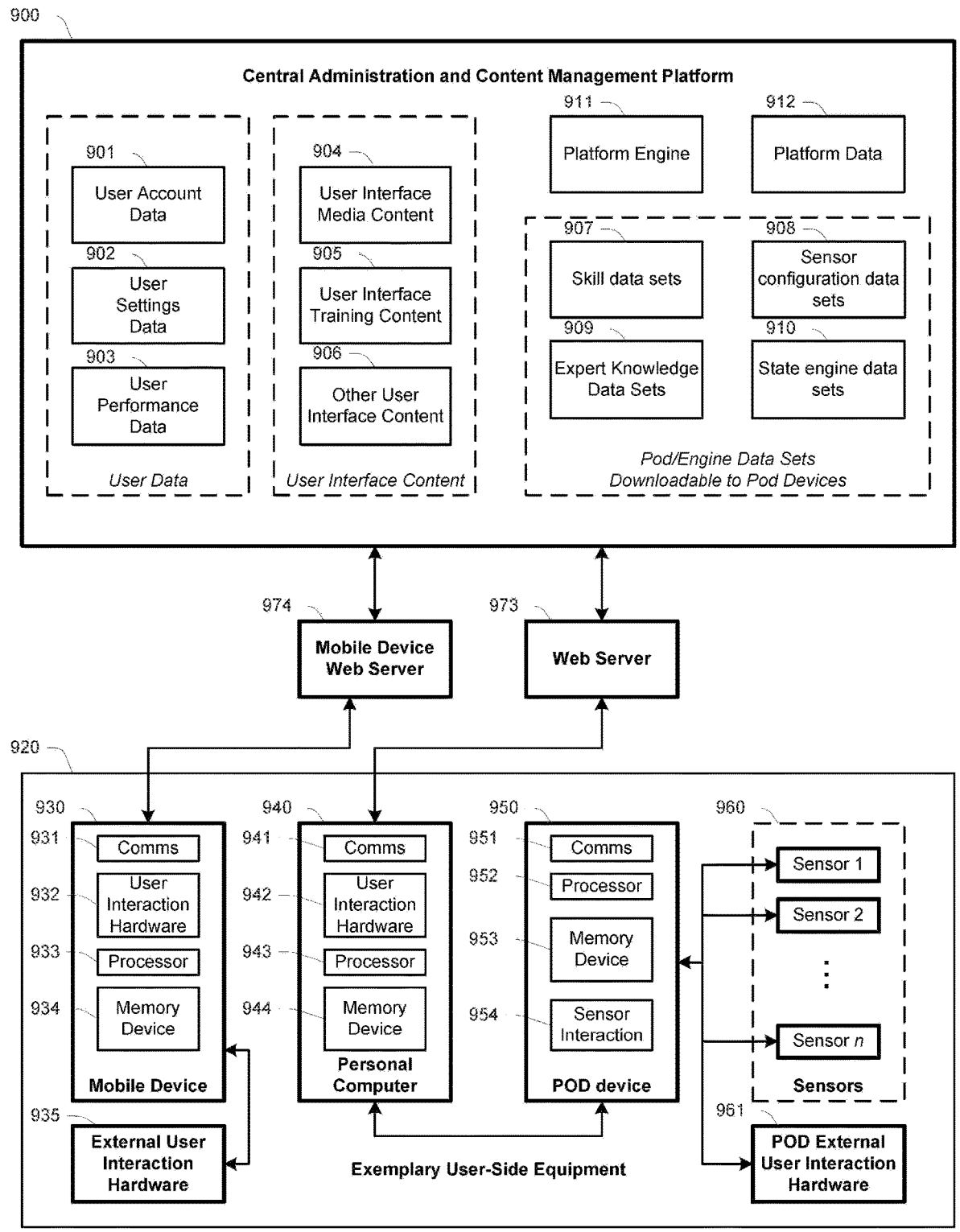
FIG. 9B illustrates a further example framework including server-side and client-side components.
Figure 9C:
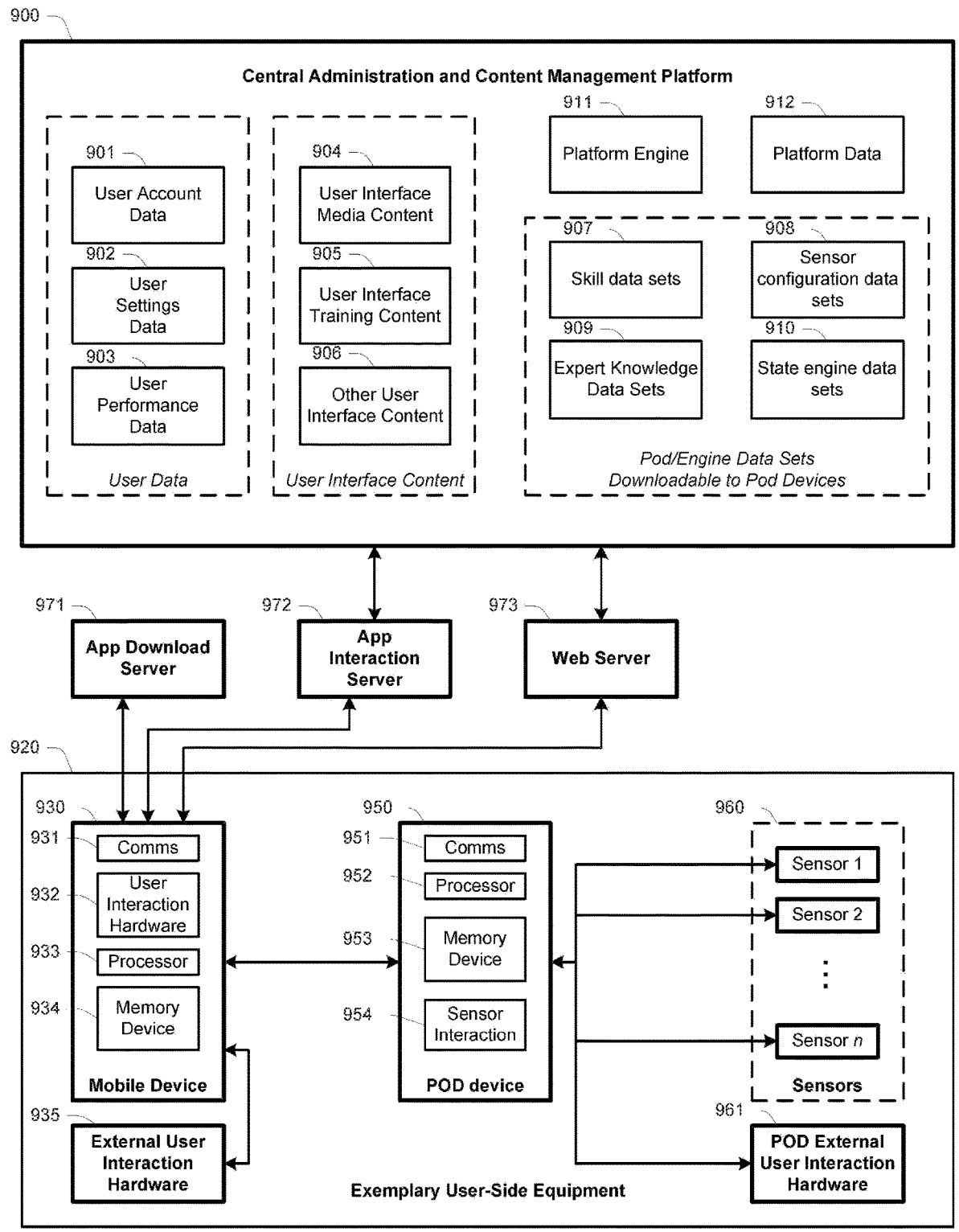
FIG. 9C illustrates a further example framework including server-side and client-side components.
Figure 9D:
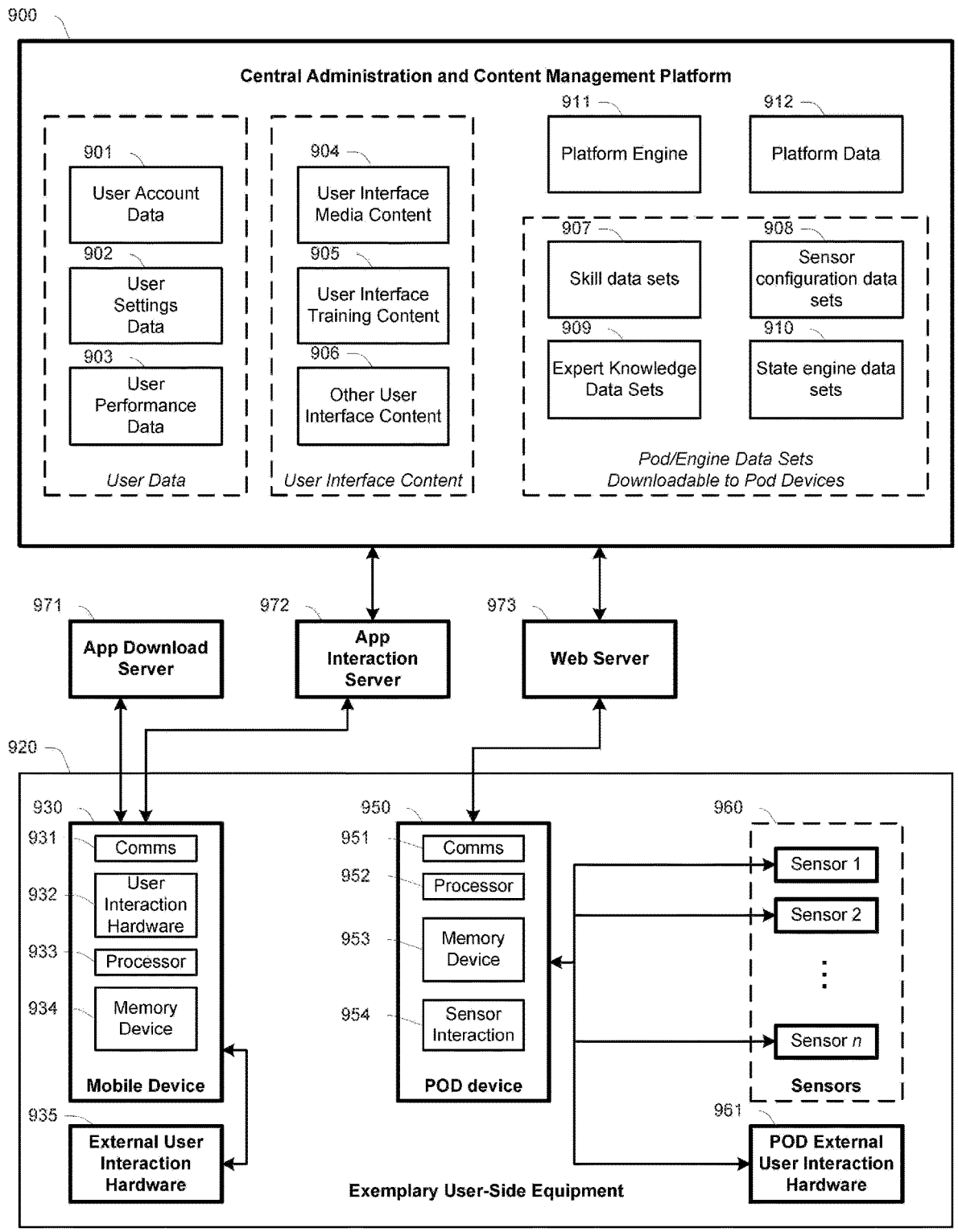
FIG. 9D illustrates a further example framework including server-side and client-side components.

FIG. 9A shows an exemplary computer implemented framework according to one embodiment. Various alternate embodiments are illustrated in FIG. 9B to FIG. 9D, where similar features have been designated corresponding reference numerals.

Each illustrated framework includes multiple computing devices (also referred to as "machines" or "terminals"), which are each configured to provide functionality (for example performance of "computer implemented methods") by executing computer-executable code (which may be stored on a computer-readable carrier medium) via one or more microprocessors (also referred to simply as "processors"). It will be appreciated that the various computing devices include a range of other hardware components, which are not specifically illustrated.

The example of FIG. 9A illustrates a central administration and content management platform 900. This platform is able to be defined by a single computing device (for example a server device), or more preferably by a plurality of networked computing devices. Components of a server are described functionally, without specific reference to various constituent computing devices that are configured to individually or collectively provide the relevant functionalities. It should be appreciated that such matters are an issue of design choice, with a wide range of network and server architectures being well known in the art. Furthermore, in some embodiments there are multiple instances of platform 900 operating in parallel.

Platform 900 is configured to provide functionalities that are accessed by a plurality of users (such as the subjects referred to above) via computing devices operated by those users. FIG. 9A illustrates a set of user-side equipment 920 operated in relation to an exemplary user. In practice, each of a plurality of users operates respective sets of similar equipment 920 (not shown).

Equipment 920 includes a mobile device 930. For example, in this embodiment mobile device 930 takes the form of a Smartphone. However, in other embodiments different mobile devices are used such as a tablet, a PDA, a portable gaming device, or the like. In some embodiments mobile device 930 is defined by purpose-configured hardware, specifically intended to provide functionalities relevant to the described overall framework. In overview, a primary function of mobile device 930 is to deliver, via a user interface, content that is obtained from platform 900. This content is able to be downloaded on an "as required" basis (in an online mode), downloaded in advance (thereby to enable operation in an offline mode), or both.

Mobile device 930 is able to be coupled to one or more pieces of external user interaction hardware, such as external headphones, microphones, a wearable device that provides a graphical display (for example glasses configured to provide augmented reality displays, retina projection displays), and so on.

In the example of FIG. 9A, mobile device 930 is configured to interact with platform 900 via a mobile app (for example an iOS or Android app), which is downloaded from an app download server 971. (In this embodiment server 971 is a third party operated server, although other embodiments make use of first party servers). Such a mobile app is stored on a memory device 934 and executed via a processor 933. The mobile app configures mobile device 930 to communicate with an app interaction server 972 via an available Internet connection, with app interaction server 972 in turn providing a gateway to data available via platform 900.

In the example of FIG. 9B, mobile device 930 is configured to interact with platform 900 via a web browser application, which upon navigation to a predefined web address configures mobile device 930 to communicate with a mobile device web server 974 via an available Internet connection. Web server 974, in turn, provides a gateway to data available via platform 900. The web browser application is executed based on code stored in memory 934 of mobile device 930, and provides a user interface specific to platform 900 via browser-renderable user interface code that is downloaded to device 930 via server 974.

Equipment 920 additionally includes a personal computer (PC) 940. This is able to be substantially any computing device that is correctly and adequately configured to enable a further hardware device, in the form of a POD device 950, to communicate with platform 900. For example, in one embodiment the POD device connects to PC 940 via a wired connection (such as a USB connection) or a wireless connection (such as a WiFi or a Bluetooth connection). Functionally, this allows downloading of data from platform 900 to POD device 950. Alternate arrangements and connections are able to be implemented thereby to enable communications between POD device 950, for example:

POD device 950 accessing platform 900 via mobile service 930, and a web server 973 (see FIG. 9C). This involves accessing specific functionalities of device 930 relevant to operation of POD device 950 or, in some embodiments, merely accessing an Internet connection provided through mobile device 930.

POD device 950 accessing platform 900 via web server 973 (see FIG. 9D).

In some such cases, for example where POD device 950 does not inherently provide a user interface, a given user operates mobile device 930 (or another suitable configured computing device) to access a user interface (for example via a mobile app or a web page), thereby to instruct platform 900 to deliver particular data to a POD device 950 associated with that user. In such an embodiment the data is directly downloaded to POD device 950 via an available Internet connection.

In some embodiments, skills training content to be rendered on mobile device 930 is first downloaded to POD device 950. This is implemented such that mobile device 930 is able to provide skills training data in an offline mode (with no Internet connection), with necessary content being provided by POD device 950. This is particularly relevant in examples where there is no mobile device 930, and the user interface is provided via a user interface delivery device 990 which communicates only with POD device 950 (for example a headset, set of glasses having an inbuilt display, retinal projection device, or the like).

Figure 17:
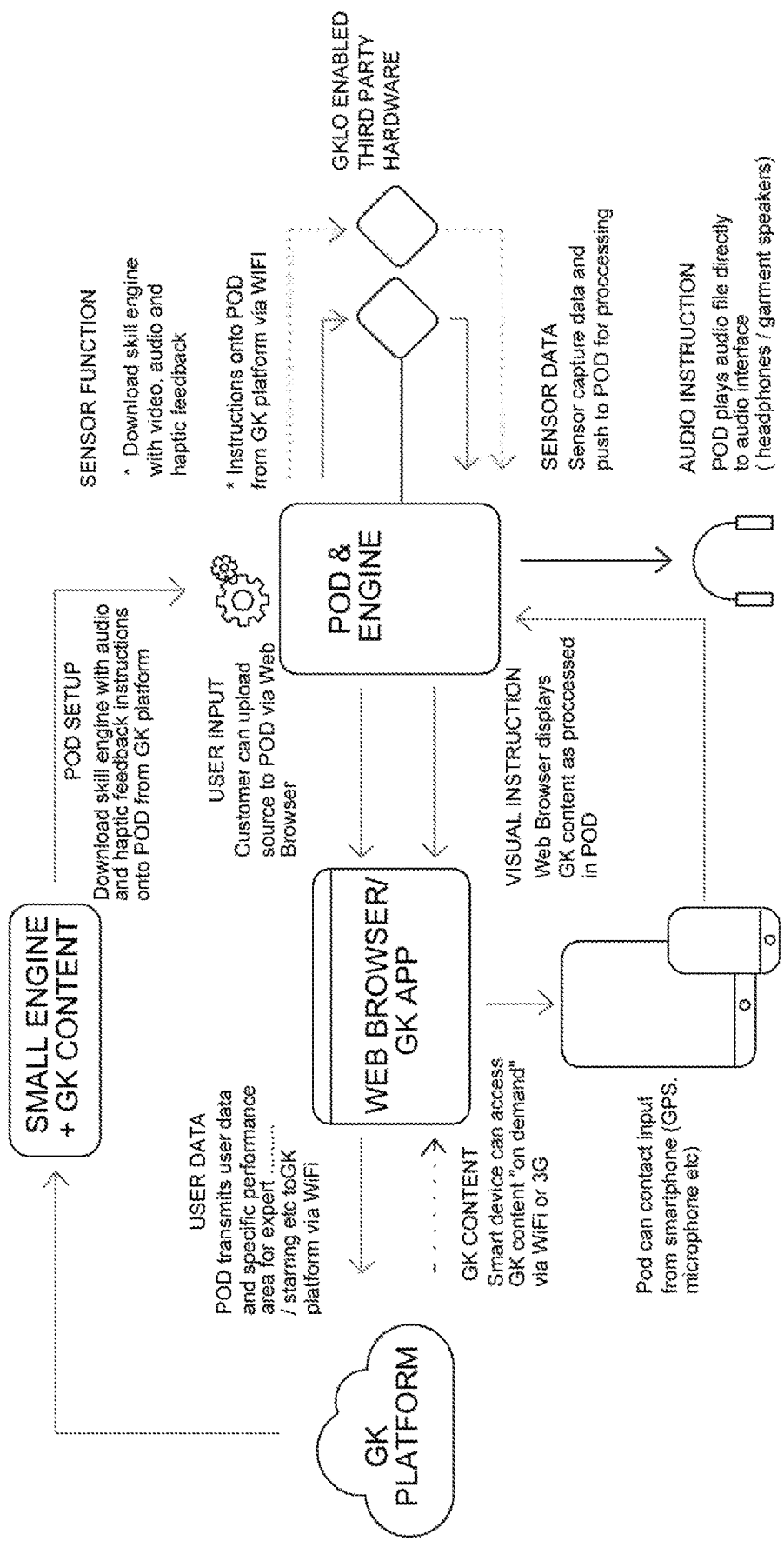
FIG. 17 illustrates a further example framework with process flow.

FIG. 17 schematically illustrates a further framework, with example process flows relevant to that framework.

Exemplary POD Device and Sensor Arrangements

POD device 950 is configured to perform processing of data collected from one or more PSUs 960. These PSUs are connected to POD 950 via wired and/or wireless connections. For example, in one embodiment a POD device is connected to a first set of PSUs via a direct wired coupling, and to a second set of PSUs via a RF-link to a bridging component, the bridging component in turn being connected to the second set of PSUs via a direct wired coupling.

A range of PSUs are used across various embodiments depending upon the nature of the data being collected. In turn, the nature of the data being collected is dependent upon the skill or activity being undertaken by the user. For instance, the following user cases are relevant to a number of examples and embodiments considered herein:

Wearable MSUs. MSUs are integrated into clothing articles (MSU-enabled garments) that are configured to be worn by a subject. Examples of such clothing articles include compression-type clothing (such as a shirt or pants) which each includes a plurality of spaced apart MSUs at known positions. In some cases the clothing includes preformed mounting locations for releasably receiving respective MSUs to enable movement of MSUs between the available mounting locations. In one embodiment, a compression shirt supports a plurality of motion MSUs and has a mounting to complementarily releasably receive a POD device, such that the mounting couples the POD device to the MSUs via wired connections that extend through and which are enveloped by the shirt. The shirt is able to be coupled with a complementary set of compression pants that include further plurality of motion MSUs which are wired to a common RF communication module. That RF communication module communicates MSD to a further RF module provided on the shirt, or by the POD device, thereby to enable the POD device to receive data from all MSUs on the shirt and pants.

ASUs. In different embodiments different audio sensors are used. Examples of available sensors include microphone-based sensors, sensors that plug into audio input ports (for example via 2.5 mm or 3.5 mm jack connectors), thereby to receive audio signals, pickups that generate MIDI signals, and so on.

It will be appreciated that POD device 950 is able to be configured via software to process data from substantially any form of PSU that provides an output signal (for example a digital output signal) that is received by the POD device.

Some embodiments provide multiple different hardware configurations of POD devices, each being manufactured to interact with specific PSUs. For example, exemplary POD devices may include:

A POD device configured to be carried by a garment, which physically couples to a plurality of MSUs also carried by that garment (and in some cases wirelessly couples, directly or indirectly, to one or more further MSUs).

A POD device that includes a microphone.

A POD device that includes an audio input port (such as a 3.5 mm headphone jack).

It will additionally be appreciated that the various forms of PSU allow for training in respect of a wide range of skills. For example, a POD device coupled to one or more ASUs is in some cases used to provide training in various musical skills (for example singing, playing of instruments, and the like).

Example Arrangements for Delivery of User Interface

The manner by which the user interface provides feedback and/or instructions varies based on hardware configurations. In some embodiments the user interface is audio-only (for example using headphones), in which case instructions and feedback are audio-based. In some embodiments the user interface includes visual information, which requires a display screen (for example a display screen provided by a smartphone device, appropriate glasses and/or retinal display devices, and so on).

Figure 10A:
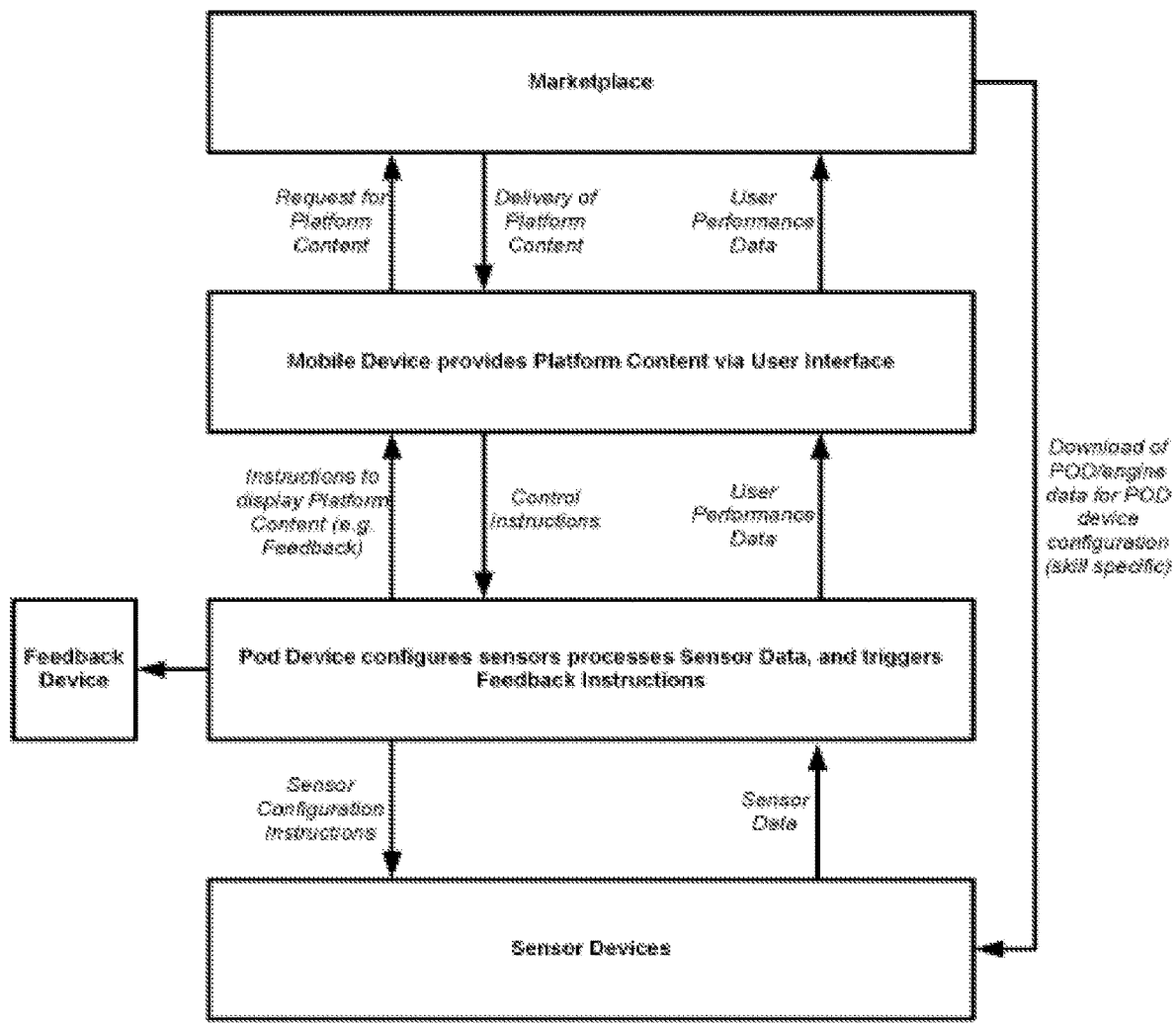
FIG. 10A illustrates operation of an example framework.

The arrangement of user-side equipment in FIG. 9A is able to be configured to function as shown in FIG. 10A. More particularly, a marketplace platform is technically configured for delivering POD/engine data to a POD device to, in turn, allow configuration of the POD device to deliver training content in respect of a specific skill (or set of skills). The POD device is configured to process received data from the sensors based on POD/engine data that was previously downloaded from the marketplace. Based on this processing, the POD device provides instructions to a mobile device to display platform content via its user interface (for example thereby to provide feedback, instruct the user to perform a specific task, and so on). The mobile device downloads platform content, where relevant, from the platform.

A further feedback device is used in other embodiments (for example an audio device, glasses with digital displays, and so on), and in FIG. 10A this is illustrated as being directly coupled to the POD device.

Figure 10B:
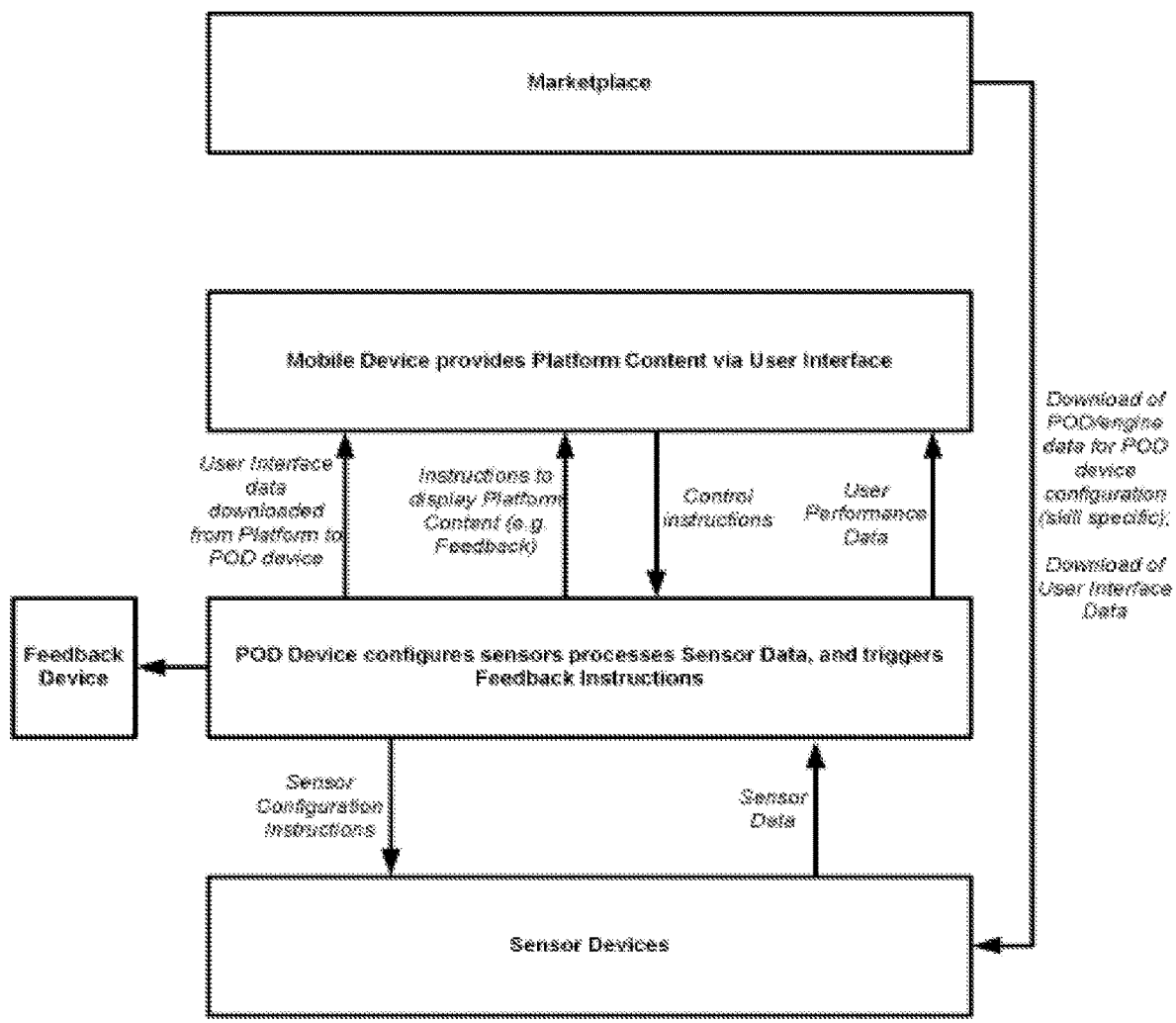
FIG. 10B illustrates operation of a further example framework.
Figure 10C:
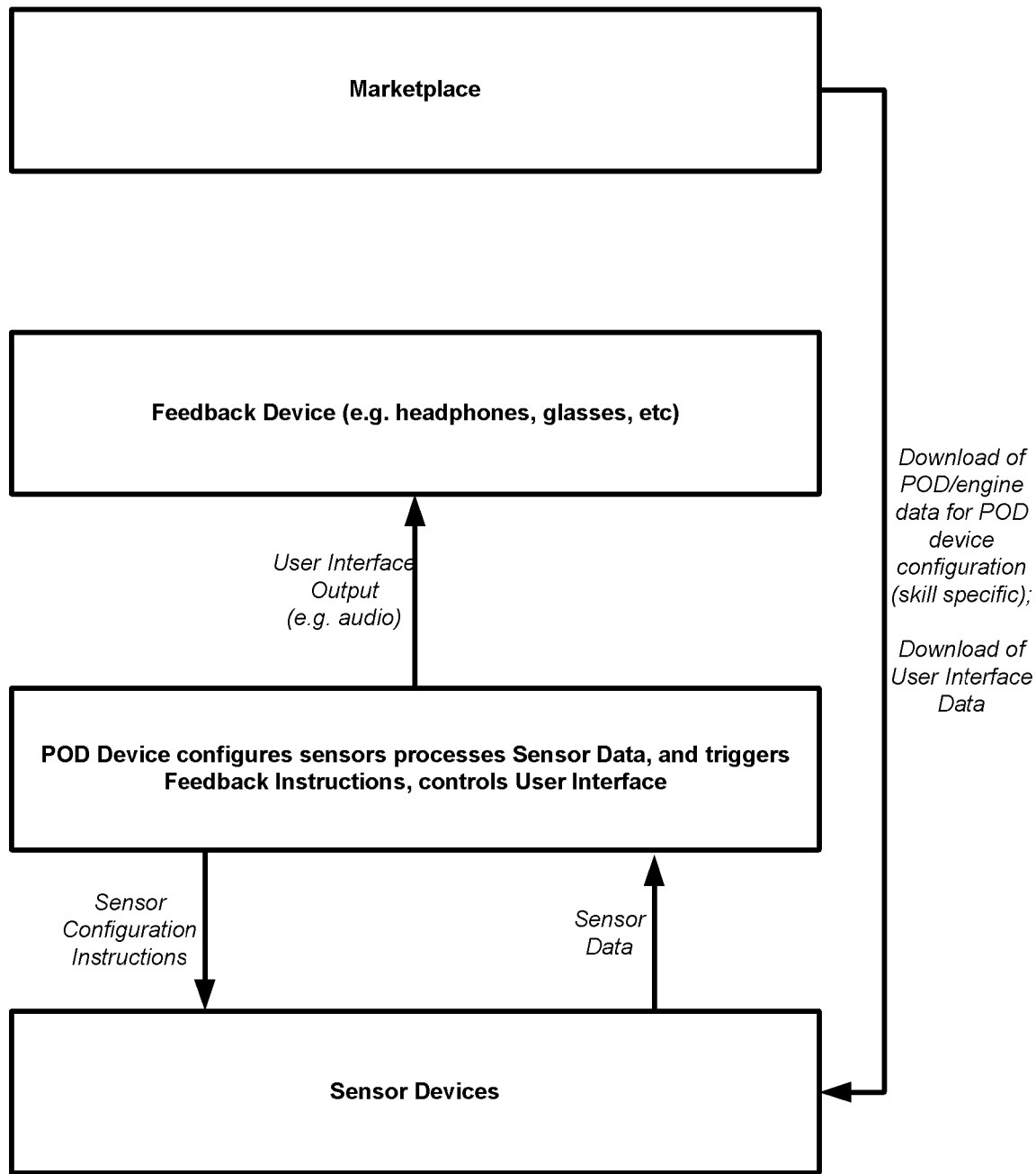
FIG. 10C illustrates operation of a further example framework.

FIG. 10B illustrates an alternate arrangement whereby the mobile device operates in an offline mode. In this example, user interface data is downloaded to the POD device, and provided to the mobile device via the POD device. A further alternate arrangement is illustrated in FIG. 10O, where there is no mobile device, and the POD device provides feedback/instructions directly via a feedback device (such as headphones, glasses with a screen, a retina projection device, or another feedback device).

Example End-User Hardware Arrangements Incorporating MSUs

Described below are various hardware configurations implemented in embodiments there to enable monitoring of an end-user's attempted performance of a given skill, which includes identification of predefined observable data conditions (for example observable data conditions defined by way of methodologies described above) in sensor data collected during that attempted performance.

It should be appreciated that: (i) these are examples only, and technology disclosed herein may be implemented via alternate hardware arrangements; (ii) provided diagrams are schematic and not to scale; and (iii) the diagrams provide functional representations showing key components, and do not represent aspects of PCB design, sensor unit positioning, connective wiring, and the like.

Various embodiments provide a wearable garment. For example, these may include any one or more of: bodysuits, shirts (short or long sleeve), pants (short or long), gloves, footwear, hats, and so on. In some cases a wearable garment is defined by multiple separable garment items (for example a shirt and pants) which are configured to communicate with one another (for example via wired couplings or wireless communication). The garments are preferably manufactured from resilient materials, for example as compression garments. This assists in maintaining sensor components stationary relative to a wearer's body. The garments are preferably manufactured to enable removal of electrical components (such as sensor units and a POD device), for example to enable maintenance or the like.

The garments include a plurality of sensor strands, each sensor strand including one or more sensor units. The sensor strands each commence from sensor strand connection port 1208, wherein the sensor strand connection port is configured to couple a plurality of sensor strands to a central processing device, which is referred to as a POD device in a manner consistent to disclosure further above. The sensor strands may include a single sensor unit, or multiple sensor units.

Where a sensor strand includes multiple sensor units, they are preferably connected in-line. That is, where a strand includes n sensor units $SU_1 \ldots SU_n$, a communication addressed to a sensor unit $Su_i$ is received by and re-transmitted by each of $SU_1 \ldots SU_{i-1}$. Various addressing protocols may be used, however these are configured such that communications are addressed based on sensor unit mounting locations. This allows sensor units to be installed without a need to ensure a given specific sensor unit is installed at a specific mounting location (which is particularly useful if sensor units are removed for garment washing), and also allows swapping out of sensor units (for example in the case of a fault).

In some cases addressing protocols are in part based on identifiers associated with individual sensor units, in which case the POD device performs an auto-configuration step upon recognising a sensor unit thereby to identify the mounting location at which that sensor unit is installed and associate the sensor's identifier with that mounting location. In some embodiments, addressing is achieved by techniques that do not require knowledge of sensor identifiers, such as including a retransmission count in messages (for example a message includes a retransmission integer set by the POD device, which is decremented upon each transmission, and the message received and processed by a sensor unit in the case that the decrementing count reaches zero). The latter approach has some advantages in allowing sensor units to be exchanged/replaced without a need for subsequent reconfiguration of addressing parameters at the POD device.

In a preferred embodiment, each sensor unit includes a circuit board component mounted within a sealed container. The sealed container includes two connection ports; one for upstream communication along the sensor strand, one for downstream communication along the sensor strand. In some embodiments the sensor unit is able to identify an installed orientation, such that which of the ports is the upstream and downstream port determined based on installation orientation. In other embodiments there is a pre-defined installation orientation such that the sensor unit is not able to be installed in reverse. The connection ports are preferably configured for a snap-locking mounting to complementary connection ports on the sensor strands, such that a physically observable coupling correspondingly provides electronic/communicative coupling.

The sensor strands include connecting lines, including one or more lines for communication, and one or more lines for power supply (with power for sensor units being provided by the POD device). The connecting lines are sealed, such that submersion of the garment in water (for example during cleaning) does not cause damage to the lines. Preferably, connector modules that provide connection of the POD device and sensor units to the connecting lines provide watertight seals. Furthermore, in preferred embodiments, when the POD device and sensor units are installed on the garment, all electrical components are provided in a waterproof or water resistant configuration (for example snap-locking engagement of POD device and sensor unit connection ports to sensor strand connection ports provides watertight or water resistant sealing).

On a given sensor strand including a proximal sensor unit and one or more downstream sensor units, the proximal sensor unit is configured to (i) relay, in a downstream direction, sensor instructions provided by the central processing unit and addressed to one or more of the downstream sensor units; and (ii) relay, in an upstream direction, sensor data provided by a given one of the downstream sensor units to the central processing unit. This may include an activation/deactivation instruction. The sensor instruction also include sensor configuration data, wherein the sensor configuration data configures the sensor unit to provide sensor data in a defined manner. The sensor configuration data is in some cases defined by reference to sampling rates, monitoring a reduced selection of information observable by the sensor components, and other configuration attributes defined specifically for a skill that is being observed by the POD device.

Each sensor unit includes (i) a microprocessor; (ii) a memory module; and (iii) a set of one or more motion sensor components. More detailed disclosure of exemplary sensor hardware is provided further below. However, these basic components enable a sensor component to receive communications from a POD device, and provide observed data from the sensor components in a predefined manner (for example defined by reference to resolution, sample rates, and so on). In some embodiments each sensor unit includes a local power supply, however it is preferably that power is supplied along the sensor strands from the POD device (or another central power supply) rather than requiring individualised charging of sensor unit batteries or the like.

For an exemplary sensor unit, the set of one or more sensor components includes one or more of: (i) a gyroscope; (ii) a magnetometer; and (iii) an accelerometer. In preferred embodiments described below there is one of each of these components, and each is configured to provide three-axis sensitivity. In further embodiments there are multiple components of one or more of the components types, for example two accelerometers. This enables differing configurations, for example such that one is configured to observe course movements at a given resolution, and the other to observe specific fine movements at higher resolution.

The central processing device (POD device) includes (i) a power supply; (ii) a microprocessor; and (iii) a memory module. The memory module is configured to store software instructions executable by the microprocessor that enable the processing device to perform various functionalities, including configuration of sensor units to transmit sensor data in a predefined manner and to identify one or more sets of predefined observable data conditions in sensor data, including sensor data received by the central processing device from the plurality of connected sensor units. In a preferred embodiment the POD device also includes sensor components (for example the same sensor components as a sensor unit) thereby to enable motion observation at the position of the POD device. In some embodiments the POD device is mounted to the garment in a pouch provided in a location that, in use, is proximal the upper centre of a user's back (for example between shoulder blades).

Figure 12A:
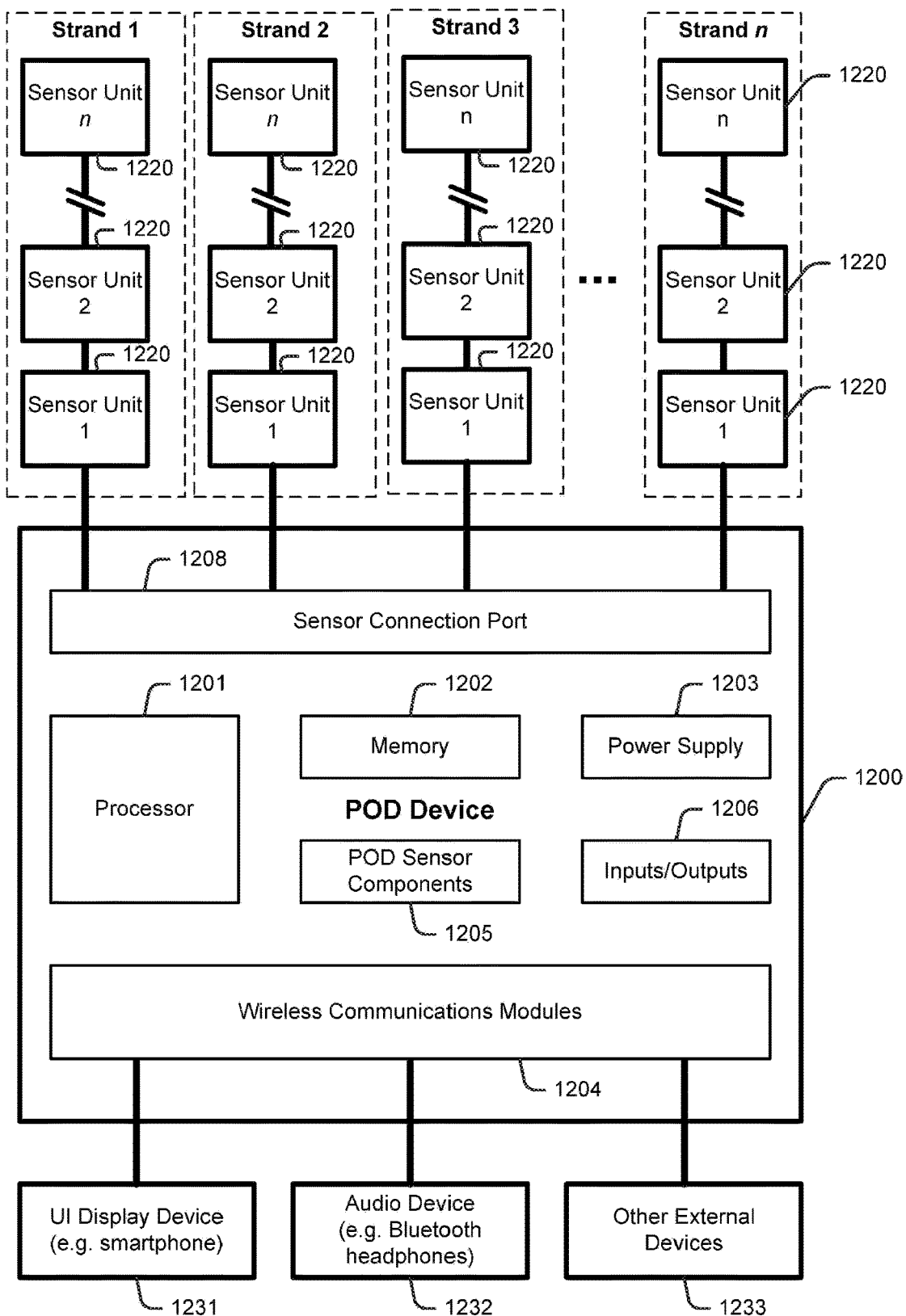
FIG. 12A illustrates performance analysis equipment according to one embodiment.

FIG. 12A illustrates a selection of hardware components of a wearable garment according to one embodiment. It will be appreciated that these are illustrated without reference to geometric/spatial configurations resulting from configuration of the garment itself.

The POD device 1200 of FIG. 12A includes a processor 1201 coupled to a memory module 1202, the memory module being configured to store software instructions thereby to provide functionalities described herein. These include:

Data representative of a training program (or multiple training programs), including logic for progressing through the training program, and user interface data that communicated externally of the POD device rendered by other components (such as a headset, display device, and so on).

For the (or each) training program, a plurality of skills that are to be trained. Each skill is defined by data including sensor configuration instructions, rules for identifying observable data conditions in sensor data, and rules relating to feedback (and/or other actions) that are when particular observable data conditions are identified. For example, these are defined by a process such as phases 501-503 of FIG. 5A.

It will be appreciated that various other aspects of software instructions are also provided.

A rechargeable power supply 1203 provides power to POD device 1200, and to one or more connected devices (including sensor units and, where provided, one or more control units). Local sensor components 1205 (for example three-axis magnetometer, three-axis accelerometer, and three-axis gyroscope) enable the POD device to function as a sensor unit. Inputs/outputs 1206 are also provided, and these may include the likes of: power/reset buttons; lights configured to display operational characteristics; and in some embodiments a display screen. However, in embodiments herein described the primary modes of communications between the POD device and a user are by external (and self-powered) user interface devices.

POD device 1200 includes one or more wireless communications modules 1204, thereby to enable communications/interactions with one or more remote devices. For example, the communications modules may include any one or more of the following:

WiFi. For example, WiFi is in some embodiments used to deliver user interface content (including image, text, audio and video data) for rendering at a UI display device 1231. This may include a smartphone, tablet, device with heads-up-display (such as an augmented reality headset or eyewear), and other such devices. The UI display device may be used to select and/or navigate training content available to be delivered via the POD device.

Bluetooth. For example, Bluetooth is in some embodiments used to deliver renderable audio data to a Bluetooth headset or the like, thereby to provide audible instructions/feedback to a user.

ANT+ (or other such communications modules) configured to enable interaction with monitoring devices, such as heart rate monitors and the like.

RF communications modules. In some embodiments one or more such modules are provided thereby to enable communication with wireless sensor units, for example sensor units that are configured to be attached to equipment (such as a skateboard, gold club, and so on). In some cases this includes a wireless sensor strand, defined by a plurality of wired sensor units connected to a common hub that wirelessly communicates with the POD device.

There may be various other wireless communication modules for various other external devices 1233.

The POD device includes a circuit board, and optionally additional hardware components, provided in a sealed or sealable container (water proof or water resistant). This container is able to be mounted to the garment (or example in a specifically configured pouch), and that mounting includes connection of one or more couplings. Preferably, a single coupling connects the POD device to all available sensor strands. Again, this may be a snap-lock coupling (water proof or water resistant), which provides both physical and electronic coupling substantially simultaneously.

FIG. 12A illustrates multiple sensor strands (Strand 1 . . . Strand n) coupled to a sensor connection port 1208. Each sensor strand includes a plurality of sensor units (Sensor Unit 1 . . . Sensor Unit n), however it should be appreciated that in some embodiments a given strand includes only a single sensor unit.

Figure 12B:
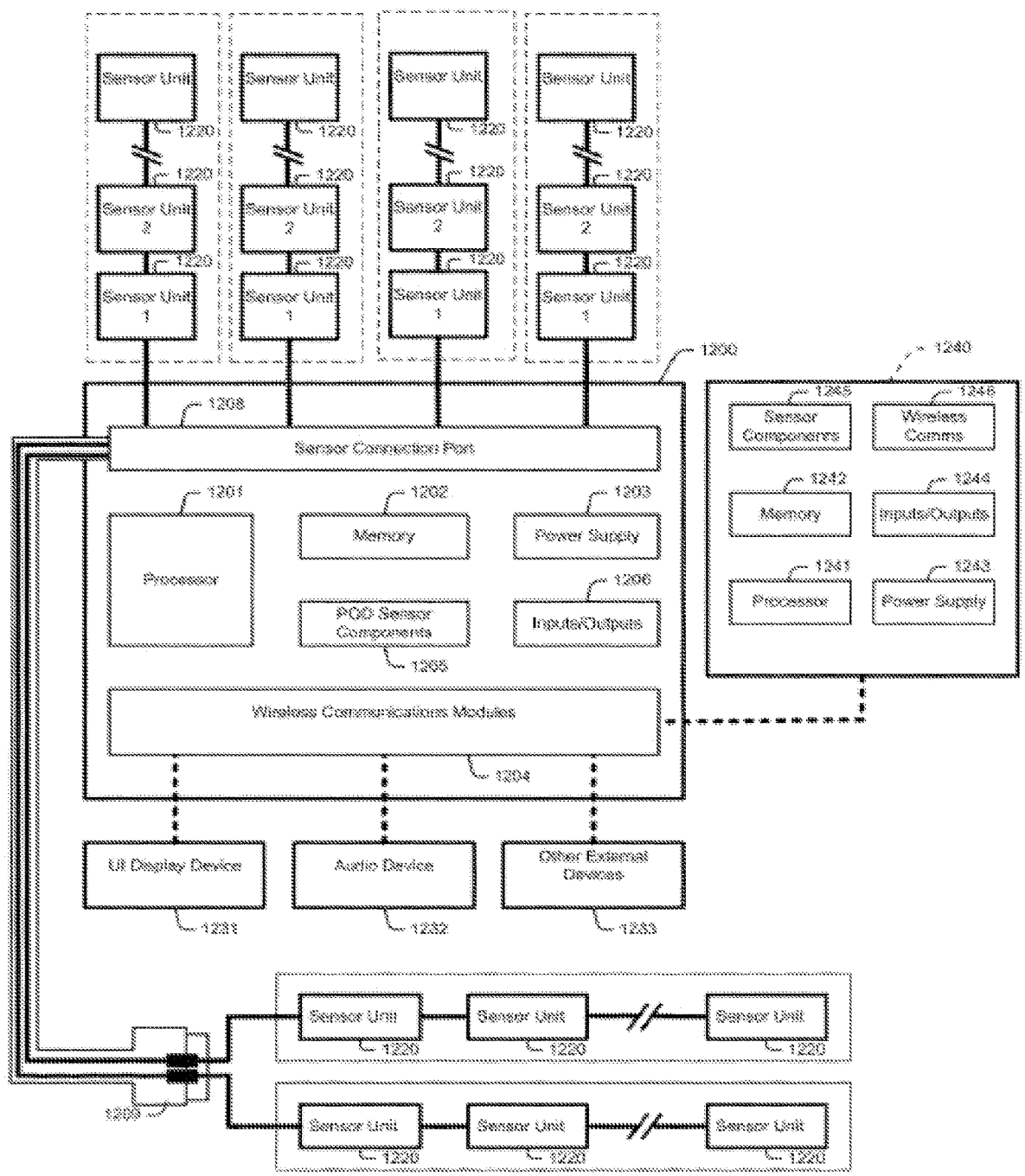
FIG. 12B illustrates performance analysis equipment according to one embodiment.

FIG. 12B illustrates an alternate arrangement of sensor strands. As context, some embodiments provide garments configured with one or more "partial" sensor strands. Each partial sensor strand includes (i) none or more sensors units; and (ii) a connector module that is configured to couple to a complementary connector module provided by a secondary garment. The phrase "none or more" indicates that in some cases a partial sensor strand is defined by a sensor strand line connecting the POD device to a connector module without any intervening sensor units, and on other cases partial sensor strand is defined by a sensor strand line on which one or more sensor units are provided, the strand terminating at a connector module.

Coupling of the connector module to the complementary connector module provided by a secondary garment functionally connects one or more of the partial sensor strands to a corresponding one or more secondary garment partial sensor strands, thereby to enable communication between (i) one or more sensor units provided on the one or more secondary garment partial sensor strands; and (ii) the central processing device.

In the example of FIG. 12B, a garment includes a shirt and pants. There are four shirt sensor strands, and two pants sensor strands. A connector arrangement 1209 couples partial pants strands thereby to enable communication between the sensor units provided on the pants, and the pod device (and powering of those sensor units by the POD device). In further embodiments this sort of arrangement is used to enable connection to sensor units provided on footwear, handwear, headwear, and so on. For example, in some embodiments connector ports are provided proximal arm, neck and foot apertures thereby to enable elongation of a provided sensor strand by one or more further sensor units carried by a further garment item or device.

In some embodiments, sensors carried by secondary garments, such as handwear or footwear, include specialist sensor components that measure attributes other than motion. For example, pressure sensor components may be used (for example thereby to measure grip strength on a gold club, to measure force being applied to the ground or another object, and so on). The POD device is configured to know, for a given training program, the sensor arrangement that is to be provided. For example, a user is provided instructions in terms of the sensor units that should be connected, and the POD device performs a check to ensure that sensors are responding, and expected sensor data is being provided.

FIG. 12B also illustrates an equipment mountable sensor unit 1240. This unit includes a processor 1241, memory 1242 and sensor components 1245 substantially in the same manner as does a sensor unit 1220. However, it additionally includes a wireless communications module 1246, thereby to enable wireless communications (for example RF communication) with POD device 1200, and a local power supply 1243. Inputs/outputs (such as lights, power/reset buttons, and the like) are also provided.

Figure 12C:
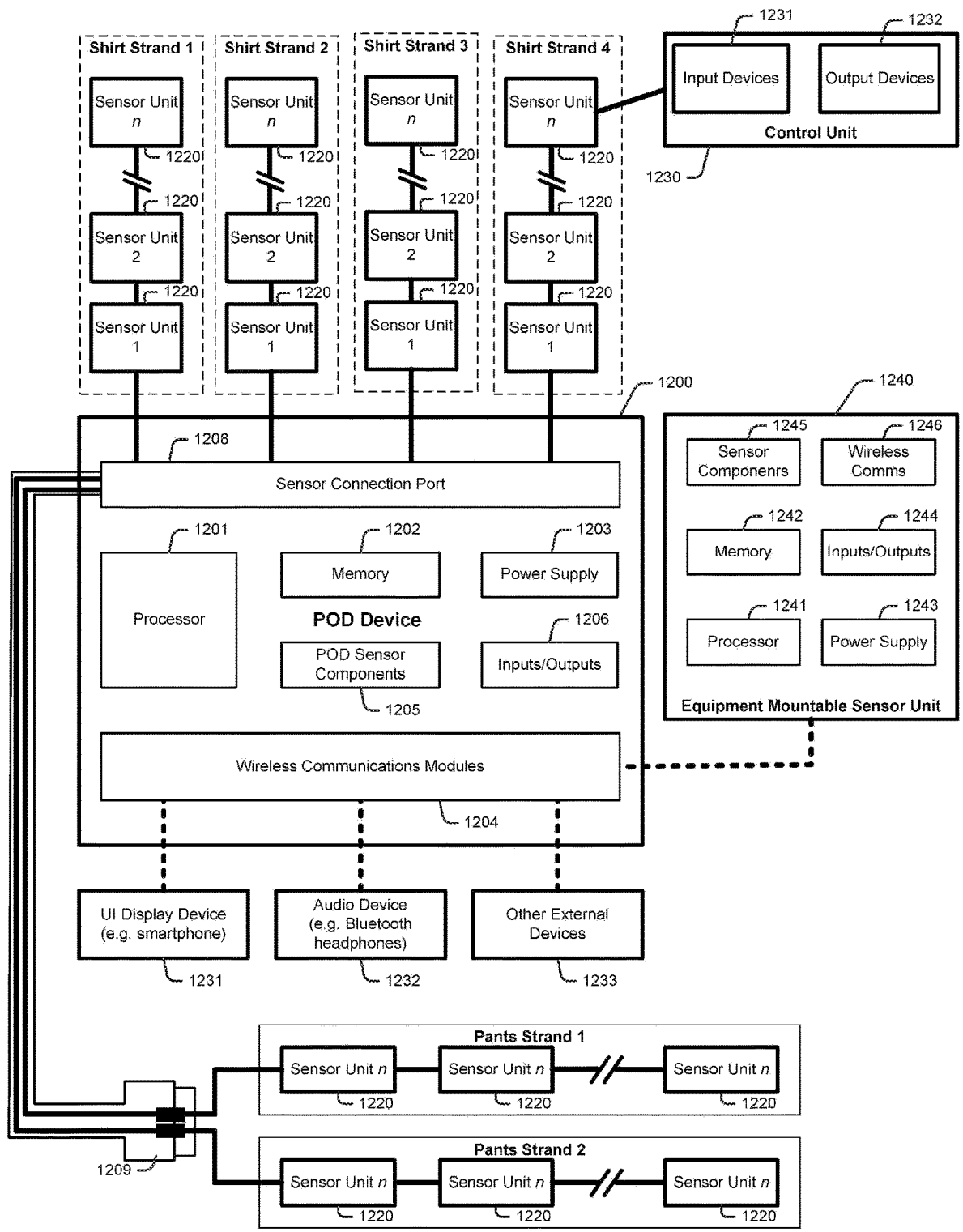
FIG. 12C illustrates performance analysis equipment according to one embodiment.

FIG. 12C expands on FIG. 12B by providing a control unit 1230. This control unit is physically coupled to the distal end of one of the shirt strands, for example as a wrist-mounted control unit. In some embodiments the control unit is integrated with a sensor unit. Control unit 1230 includes input devices 1231, such as one or more buttons, and output devices 1232, such as one or more lights and/or a display screen (preferably a low-power screen). Control unit 1230 is provided to assist a user in providing basic commands to control the provision of training content via the POD device. For example, commands may include "previous" and "next", for example to repeat a previous audible instruction, or skip forward to a next stage in a training curriculum. In some embodiments audible content is provided to assist a user in operating the input devices, for example by audibly providing selectable menu items.

Figure 12D:
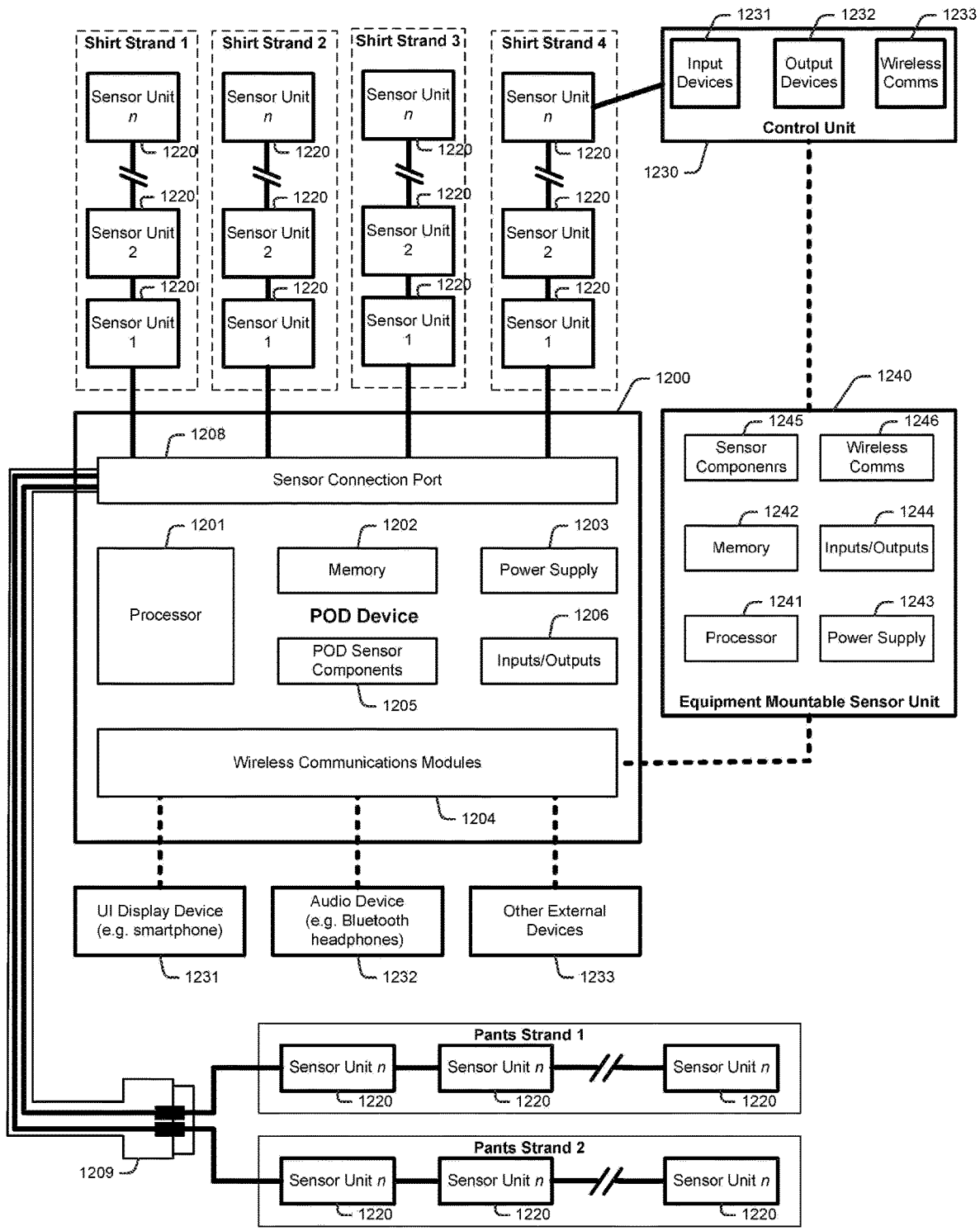
FIG. 12D illustrates performance analysis equipment according to one embodiment.

In the embodiment of FIG. 12D, control unit 1230 additionally includes a wireless communications module (for example RF) configured to receive wireless signals provided by equipment mountable sensor unit 1240. In this manner, wireless sensor unit data is able to be received both at the POD device directly (via modules 1204) and indirectly (via module 1233, via control unit 1230 and along a sensor strand, in this case being shirt sensor strand 4). This provides redundancy for the wireless communications; it should be appreciated that there can be challenges in reliably receiving wireless communications where signals pass through a human body (which is predominately water). Having two spaced apart locations (either as shown in FIG. 12D, or via an alternate arrangement), there is a significantly increased chance that all sensor data from unit 1240 will be received and made available for analysis. The POD device implements a data integrity protocol thereby to determine how to combine/select data provided by each of the two pathways. In some embodiments, for example where there is greater reliance of external sensor units, there may be multiple redundant wireless communications units positioned at various locations on the garment.

In some embodiments unit 1230 is provided on its own strand, rather than on a sensor strand which might otherwise include a terminal connector for attachment of a sensor-enabled handwear component.

Figure 12E:
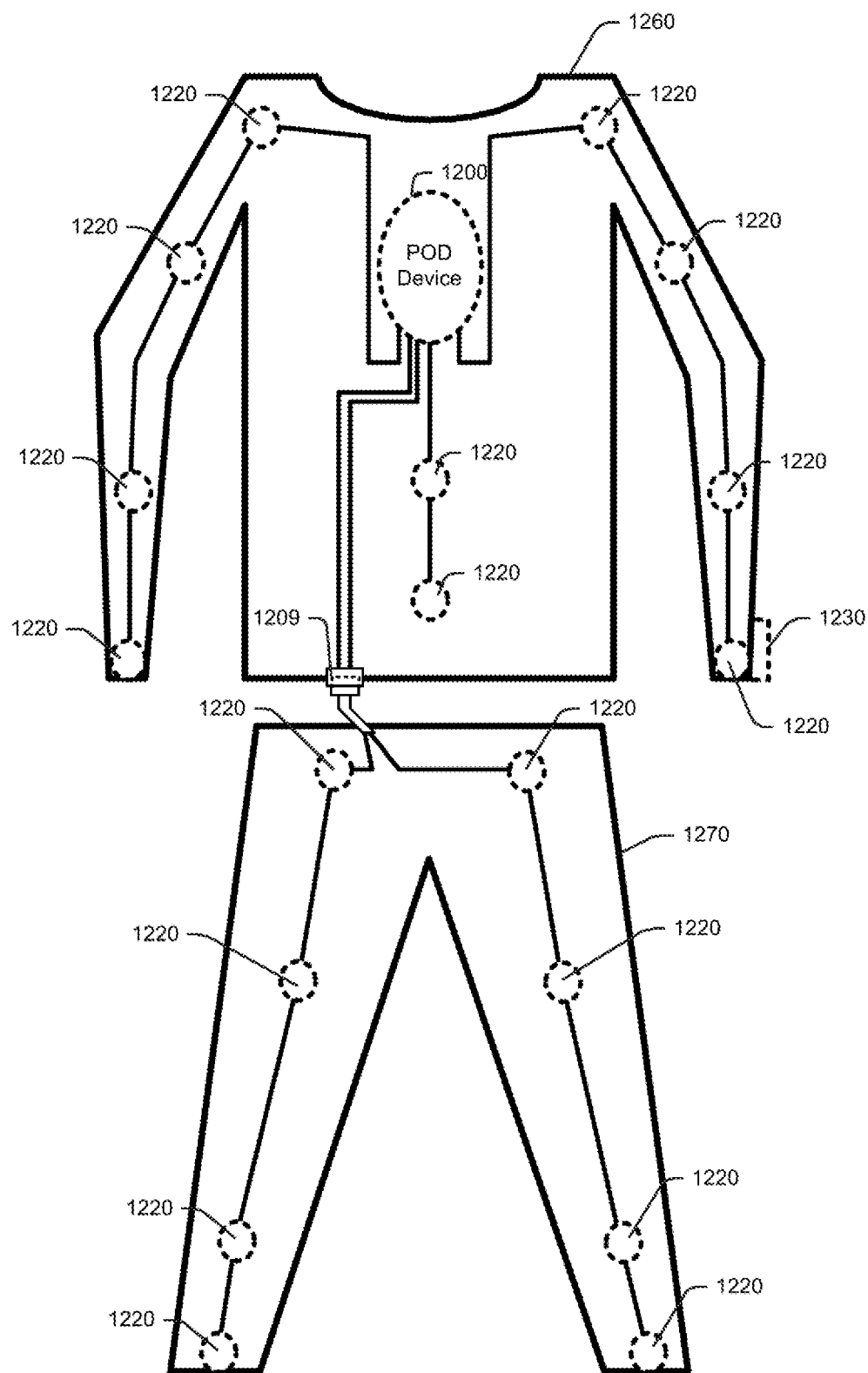
FIG. 12E illustrates a MSU-enabled garment arrangement according to one embodiment.

FIG. 12E provides a schematic representation (not to scale) of a two-piece garment according to one embodiment. This is labelled with reference numerals corresponding to previous figures. The illustrated garment is a two-piece garment, being defined by three sensor strands on the shirt component, and two sensor strands which provide sensor units on the pants component (with a connector 1209 coupling sensor strands between the garment components).

The illustrated positioning of sensor units is by no means intended to be limiting, and instead provides a rough guide as to potential sensor unit locations for a garment having this number of sensor units. A general principle illustrated in FIG. 12E is to provide sensors away from joints. Data collected from the respective sensor units' gyroscopes, accelerometers and magnetometers enables processing thereby to determine relative sensor locations, angles, movements and so on across multiple axis (noting that providing three 3-axis sensors in effect provides nine degrees of sensitivity for each sensor unit). Rich data relating to body movement is hence able to be determined. Furthermore, by way of configuration data provided by the POD device, the sensitivity/operation of each sensor is able to be selectively tuned for particular skills, for example to set levels for each individual sensor component, report only on particular motion artefacts, and so on. This is of utility from a range of perspectives, including reducing power consumption at the sensor units, reducing processing overheads at the POD device, and increasing sensitivity to particular crucial motion artefacts (for example by applying a kinematic model which monitors only motions having particular defined characteristics, for example high resolution monitoring of motion in a rowing action, as opposed to motion of a person walking towards a rowing machine).

Figure 12F:
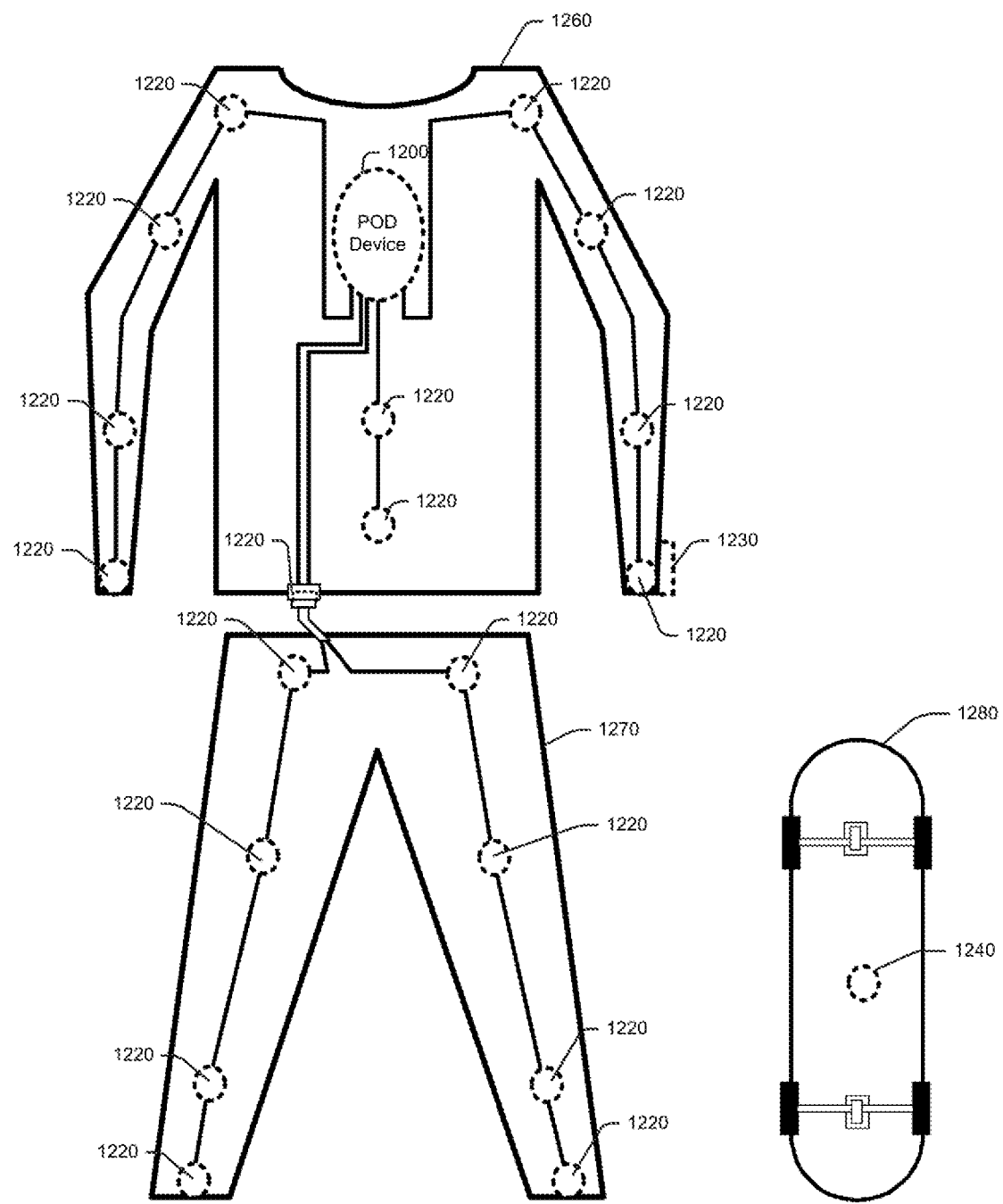
FIG. 12F illustrates a MSU-enabled garment arrangement according to one embodiment, with example connected equipment.

FIG. 12F expands on FIG. 12E by way of illustrating a piece of remote equipment, in this case being a skateboard, which carries a wireless sensor unit 1240. As described above, it is preferable that sensor unit 1240 communicate wirelessly with POD device 1200 via multiple communication pathways, thereby to manage limitations associated with wireless communications. For example, in the illustrated example signals transmitted by sensor unit 1240 are configured to be received by a wireless communications module provided by POD device 1200, and by a wireless communications module provided by wrist control unit 1230 (which transmits the received sensor data via the sensor strand to which it is connected).

Figure 12G:
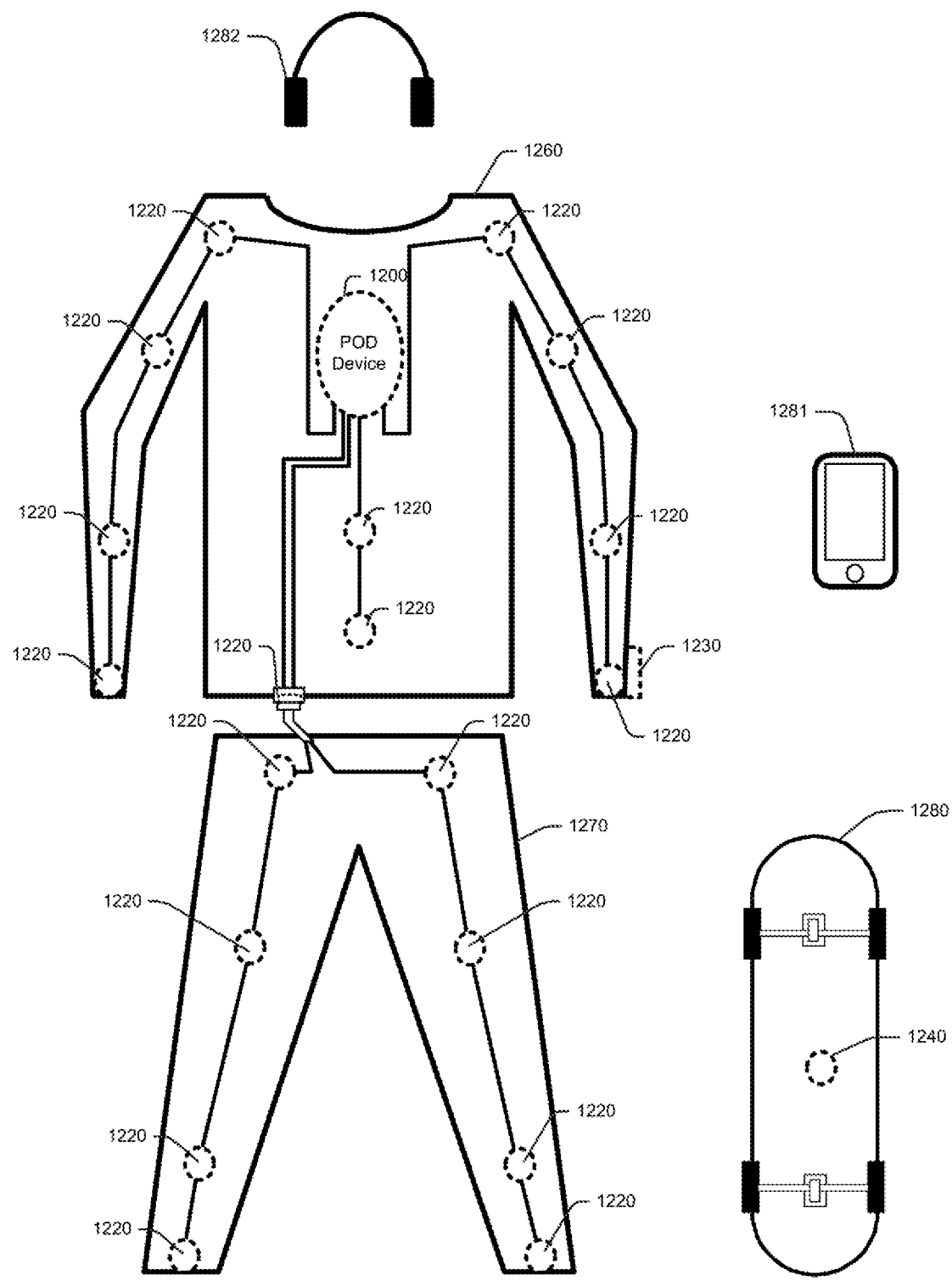
FIG. 12G illustrates a MSU-enabled garment arrangement according to one embodiment, with example connected equipment.

FIG. 12G expands on FIG. 12F by illustrating a mobile device 1281, and a wireless headset 1282.

POD device 1200 communicates with mobile device 1281 (for example a smartphone or tablet, which may operate any of a range of operating systems including iOS, Android, Windows, and so on) thereby to provide to mobile device data configured to enable rendering of content in a user interface display, that content assisting in guiding a user through a skills training program. For example, the content may include video data, text data, images, and so on. In some embodiments POD device 1200 operates as a local web server for the delivery of such content (that is, the mobile device connects to a wireless network advertised by the POD device).

Headset 1282 (which need not be a headset of the design configuration illustrated) enables the user to receive audible feedback and/or instructions from the POD device without a need to carry or refer to a mobile device 1281. This is relevant, for example, in the context of skills where it would be unfeasible or otherwise generally inconvenient to refer to a mobile device, for example whilst rowing, jogging, swimming, snowboarding, and so on. In some embodiments a wired headset may be used, for example via a 3.5 mm headphone jack provided by the garment, which is wire-connected to the POD device.

Figure 12H:
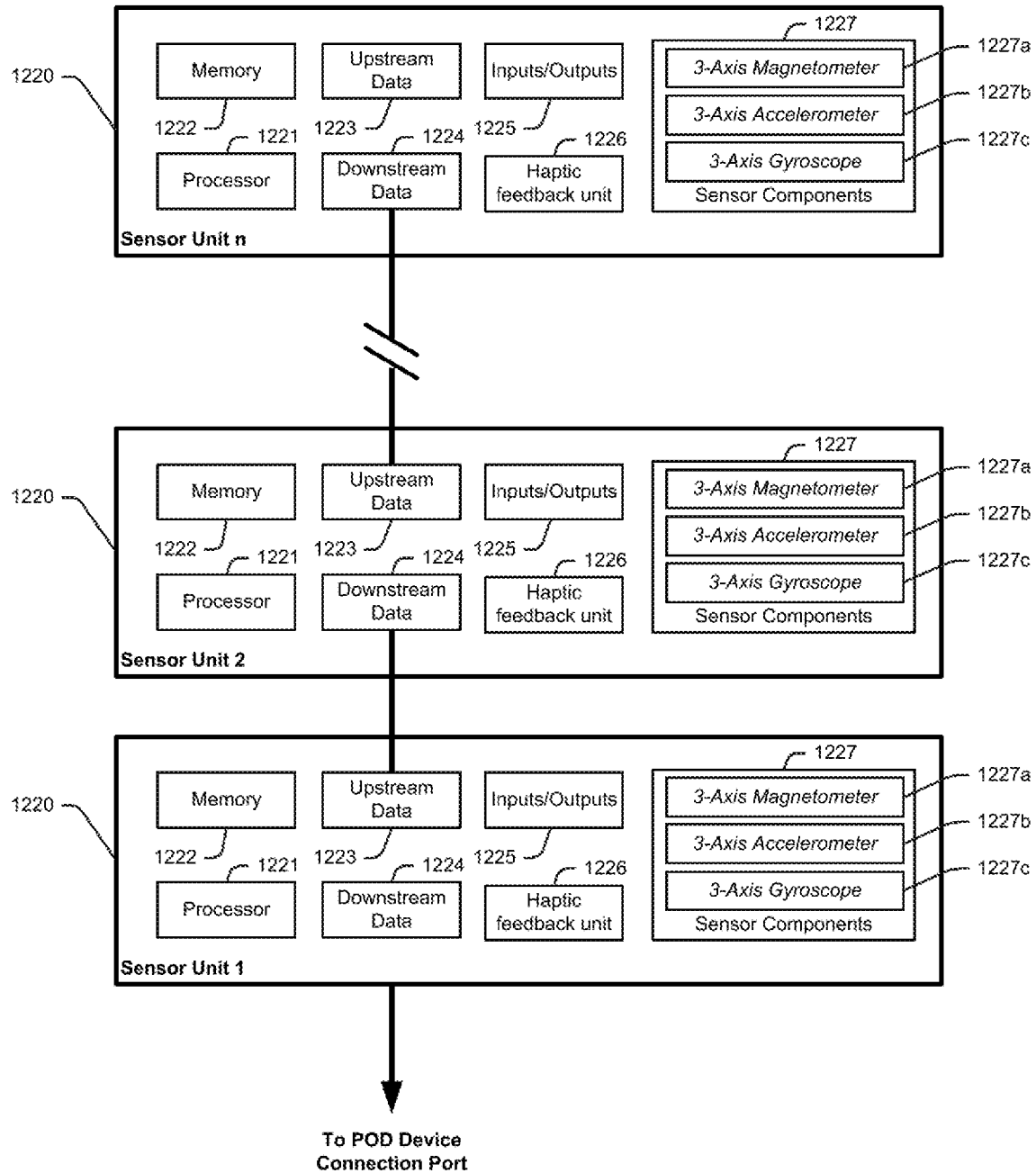
FIG. 12H illustrates MSUs according to one embodiment.

FIG. 12H illustrates a sensor strand according to one embodiment. This includes a plurality of sensor units 1220. Each sensor unit includes a processor 1221 coupled to memory 1222. Upstream and downstream data connections 1223 and 1224 are provided (these may in some embodiments be functionally distinguished based on install orientation). Inputs/outputs 1225 may be provided, such as lights and/or a power/reset button. The illustrated embodiment includes a haptic feedback unit 1226, which may be used to assist in providing feedback to a user (for example activating haptic feedback on a right arm sensor unit corresponding with an instruction to do something with the user's right arm). The illustrated sensor components 1227 are a 3-axis magnetometer 1227a, a 3-axis accelerometer 1227b, and a 3-axis gyroscope 1227c.

Figure 12I:
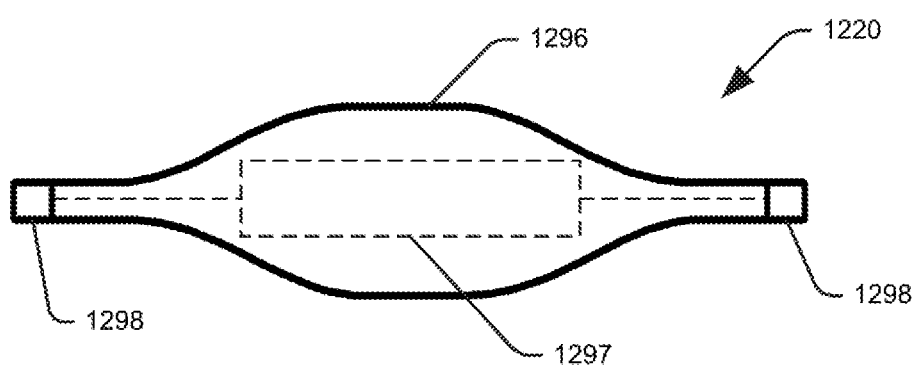
FIG. 12I illustrates a MSU and housing according to one embodiment.
Figure 13A:
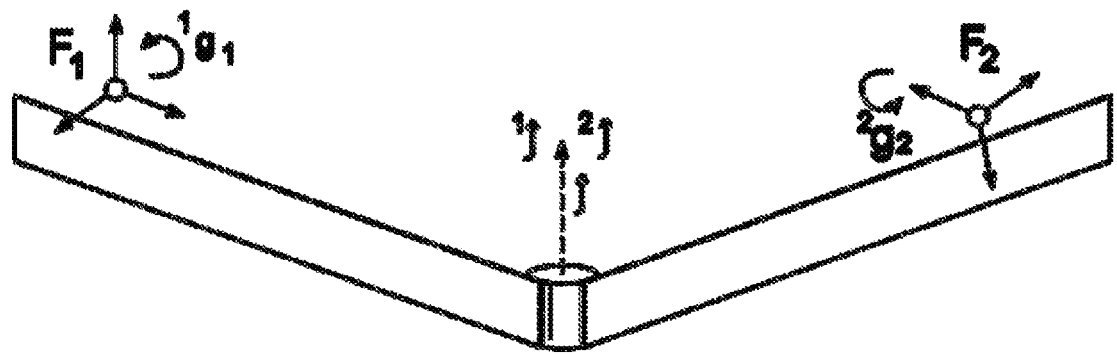
FIG. 13A schematically illustrates aspects of a hinge joint.
Figure 13B:
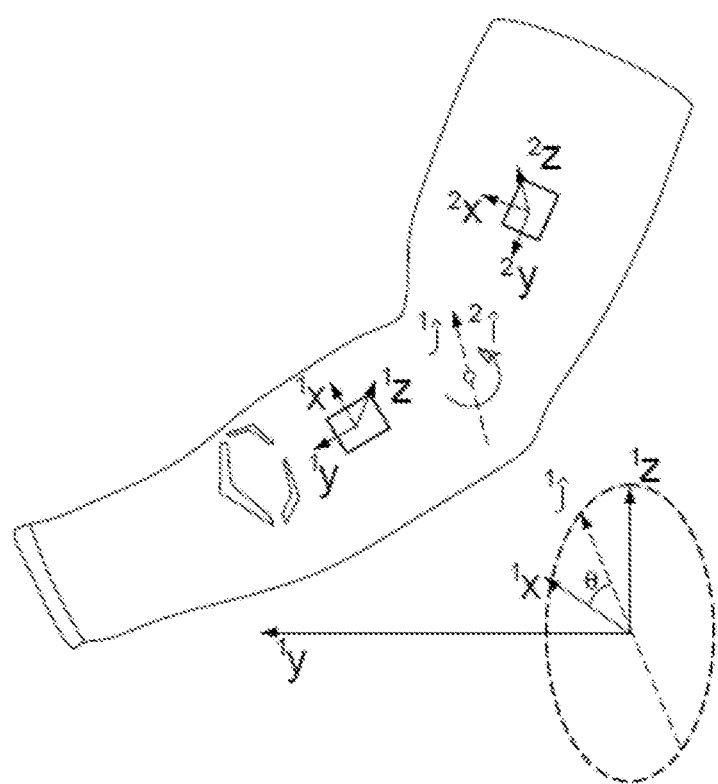
FIG. 13B schematically illustrates aspects of an elbow joint.
Figure 13C:
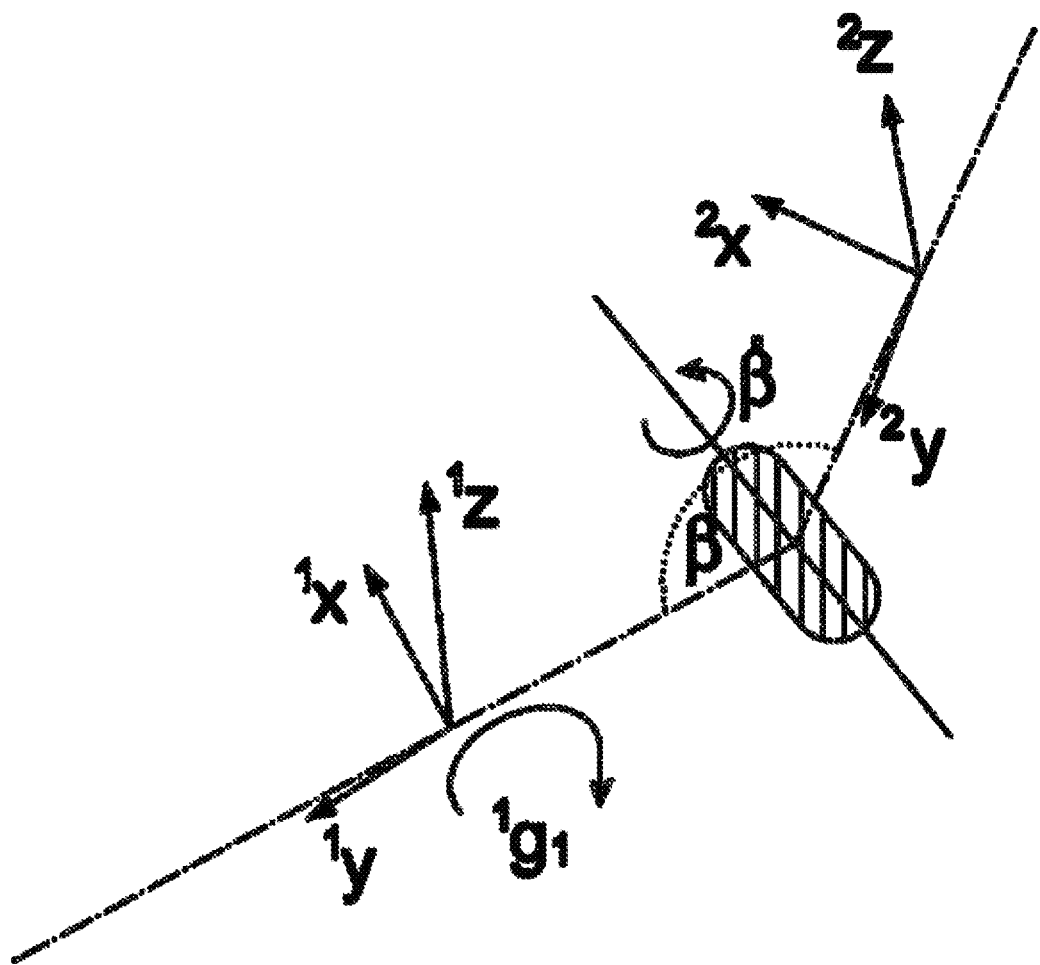
FIG. 13C schematically illustrates aspects of a joint.
Figure 13D:
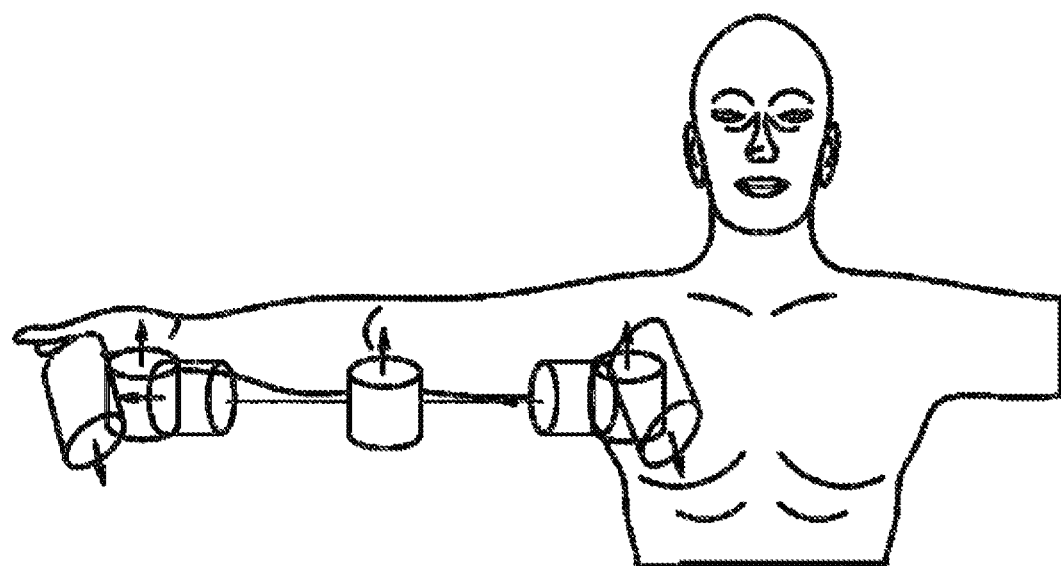
FIG. 13D schematically shows joint movement for a human arm.

FIG. 12I illustrates an exemplary sensor unit 1220, showing a housing 1296 according to one embodiment. This housing is formed of plastic material, and encloses, in a watertight manner, a circuit board 1297 which provides components illustrated in FIG. 12H. Connectors 1298 enable connection to a sensor strand provided by a garment.

FIG. 17 provides an alternate view of a MSU-enabled garment, showing a stretch/compression fabric that provides a sensor strand and MSU mounting locations.

Configuration of MSUs and MSU-Enabled Garments: Overview

Identification of ODCs in end-user equipment in some cases requires: (i) knowledge of the actual positions of MSUs on a given user; and (ii) knowledge of the relative positioning of the MSUs. There are challenges in meaningfully combining data from multiple MSUs, as each MSU conventionally provide motion data with respect to their own frames of reference.

Various embodiments described above make use of data derived from a set of sensor units thereby to enable analysis of a physical performance. These sensor units are mounted to a user's body, for example by way of wearable garments that are configured to carry the multiple sensor units. This section, and those which follow, describe exemplary methodologies that are in some embodiments for configuration of sensor units thereby to enable analysis of movements, such as human body movements, based on data derived from the sensors.

By way of background, a known and popular approach for collecting data representative of a physical performance is to use optical motion capture techniques. For example, such techniques position optically markers observable at various locations on a user's body, and using video capture techniques to derive data representative of location and movement of the markers. The analysis typically uses a virtually constructed body model (for example a complete skeleton, a facial representation, or the like), and translates location and movement of the markers to the virtually constructed body model. In some prior art examples, a computer system is able to recreate, substantially in real time, the precise movements of a physical human user via a virtual body model defined in a computer system. For example, such technology is provided by motion capture technology organisation Vicon.

Motion capture techniques are limited in their utility given that they generally require both: (i) a user to have markers positioned at various locations on their body; and (ii) capture of user performance using one or more camera devices. Although some technologies (for example those making use of depth sensing cameras) are able to reduce reliance on the need for visual markers, motion capture techniques are nevertheless inherently limited by a need for a performance to occur in a location where it is able to be captured by one or more camera devices.

Embodiments described herein make use of motion sensor units thereby to overcome limitations associated with motion capture techniques. Motion sensor units (also referred to as Inertial Measurement Units, or IMUs), for example motion sensor units including one or more accelerometers, one or more gyroscopes, and one or more magnetometers, are able to inherently provide data representative of their own movements. Such sensor units measure and report parameters including velocity, orientation, and gravitational forces.

The use of motion sensor units presents a range of challenges by comparison with motion capture technologies. For instance, technical challenge arise when using multiple motion sensors for at least the following reasons:

Each sensor unit provides data based on its own local frame of reference. In this regard, each sensor inherently provides data as though it defines in essence the centre of its own universe. This differs from motion capture, where a capture device is inherently able to analysis each marker relative to a common frame of reference.

Each sensor unit cannot know precisely where on a limb it is located. Although a sensor garment may define approximate locations, individual users will have different body attributes, which will affect precise positioning. This differs from motion capture techniques where markers are typically positioned with high accuracy.

All sensors act completely independently, as if they were placed in an electronic "bowl of soup", with no bones/limbs connecting them. That is, the sensors' respective data outputs are independent of relative positioning on any sort of virtual body, unlike markers used in motion capture.

Technology and methodologies described below enable processing of sensor unit data thereby to provide a common body-wide frame of reference. For example, this may be achieved by either or both of: (i) defining transformations configured to transform motion data for sensor units $SU_1$ to $SU_n$ to a common frame of reference; and (ii) determining a skeletal relationship between sensor units $SU_1$ to $SU_n$. It will be appreciated that in many cases these are inextricably linked: the transformations to a common frame of reference are what enable determination of skeletal relationships.

In some embodiments, processing of sensor data leads to defining data representative of a virtual skeletal body model. This, in effect, enables data collected from a motion sensor suit arrangement to provide for similar forms of analysis as are available via conventional motion capture (which also provides data representative of a virtual skeletal body model).

The processing techniques described below find application in at least the following contexts:

Assembling a skeletal model that is suitable for comparison with a model provided via defined motion capture technology. For example, both motion capture data and sensor-derived data may be collected during an analysis phase, thereby to validate whether a skeletal model data, derived from processing of motion sensor data, matches a corresponding skeletal model derived from motion capture technology. This is applicable in the context of a process for objectively defining skills (as described above), or more generally in the context of testing and validating data sensor data processing methods.

Automated "non-pose specific" configuration of a worn sensor-enabled garment. That is, rather than requiring a user to adopt one or more predefined configuration poses for the purpose of sensor configuration, processing techniques described below allow transformation of each respective sensors' data to a common frame of reference (for example by assembling a skeletal model) by processing sensor data resulting from substantially any motion. That is, the approaches below require fairly generic "motion", for the purpose of comparing motion of one sensor relative to another. The precise nature of that motion is of limited significance.

Enabling accurate monitoring of a physical performance of a skill (for example in the context of skill training and feedback). For example, this may include monitoring for observable data conditions in sensor data (which are representative of performance affecting factors, as described above).

A number of approaches are described below. These are able to be applied individually, or in combination (for example overlapped and/or in a hybrid arrangement).

Examples considered below consider two sensor units including Inertial Measurement Units (IMUs) that provide acceleration and angular velocity samples expressed in their own frames of reference. Let these IMUs be $S_1$ and $S_2$ respectively, and $\mathcal{F}_1$ and $\mathcal{F}_2$ their local frames, respectively (that is, an IMU is designated by "S", and a sensor unit, which may include one or more IMUs and optionally other sensor hardware is designated by "SU").

By convention, a vector v expressed in frame $\mathcal{F}_1$ will be denoted using left superscript notation:

$^1v$.

At each moment in time, the two sensor frames, $\mathcal{F}_1$ and $\mathcal{F}_2$, are linked by a transformation matrix. Such a matrix, which transforms a vector $^2v$ into another one expressed in $\mathcal{F}_1$, denoted $^1v$, is written as:

$$^1v = {}^1_2 T \, {}^2v.$$

Configuration of Sensor Units: Joint Constraints

Some exemplary methodologies make use of joint performance knowledge. That is, a first sensor unit $SU_1$ and a second sensor unit $SU_2$ are mounted to link members on opposed sides of a known joint; using knowledge about the joint type, methodologies described below enable processing thereby to transform the respective sensors' data to a common frame of reference. That is, the methods include, based on a defined set of joint constraints, determining a relationship between the motion data for $SU_1$ and $SU_2$. For example, this includes identifying a location and motion of the joint between $SU_1$ and $SU_2$ based on the respective frames of reference defined by $SU_1$ and $SU_2$.

A practical example is a human body: the link members are human body parts of a human body. For instance, sensor units are mounted to an upper arm location and a forearm location, which have the elbow (a hinge joint) in between. Analysis of motion data from those sensors, with joint constraints defined for an elbow joint hinge, enables transformation of the motion data from each to a common frame of reference. This is performed for multiple pairs of sensor units that are mounted to body positions at opposed sides of multiple known body joints (being known joints of known joint types, for example hinge, spherical, or universal) thereby to define transformations configured to transform motion data from each of the sensor units to a common frame of reference for the human body. This optionally leads to maintaining a skeletal motion model for the human body based upon application of the defined transformations to motion data received from the plurality of sensor units.

Turning to the detail, let $g_1$ and $g_2$ be the angular velocities reported by the individual IMU sensors. We consider that these sensors are attached to two links joined together by a hinge constraint (i.e. one angular degree of freedom). Since the sensors provide samples at a predetermined rate (e.g. 50 Hz), it is necessary to add time as a parameter to each angular velocity vector. This helps distinguish between samples. Furthermore, these samples are expressed in different local frames, i.e. the frame of the sensor that measures them. Thus, at a certain time instance t, we know the following amounts: $^1g_1(t)$ and $^2g_2(t)$.

It should be appreciated that: If $\hat{j}$ is the unit axis of the hinge joint in world space, then the following constraint holds true at any instant of time t:

$$\|g(t) \times {}^2\hat{j}\|_2 = \|{}^1g_1(t) \times {}^1\hat{j}\|_2. \tag{1}$$

As proof, it is possible to exploit the hinge constraint and establish a connection between the angular velocity vectors. Normally, if the hinge joint does not rotate at all, the two gyroscopes should report angular velocities that have the same magnitude and can be transformed into each other via a constant rotation matrix. If the hinge joint does rotate, we have the following equivalent of an angular transport velocity:

$${}^1g(t) = {}^1g_1(t) + {}_2{}^1R(t,\theta)(\dot{\theta}{}^2\hat{j}), \tag{2}$$

where $(\dot{\theta}{}^2\hat{j})$ is the angular velocity incurred by the rotation about the $\hat{j}$ hinge axis, ${}_2{}^1R(t, \theta)$ is the rotation part of the transform relating the two sensor frames at time t, when the joint angle is θ. We multiply both sides of equation (2) by ${}_2{}^1R(t, \theta)^{-1}$ and obtain:

$$({}_2{}^1R(t,\theta)^{-1}){}^1g(t) = ({}_2{}^1R(t,\theta)^{-1}){}^1g_1(t) + \dot{\theta}{}^2\hat{j}|\times{}^2\hat{j}$$

which is equivalent to $$g(t) \times {}^2\hat{j} = ({}_2{}^1R(t,\theta)^{-1}){}^1g_1(t) \times {}^2\hat{j},$$

or, better written as:

$$g(t) \times {}^2\hat{j} = {}_1{}^2R(t,\theta){}^1g_1(t) \times {}^2\hat{j}. \tag{3}$$

Since the axis $\hat{j}$ is representable in both frames and we're only interested in its orientation, we can also write:

$${}^2\hat{j} = {}_1{}^2R(t,\theta){}^1\hat{j}. \tag{4}$$

Combining equations (3) and (4) with the rotation matrix versus cross product property $Ru \times Rv = R(u \times v)$, we get:

$$g(t) \times {}^2\hat{j} = {}_1{}^2R(t,\theta)({}^1g_1 \times {}^1\hat{j}), \tag{5}$$

which is equivalent to the following norm constraint:

$$\|g(t) \times {}^2\hat{j}\|_2 = \|{}^1g_1(t) \times {}^1\hat{j}\|_2. \tag{6}$$

It should be appreciated that, in relation to hinge joint angular velocity, at any time instant, the angular velocity about the $\hat{j}$ hinge joint is given through the following equation:

$$\dot{\theta} = g \cdot {}^2\hat{j} - {}^1g_1 \cdot {}^1\hat{j}. \tag{7}$$

As a proof, the following remarks are made. On the one hand, the angular velocity of the second gyroscope can be expressed in the frame of the first sensor as described by equation 2, but also by directly using the rotation part of the transform matrix, i.e. as:

$${}^1g(t) = {}_2{}^1R(t,\theta)g(t). \tag{8}$$

Computing the dot product of both sides in equations (8) and (2) with ${}^1\hat{j}$ yields:

$${}_2{}^1R(t,\theta)g(t) \cdot {}^2\hat{j} = {}^1g_1(t) \cdot {}^1\hat{j} + {}_2{}^1R(t,\theta)(\dot{\theta}{}^2\hat{j}) \cdot {}^1\hat{j}. \tag{9}$$

Now, recalling equation (4) and the dot product property $Ru \cdot Rv = u \cdot v$ we can write:

$${}_2{}^1R(t,\theta)g(t) \cdot {}_2{}^1R(t,\theta){}^2\hat{j} = {}^1g_1(t) \cdot {}^1\hat{j} + (\dot{\theta}{}^1\hat{j}) \cdot {}^1\hat{j},$$

which further gets simplified to:

$$g(t) \cdot {}^2\hat{j} = {}^1g_1(t) \cdot {}^1\hat{j} + \dot{\theta},$$

i.e. thus proving the claim in equation (7).

Given a certain constraint function, $f: \mathbb{R}^m \times \mathbb{R}^n \to \mathbb{R}$, that depends on the sensor samples reported at time t, we can formally express an error associated to this constraint as e: $\mathbb{R}^N \times \mathbb{R}^n \to \mathbb{R}^N$. Algebraically, this is equivalent to writing:

$$e(t,x)_k = f(v(t_k),x))^2, \tag{10}$$

where $t \in \mathbb{R}^N$ is an N-dimensional vector of time samples and $v(t_k)$ is an m-dimensional sample vector that we feed as argument to the constraint function f, and x is the main n-dimensional vector argument that we will need to find in order to minimize the error. We can also express this vector-valued error function as a scalar-valued function of the input:

$$E(x) = E_{k=0}^N (f(v(t_k),x))^2, \tag{11}$$

which needs to be minimized.

Using the example of a hinge joint, for the hinge joint constraint expressed by equation (1), the corresponding constraint function is:

$$f([{}^1g_1(t_k), g(t_k)], [{}^1\hat{j}, {}^2\hat{j}]) = \|g(t_k) \times {}^2\hat{j}\|_2 - \|{}^1g_1(t_k) \times {}^1\hat{j}\|_2. \tag{12}$$

with $v(t_k) = [{}^1g_1(t_k), g(t_k)]$ and $X = [{}^1\hat{j}, {}^2\hat{j}]$ written as concatenated row vectors for simplicity.

Ideally, the values of the constraint function in equation (12) should always be zero, hence both the vector and scalar function expressions for the error should attain a minimum equal to zero. Since the joints vectors must have unit norm, we must write additional constraints:

$$\|{}^1\hat{j}\|_2 = 1, \tag{13}$$

$$\|{}^2\hat{j}\|_2 = 1, \tag{14}$$

which further complicates the task of minimizing either (10) or (11) because these additional constraints are not included into the objective. One approach is to work in spherical coordinates, i.e.

$$\hat{j} = (\cos(\varphi_i)\cos(\theta_i), \cos(\theta_i)\sin(\theta_i), \sin(\theta_i))^T, \tag{15}$$

for $i \in 1, 2$. The solution the authors propose involve the vector error expression (10), for which $[{}^1\hat{j}, {}^2\hat{j}]$ is the unknown and the gyroscope angular velocities provide the coefficients. Since the resulting system is both overdetermined (usually N>6) and nonlinear, the authors propose solving $e(t, x) = 0$ iteratively, using a Gauss-Newton method. For simplicity, we will drop the time sample vector, t, using the k subscript to denote a certain vector component. The Jacobian of $e(x)$ w. r. t. x needs to be computed. If spherical coordinates are used, then $x = (\varphi_1, \theta_1, \varphi_2, \theta_2)$. This change of coordinates can make the computation of the Jacobian more tedious, but directly avoids a nonlinear equality constrained nonlinear minimization problem (i.e. we only have to minimize a nonlinear objective function).

If one desires to solve the problem using the equality constraints (14), then a formulation based on Lagrange multipliers becomes possible:

$$F(x) = E(x) + \lambda_1 (\|{}^1\hat{j}\|_2 - 1)^2 + \lambda_2 (\|{}^2\hat{j}\|_2 - 1)^2. \tag{16}$$

As a serious observation, if we consider the following possibility for the hinge joint setup:
the first link does not move, i.e. ${}^1g_1 = 0$
the second link is rotating through the action of the joint. As an example, suppose that the angular velocity is aligned with the local z-axis, i.e. $g = (0, 0, \dot{\theta})$ The iterative algorithm needs to be started with a guess for ${}^1\hat{j}$ and for ${}^2\hat{j}$. Setting ${}^2\hat{j}^{(0)} = (0,1,0)$, the problem will fail to converge. In this situation, the g is the only velocity that acts in the objective function. The isosurfaces of the objective function are a family of cylinders whose axis is aligned with the angular velocity (i.e. the z axis in this specific case). On the other hand, the equality constraints for the joint vector describe the unit sphere. If one uses Lagrange multipliers with the angular velocity being the North-South pole axis of that unit sphere and starts with the joint vector guess anywhere on the equator, the iterative process fails to modify the joint vector guess. This happens due to multiple reasons: the gradients of the cylinder and sphere are aligned, but the objective function is not minimized. Normally, the objective function's gradient will alter the guess, pulling it in the opposite gradient direction. Then, the modified guess is projected back onto the equality constraint manifold (the unit sphere). If one does not start from the equator of the unit sphere, then the algorithm converges, establishing the solution to be the N-S axis (i.e. collinear to the angular velocity vector).

In terms of hinge joint simplification, to further simplify the search for the joint axis in the case of the hinge joint constraint, we can assume that the IMU sensor frames are attached to the limbs in such a way that their local $^i\hat{y}$ axes are aligned perfectly with the bones of their support limbs, just as depicted in FIG. 7B. This assumption allows us to write the following geometrical observation in any local frame:

$$^1\hat{j} \cdot ^i\hat{y} = 0. \tag{17}$$

Equation (17) further restricts the search space of the hinge axis from the unit sphere to a single unit circle in the local xOz plane of each frame. This means that instead of two spherical angles required to describe the joint unit vectors in each local frame, now we only require a single angle, thus we can write:

$$^1\hat{j} = \begin{pmatrix} \cos(\theta_i) \\ 0 \\ \sin(\theta_i) \end{pmatrix}, \tag{18}$$

where $\theta_i$ is the angle represented in FIG. 7B. In this context, the norm of the cross product between the angular velocity and the joint axis becomes:

$$\|^1 g_1 \times ^1\hat{j}\| = (g_x^2 + g_y^2 + (g_z^2 - g_x^2)\cos^2(\theta_i) - g_x g_z \sin(2\theta))^{1/2}. \tag{19}$$

jacobian computation to find the approximate solutions that minimize the vector error in equation (10), we must compute the Jacobian of the N dimensional, vector valued error function $e(\theta_1, \theta_2)$ with respect to the two angle parameters, $\theta_1$ and $\theta_2$. The components of the Jacobian matrix are thus:

$$\frac{\partial e(t, \theta_1, \theta_2)_k}{\partial \theta_i} = (-1)^i \frac{-(^1 g_z^2 - ^1 g_x^2)\sin(2\theta_i) - 2^i g_z^i g_x \cos(2\theta_i)}{\|^1 g_i \times ^1\hat{j}\|} \cdot \cdot \tag{20}$$

$$(\|g(t_k) \times ^2\hat{j}\|_2 - \|^1 g_1(t_k) \times ^1\hat{j}\|_2).$$

By aligning the local y axes with the limb bones we have reduced the search space from 4 to 2 dimensions, i.e. the ($\theta_1$, $\theta_2$) angles. It is possible to use a Gauss-Newton iteration to find a solution for the general case, a strategy that obviously is still applicable to our reduced problem. In the absence of synchronized, noiseless sensor data, we have used artificially generated data by making use of a simplified arm representation and of equation (2). Consequently, we have written a Matlab script that solves the problem using the Levenberg-Marquardt nonlinear least squares algorithm by also providing the Jacobian equation (20). More specifically, we have set a constant angular velocity for the first sensor and used and assumed that the rotation happens about the local z axes, hence the rotation matrix is trivial to compute. The expressions are:

$$^1 g_1 = \frac{\alpha}{\sqrt{3}}(1, 1, 1)^T, \quad g = R_z(-\beta)^1 g_1 + (0, 0, \beta)^T.$$

Configuration of Sensor Units: Identification of Common World Directions

An alternate approach to solving both the problem of finding the angles between two links, but also their relative orientation matrix is to combine, in a sensor unit, an IMU (accelerometer) and a magnetometer (for example as described in various examples provided further above).

In overview, some embodiments provide methods including: receiving data from a first sensor unit $SU_1$, wherein the data from $SU_1$ is based upon a frame of reference defined by $SU_1$; receiving data from a second motion sensor unit $SU_2$, wherein the data from $SU_2$ is based upon a frame of reference defined by $SU_2$; wherein $SU_1$ and $SU_2$ are mounted to link members on opposed sides of a known joint; processing the data received from data from sensor unit $SU_1$ and sensor $SU_2$, thereby to determine two or more common world directions in the respective sensor data from sensor unit $SU_1$ and sensor $SU_2$; and based on the determination of the two common world directions, determining a skeletal relationship between sensor unit $SU_1$ and sensor $SU_2$. For example, this includes based on the determination of the two common world directions, defining data representative of a virtual skeletal body model.

In some embodiments, the at least two world directions are defined by a (i) magnetic field direction and a (ii) gravitational acceleration direction. In that regard, each sensor unit includes (i) a magnetometer, which provides data representative of the magnetic field direction; and (ii) an accelerometer, which provides data representative of the gravitational acceleration direction.

Turning to the detail, an exemplary approach is to identify an approximate period of absence of movement and measure the following quantities:

gravitational acceleration: in frame $\mathcal{F}_i$, the value the accelerometer indicates, $^i a_g$, is the approximation of the gravitational acceleration vector magnetic North: at the same time instant, measure $^i m$ the magnetic field orientation vector After this point onwards, the intermediate quaternion orientation values supplied by the sensor unit fusion output can be used to continuously compute the local expressions for both $^i a_g$ and $^i m$.

In some embodiments, a triad method is applied for recovering relative orientation matrices. In the following, we assume two limbs connected through a spherical joint. For brevity, we will denote the frame of the first and second limb sensor as $\mathcal{F}_1$ and $\mathcal{F}_2$, respectively. The current goal is to derive the $_1^2 R$ rotation matrix that aligns the two frames. Naturally, the following identities hold:

$$^2 m = {_1^2 R} \, ^1 m, \tag{21}$$

$$a_g = {_1^2 R} \, a_g. \tag{22}$$

To recover the rotation matrix, $_1^2R$, we use the triad method consisting in the following simple steps:

1. normalize:

$$^i\hat{m} = \frac{^im}{\|^im\|} \text{ and } ^i\hat{a}_g = \frac{^i\hat{a}_g}{\|^i a_g\|}.$$

2. build orthonormal bases:

$$^i\hat{b} = \frac{^im \times ^ia_g}{\|^im \times ^ia_g\|}, ^i\hat{c} = ^i\hat{m} \times ^i\hat{b}.$$

We arrange equations (22) in matrix form:

$$[^2\hat{m} \vdots ^2\hat{b} \vdots ^2\hat{c}] = {}_1^2R[^1\hat{m} \vdots ^1\hat{b} \vdots ^1\hat{c}], \quad (23)$$

which leads to the solution:

$$_1^2R[^2\hat{m} \vdots ^2\hat{b} \vdots ^2\hat{c}][^1\hat{m} \vdots ^1\hat{b} \vdots ^1\hat{c}]^T. \quad (24)$$

This allows for defining of transformations and/or construction of a skeletal model for the sensor units. That is, as described above, this approach enable direct recovery of relative transforms between reference frames of two sensors. This assumes that the sensors are sensibly rigidly attached to the limbs (i.e. they rotate with the limbs, with negligible roll/pitch/yaw offsets and with minimal sway, heave and surge translations).

In some embodiments each sensor units (or each of a subset the sensor units) includes multiple accelerometers. For example, a sensor unit includes (i) a first magnetometer tuned to a first sensitivity range thereby to provide data below a threshold motion-influenced saturation point; and (ii) a second accelerometer tuned to a second sensitivity range thereby to provide data including data above the threshold motion-influenced saturation point, such that the at least one sensor unit provides continuous data representative of magnetic field direction in spite of motion above the threshold motion-influenced saturation point. This allows one accelerometer to provide data suitable for sensor configuration, and another to provide more detailed/accurate data in a specific motion acceleration range for the purpose of skill monitoring. For example that range may be set on a skill-specific basis, based on relevant observable data condition attributes.

Configuration of Sensor Units: Inverse Kinematics Pose Estimation

Some embodiments make use of an inverse kinematics corrective model. In overview, the general principle is to track an end-effector (such as a hand or foot) as if it were seen from the point of view of a base (such as a shoulder or hip). Using accelerations and orientations, processing techniques are able to, in the case that the base sees the end-effector in a certain position, infer how the limbs between the base and end-effector are joined together (i.e. their relative angles).

As a practical example, it is possible for a person to grab an item, whilst and looking only at their hand. This involves, at a subconscious level, a process of inverse kinematics. The person does not know exactly how their elbow bends when reaching for the item, but the brain sees your hand and the item and tells the arm muscles to bend the elbow such that the hand gets closer to the item. In the present technical context, considering two sensors, on the hand and on the shoulder, the same process is possible. However, as an added level of complexity, there are several ways to place the hand on the item, so that the entire arm can be in multiple possible configurations. Intermediate sensors (for example a sensor on each of the forearm and upper arm) enables processing to discriminate between the actual pose and other possibilities.

One embodiment provides a method including receiving motion data for plurality of sensor units $SU_1$ to $SU_n$, wherein the motion data for each sensor unit is based upon a respective local frame of reference, and wherein each sensor is mounted to a respective body link of a wearer's body, wherein sensor units $SU_1$ to $SU_n$ include:

(i) a base sensor unit; and
(ii) an end effector sensor unit.

The method then includes determining motion of the end-effect sensor relative to the base sensor; and based on a kinematic model, inferring position and motion data for one or more joints intermediate the base sensor unit and the end effect sensor unit. For example, this includes, based on the inferring of position and motion data for the one or more joints intermediate the base sensor unit and the end effect sensor unit, defining data representative of a virtual skeletal body model. The plurality of sensor units preferably include one or more intermediate sensor units, wherein the one or more intermediate sensor units, are disposed on body links intermediate the base sensor unit and the end effector sensor unit. These are used to identify a "correct" one of a plurality of possible solutions to a kinematic estimation process. In one example, the base sensor is located proximal a shoulder, the end-effect sensor is located proximal a hand, and the one or more intermediate sensor units are mounted on the upper arm and/or forearm. Another example operates with hip, legs and feet.

Turning to the detail, one can assume an initial pose where the relative transforms between adjacent link frames are known up to a certain error. This is possible since the positioning of each sensor w.r.t. its link is known (via the suit's design prints). It is then possible to formulate an inverse kinematics problem, potentially using Denavit-Hartenberg conventions by viewing the joints of the arm as depicted in FIG. 7D.

For each arm, we can assume that the base reference system in which all computations are to be carried out is that of the shoulder, $\mathcal{F}_S$. The end effector is the hand. During the initialization stage, the pose of the $F_H$ hand frame needs to be known w.r.t. to the $F_s$ frame. This relies on the anatomical proportions of the arm links, summarized as follows:

a height H of an adult human is assumed
the length of the arm link (between the shoulder and elbow joints) is approximately 0.16H.
the length of the forearm link (between the elbow and wrist joints) is approximately 0.14H.
the length of the hand (between the wrist and the tip of the middle finger) is approximately 0.11H.
an angle $\alpha \approx 140°$ at the elbow joint can be assumed in the rest position.

To estimate the pose of the hand after the initialization epoch, we may rely on the data we get from the IMUs. Essentially, the angular velocities provide a way to integrate and ultimately recover an orientation estimate over time, but with respect to the initial pose of that IMU's frame. The accelerations, however, theoretically allow for measuring translational offsets. To better understand what are the unknowns and what is expected to be known between two consecutive time instances, $t_i$ and $t_{i+1}$, we list the ingredients that constitute the input and output of the approach we seek:

Input: $t_i, t_{i+1} > 0$ the time instances when the IMU samples were read, $_H^GR$, $_S^GR$ the rotation matrices of the hand and shoulder with respect to their initial poses at instance $t_{i+1}$. The G superscript underlines the assumption that the initial pose is the global reference which we must use in order to transform between different frames. Also, $^H a_H$ and $^S a_S$ are the accelerations read by their respective IMUs at time $t_{i+1}$, also expressed in their local frames. Also, $^s r(t_i)$ is the vector offset of the hand frame expressed in $\mathcal{F}_S$. Finally, for each joint (there are 7 in total), we assume the angle offsets $\theta_k(t_i)$ are known at instance $t_i$, k=$\overline{1,7}$.

Output: the joint angular offsets, $\theta_k(t_{i+1})$, k=$\overline{1,7}$.

Explanations $^s r(t_i)$ is useful in recovering the translational offset at instance $t_{i+1}$. The angular velocity measured at $t_{i+1}$ reveals a relative transform describing how the shoulder frame has rotated over this short period, i.e. a matrix $^S R_{t_i}^{t_{i+1}}$. Thus, $^S R_{t_i}^{t_{i+1}} {}^s r(t_i)$ tells how the shoulder-to-hand vector looks like in the shoulder frame at time $t_{i+1}$ assuming only a rotation happened. In many situations, a transport acceleration of the hand with respect to the shoulder will modify the length of the shoulder-to-hand vector:

$$^s a_{transport} = {}_H^S R\, ^H a_H - {}^S a_S. \tag{25}$$

Using Euler integration, we can update a transport linear velocity and then recover the corrected offset vector. More specifically, $$^s v_{transport}(t_{i+1}) = {}^S R_{t_i}^{T_{i+1}} {}^s v_{transport}(t_i) + \Delta t\, ^s a_{transport}, \tag{26}$$

$$^s r(t_{i+1}) = {}^S R_{t_i}^{T_{i+1}} {}^s r(t_i) + \Delta t\, ^s v_{transport}(t_{i+1}) \tag{27}$$

The orientation matrix is more trivial to obtain:

$$_H^S R = {}_G^S R\, _G^H R^{-1}. \tag{28}$$

From equations (27) and (28) we can see that all the prerequisites of an inverse kinematics formulation are in place. One possible approach is to use cyclic coordinate descent (CCD) and, by reading the data from the sensors and have more educated guesses for which joint to modify first. To understand what this means, imagine the elbow angle decreases during an abduction movement (grab an apple and bring it to your mouth). CCD usually adjusts the angles starting from the root towards the end effector. In this case, the gyroscopes of the arm and forearm should reveal a more intense movement due to the elbow joint. Hence that must be the most promising axis to optimize for first. In a sense, the sensors provide an inherent order for applying the CCD iterations to individual joints.

Once the $\theta_k(t_{i+1})$ angles are recovered, the orientation estimates of the IMU sensors are corrected.

It will be appreciated that these are provided as illustrative techniques for configuration of MSUs, and that these are not intended to be limiting in any way. Furthermore, it should be appreciated that in some embodiments ODCs are defined in a manner that does not require conversion of MSD from multiple MSUs to a common frame of reference, relying instead on self-referenced aspects of MSU-specific data (for example based on a path in which a given MSU accelerates according to its own frame of reference, which is optionally combined with a path in which a second MSU accelerates in its own frame of reference).

Conclusions and Interpretation

It will be appreciated that technology described above provides advances across a range of the described aspects, including but not limited to: (i) analysis of a skill thereby to understand its defining characteristics; (ii) defining of protocols thereby to enable automated analysis of a skill using one or more PSUs; (iii) defining and delivery of content that makes use of the automated analysis thereby to provide interactive end-use content, such as skills training; (iv) adaptive implementation of skills training programs; (v) hardware and software that facilitates the delivery of content to end users; (vi) hardware and software that facilitates the experiencing of content by end users; and (vii) technology and methodologies developed to facilitate the configuration and implementation of multiple motion sensor units for the purpose of human activity monitoring.

Unless specifically stated otherwise, as apparent from the following discussions, it is appreciated that throughout the specification discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A computer implemented method for enabling a user to configure operation of local performance monitoring hardware including a processing device and one or more sensor strands, each of the sensor strands comprising connected and interchangeable performance sensor units, the method including:
    enabling the user to select a set of one or more skills from among a plurality of skills;
    in response to the user's selection of the set of one or more skills, enabling the user to select an expert knowledge variation from among a plurality of expert knowledge variations for the set of one or more skills selected, the plurality of expert knowledge variations differing from each other and respectively corresponding to a plurality of different experts; and
    in response to the user's selection of the expert knowledge variation, providing to the processing device downloadable data that corresponds to the set of one or more skills and the expert knowledge variation selected, the downloadable data including:
    state engine data that enable the processing device to identify attributes of an attempted performance of the set of one or more skills based on representative data provided by the performance sensor units sensing the attempted performance of the set of one or more skills; and
    user interface data that enable a user interface to provide instructions or feedback based on the attributes of the attempted performance of the set of one or more skills and on the expert variation selected.

2. A method according to claim 1, wherein the plurality of expert knowledge variations include:
    a first expert knowledge variation associated with a first set of state engine data;
    and a second expert knowledge variation associated with a second set of state engine data different from the first set of state engine data, the second different set of state engine data enabling identification of one or more expert-specific attributes of a performance that are not identified using the first set of state engine data.

3. A method according to claim 2, wherein the one or more expert-specific attributes relate to a style of performance or a coaching knowledge associated with the expert that corresponds to the second expert knowledge variation.

4. A method according to claim 3, wherein the style of performance is represented by defined attributes of body motion that are observable with the sensor strands.

5. A method according to claim 2, wherein the one or more expert-specific attributes are based on a coaching view of the expert that differs from a consensus view as to how a particular symptom is to be observed or defined.

6. A method according to claim 1, wherein the plurality of expert knowledge variations include:
    a first expert knowledge variation that identifies, in the representative data derived from the performance sensor units, a first set of observable data conditions associated with the set one or more skills; and
    a second expert knowledge variation that identifies, in the representative data derived from the performance sensor units, a second set of observable data conditions associated with the set of one or more skills, the second set of observable data conditions being different from the first set of observable data conditions.

7. A method according to claim 6, wherein a difference between the first set of observable data conditions and the second set of observable data conditions accounts for different styles or coaching advice of the experts associated with the respective expert knowledge variations.

8. A method according to claim 1, wherein the plurality of expert knowledge variations include:
    a first expert knowledge variation providing a first set of feedback data to the user in response to observing defined observable data conditions associated with the set of one or more skills; and
    a second expert knowledge variation providing a second set of feedback data to the user in response to observing the defined observable data conditions associated with the set of one or more skills, the second set of feedback data being different from the first set of feedback data.

9. A method according to claim 8, wherein a difference between the first set of feedback data and the second set of feedback data accounts for different coaching advice or audio data representative of voices of the experts associated with the respective expert knowledge variations.

10. A method according to claim 6, further including generating the first set of observable data conditions and the second set of observable data conditions.

11. A method according to claim 1, further comprising for the set of one or more skills, providing a cloud hosted marketplace that is configured to make available for procurement by one or more users: (i) a standard version of skills training content; and (ii) the expert knowledge variation of the skills training content.

12. A method according to claim 1, further including generating the plurality of expert knowledge variations.

13. A method according to claim 1, wherein the plurality of expert knowledge variations include:
    a first set of training content data associated with a first protocol for mapping symptoms to causes; and
    a second set of training content data associated with a second protocol for mapping symptoms to causes, the second set of training content data providing at least one expert-specific relationship between a symptom and a cause different from the first set of training content data.

14. A method according to claim 13, wherein:
    the first set of training content data is associated with a first set media content; and
    the second set of training content data is associated with a second set of media content, the second set of training content data being configured to provide media content personalized to a particular expert.

15. A method according to claim 1, wherein the state engine data further enables the processing device to transform motion data from the performance sensor units to a common frame of reference and determine a skeletal relationship between the performance sensor units.

16. A method according to claim 1, wherein the downloadable data further includes sensor configuration data that the processing device uses to configure the sensor strands to operate in a defined manner and thereby to provide the representative data of the attempted performance of the set of one or more skills.

17. A method according to claim 16, wherein the sensor configuration data indicates one of a sampling rate and a resolution for at least one of the performance sensor units.

* * * * *